(12) United States Patent
Chu et al.

(10) Patent No.: US 9,700,560 B2
(45) Date of Patent: *Jul. 11, 2017

(54) 2'-FLUORO-6'-METHYLENE CARBOCYCLIC NUCLEOSIDES AND METHODS OF TREATING VIRAL INFECTIONS

(71) Applicant: UNIVERSITY OF GEORGIA RESEARCH FOUNDATION, INC., Athens, GA (US)

(72) Inventors: Chung K. Chu, Stratham, GA (US); Jianing Wang, San Diego, CA (US)

(73) Assignee: UNIVERSITY OF GEORGIA RESEARCH FOUNDATION, INC., Athens, GA (US)

(*) Notice: Subject to any disclaimer, the term of this patent is extended or adjusted under 35 U.S.C. 154(b) by 150 days.

This patent is subject to a terminal disclaimer.

(21) Appl. No.: 14/079,412

(22) Filed: Nov. 13, 2013

(65) Prior Publication Data

US 2014/0073606 A1 Mar. 13, 2014

Related U.S. Application Data

(63) Continuation of application No. PCT/US2012/037612, filed on May 11, 2012, which is a continuation-in-part of application No. 13/107,713, filed on May 13, 2011, now Pat. No. 8,816,074, which is a continuation-in-part of application No. PCT/US2010/056808, filed on Nov. 16, 2010.

(60) Provisional application No. 61/281,342, filed on Nov. 16, 2009.

(51) Int. Cl.
| | |
|---|---|
| *C07D 473/34* | (2006.01) |
| *A61K 31/52* | (2006.01) |
| *A61K 45/06* | (2006.01) |
| *A61K 31/675* | (2006.01) |

(52) U.S. Cl.
CPC ............ *A61K 31/52* (2013.01); *A61K 31/675* (2013.01); *A61K 45/06* (2013.01); *C07D 473/34* (2013.01)

(58) Field of Classification Search
None
See application file for complete search history.

(56) References Cited

U.S. PATENT DOCUMENTS

| | | | |
|---|---|---|---|
| 5,340,816 A | 8/1994 | Zahler et al. | |
| 8,816,074 B2* | 8/2014 | Chu et al. | 544/273 |
| 8,946,244 B2* | 2/2015 | Chu et al. | 514/263.4 |
| 2002/0198171 A1 | 12/2002 | Schinazi et al. | |
| 2004/0110718 A1 | 6/2004 | Devos et al. | |
| 2004/0157793 A1 | 8/2004 | Stuyver et al. | |
| 2007/0042940 A1 | 2/2007 | LaColla et al. | |
| 2007/0225249 A1 | 9/2007 | Shi | |

FOREIGN PATENT DOCUMENTS

EP 0212956 * 3/1987 .......... C07D 473/18

OTHER PUBLICATIONS

Vippagunta et al., "Crystalline Solids" Advanved Drug Delivery Reviews (2001) vol. 48 pp. 3-26.*
Jain et al., "Polymorphism in Pharmacy" Indian Drugs (1986) vol. 23 No. 6 pp. 315-329.*
Braga et al., "Making Crystals from Crystals: a green route to crystal engineering and polymorphism" Chemcomm (2005) pp. 3635-3645.*
Lieberman et al., "Pharmaceutical Dosage Forms: Tablets" published 1990 by Marcel Dekker, Inc, pp. 462-472.*
Wang, J. et al.; Viral activity of novel 2'-fluoro-6'-methylene-carbocyclic adenosine against wild-type and drug-resistant hepatitis B virus mutants. Bioorg. & Med. Chem. Lett. Sep. 1, 2011, vol. 21, pp. 6328-6331.
Wang, J. et al.; D- and L-2',3'-didehydro-2',3'-dideoxy-3'-fluoro-carbocyclic nucleosides: synthesis, anti-HIV activity and mechanism of resistance. J. Med. Chem. Apr. 19, 2007, vol. 50, pp. 1828-1839.

* cited by examiner

*Primary Examiner* — Eric Olson
(74) *Attorney, Agent, or Firm* — Henry D. Coleman; R. Neil Sudol

(57) ABSTRACT

The present invention relates to 2'-Fluoro-6'-methylene carbocyclic nucleosides, pharmaceutical compositions containing these nucleosides and their use in the treatment or prophylaxis of a number of viral infections and secondary disease states and conditions thereof, especially including Hepatitis B virus (HBV) and secondary disease states and conditions thereof (cirrhosis and liver cancer), Hepatitis C virus (HCV), Herpes Simplex virus I and II (HSV-1 and HSV-2), cytomegalovirus (CMV), Varicella-Zoster Virus (VZV) and Epstein Barr virus (EBV) and secondary cancers which occur thereof (lymphoma, nasopharyngeal cancer, including drug resistant (especially including lamivudine and/or adefovir resistant) and other mutant forms of these viruses, especially HBV.

20 Claims, 19 Drawing Sheets

Scheme 1

Scheme 2

Alternative Scheme 2

FIGURE 10

Table 1. In vitro anti-HBV activity of compound FMCA (compound 15/18) against lamivudine and adefovir drug-resistant mutants on the intracellular HBV DNA replication assay

| Strain | Anti-HBV activity 15/18 (μM) | | | | Adefovir (μM) | | | Lamivudine (μM) | | |
|---|---|---|---|---|---|---|---|---|---|---|
| | $EC_{50}$[b] | $EC_{90}$[c] | $CC_{50}$[d,e] | Fold resistance ($EC_{90}$) | $EC_{50}$ | $EC_{90}$ | Fold resistance ($EC_{90}$) | $EC_{50}$ | $EC_{90}$ | Fold resitance ($EC_{90}$) |
| Wild Type | 1.5 | 4.5 | >100 | - | 1.3 | 7.1 | - | 0.2 | 0.6 | - |
| rtM204V | 1.8 | 4.7 | >100 | 1.0 | 1.6 | 7.0 | 1.0 | >100 | >100 | >166 |
| rtM204I | 1.0 | 5.0 | >100 | 1.1 | 1.9 | 8.0 | 1.1 | >100 | >100 | >166 |
| rtL180M | 2.1 | 5.1 | >100 | 1.1 | 5.5 | 7.7 | 1.1 | 1.5 | 22 | 36.7 |
| rtLM/rtMV[a] | 2.2 | 5.5 | >100 | 1.2 | 2.1 | 8.5 | 1.2 | >100 | >100 | >166 |
| rtN236T | 1.7 | 4.6 | >100 | 1.0 | 7.8 | 36 | 5.1 | 0.2 | 0.9 | 1.5 |

FIGURE 11

Table 2  *In vitro* anti-HBV activity against lamivudine and adefovir drug-resistant mutants in the intracellular HBV DNA replication assay

| Compounds | HBV Strains | | | | |
|---|---|---|---|---|---|
| | Wild-type | | | L180M+M204V+S202G | |
| | $EC_{50}$ (µM) | $EC_{90}$ (µM) | $CC_{50}$ (µM) | $EC_{50}$ (µM) | |
| Compound 15/18 | 0.548±0.056 | 6.0±0.400 | >300 | 0.67 | |
| Compound 15P/18P | 0.062±0.011 | 0.46±0.060 | >300 | 0.054 | |
| Lamivudine | 0.056±0.003 | 0.142±0.008 | >300 | >500[a] | |
| Entecavir | 0.008 | 0.033 | 28 | 1.20[b] | |

A.

B.

# 2'-FLUORO-6'-METHYLENE CARBOCYCLIC NUCLEOSIDES AND METHODS OF TREATING VIRAL INFECTIONS

The present application claims priority from international patent application number PCT/US2012/037612 filed on May 11, 2012, which claims priority as a continuation-in-part from U.S. application Ser. No. 13/107,713, filed 13 May 2011, entitled "2'-Fluoro-6'-Methylene Carbocyclic Nucleosides and Methods of Treating Viral Infections", now U.S. Pat. No. 8,816,074, which is a continuation-in-part application claiming priority from international patent application number PCT/US2010/056808 filed Nov. 16, 2010, now U.S. Pat. No. 8,946,244, which claims priority from U.S. provisional patent application No. 61/281,342 filed Nov. 16, 2009, the entire contents of all of said applications being incorporated by reference herein.

CLAIM OF PRIORITY AND GOVERNMENT RIGHTS

The work which gave rise to this patent application was supported by U.S. Public Health Search Grant no. AI25899 from the National Institute of Allergy. Consequently, the government retains certain rights in the invention.

FIELD OF THE INVENTION

The present invention relates to 2'-Fluoro-6'-methylene carbocyclic nucleosides, pharmaceutical compositions containing these nucleosides and their use in the treatment or prophylaxis of a number of viral infections and secondary disease states and conditions thereof, including Hepatitis B virus (HBV) and secondary disease states and conditions thereof (cirrhosis and liver cancer), including liver cancer, Hepatitis C virus (HCV), Herpes Simplex virus I and II (HSV-1 and HSV-2), cytomegalovirus (CMV), Varicella-Zoster Virus (VZV) and Epstein Barr virus (EBV), including drug resistant (especially including lamivudine and/or adefovir resistant) and other mutant forms of these viruses. The use of 2'-Fluoro-6' methylene-carbocycolic adenosine (FMCA, compound 15/18) and its monophosphate prodrug (phosphoramidate) (compound 15P) exhibits excellent activity against HBV and in particular, drug resistant forms of HBV, especially HBV resistant to lamivudine and/or adefovir anti-HBV agents. The prodrug form in particular was unexpectedly found to be exceptionally active against drug resistant forms of HBV.

BACKGROUND OF THE INVENTION

Hepatitis B virus (HBV) infection is one of major global health problems.[1] Although primary HBV infections in most adults are self-limited, 3-5% patients do not resolve and develop into chronic infection and this rate is much higher among young children infected with HBV.[2] The estimated number of the chronic hepatitis B (CHB) carriers is approximately 350-400 million worldwide, with more than one million deaths annually resulted from cirrhosis, liver failure and hepatocellular carcinoma.[2]

Agents currently available for the treatment of HBV infection can be classified into two main categories: immunomodulator and nucleoside/nucleotide analogues. Although the efficacy of INF α, a representative immunomodulator, has been established by a numerous studies, the clinical application of INFα has been compromised by the low overall response rate, side effects and high cost.[3,4]

Nucleoside/nucleotide analogs, on the hand, continue to dominate the anti-HBV therapy. There are at least six nucleosides/nucleotides in the clinical use, including lamivudine (Epivir-HBV®, GlaxoSmithKline), adefovir dipivoxil (Hepsera®, Gilead), entecavir (Baraclude®, Bristol-Myers Squibb), telbivudine (Tyzeka®, Idenix/Novartis), clevudine (Levovir® in South Korean, Phase III in US, Bukwang/Pharmasset) and most recently tenofovir (Viread®, Gilead). (FIG. 1). These agents significantly suppress the replication of HBV DNA to a lowest possible level which leads to the favorable clinical outcomes and prevents advanced liver sequelae. Indeed, the introduction of these oral nucleosides/nucleotides is the breakthrough in the anti-HBV therapy. It has been reported that the number of patients in US registered for liver transplantation has been decreased 30% since widespread application of nucleoside anti-HBV agents.[5]

There is no solid evidence that current nucleosides/nucleotides treatments have direct effect on the HBV covalently closed circular DNA (cccDNA), which has a long half-life and is believed to serve as the transcriptional template as long as the termination of the therapy,[6] leading to the viral DNA rebound. Consequently, long-term, highly effective antiviral therapy may be required to prevent viral relapse following discontinuation of the treatment.[7] Unfortunately, long-term nucleosides/nucleotides treatment is always associated with the development of drug-resistant mutants which significantly compromised the efficacy. The nature of HBV polymerase coupled with high replication rate lead to the emergence of HBV mutants which have survival advantage in the presence of certain antiviral agents.[8] The current use of lamivudine, the first approved anti-HBV nucleoside, has been limited by the high frequency of lamivudine resistance (most commonly rtL180M±rtM204V/I). The in vitro study indicated rtL180M+rtM204V/I mutations result in a >1000-fold decreased susceptibility of the virus to lamivudine without significant impairing of polymerase function.[9,10] In clinical practice, the approximate rate of resistance of lamivudine is about 20% at the end of 1-year and 70% after 5-year treatment.[11-14] Telbivudine, another L-nucleoside, is cross-resistant to the major lamivudine mutation at YMDD motif, represented by the rtM204I. It is associated with a lower rate of resistance compared to lamivudine after 1 year therapy (around 5% in HBeAg-postive patients), while the rate jumps to 22% after 2 years.[15] These data may indicate a possible high rate of drug-resistance in the longer duration of telbivudine therapy. Adefovir belongs to the acyclic phosphonate. Bearing distinct acyclic sugar moieties, this nucleoside is not cross-resistant to the L-nucleosides. However, there are two primary adefovir-resistant mutations at codon 181 (rtA181T) and codon 236 (rtN236T) which result in two-fold to nine-fold increase in median effective concentration.[16-18] Although the fold of increase is modest, reports showed non-response to the adefovir treatment is associated with three patients who developed a mutation.[19,20] The rate of developing resistance with adefovir treatment is also significant high, with about 3% at 2 years and 29% at 5 years.[21] The other potent anti-HBV nucleoside, entecavir, has a high genetic barrier to resistance. However, in patients with pre-existing lamivudine-resistant mutations, the probability of entecavir resistance increases from 1% at 1 year to 51% to 5 years.[22,23] Therefore, entecavir is not recommended as monotherapy in patients with YMDD mutations. Although there is no solid evidence of detecting resistance to date after continuous treatment with tenofovir or clevudine in clinical, results after prolonged therapy remain to be determined.

The development of antiviral resistance is generally associated with worse clinical outcomes.[8] For example, the efficacy of lamivudine treatment was negated by the development of drug resistance.[24] Patients who developed drug resistance were less likely to demonstrate histological improvement (44% versus 77%) and more likely to show liver deterioration (15% versus 5%) in comparison to subjects who have no evidence of drug resistance.[24] Particularly, there have been reported hepatitis flares and hepatic decomposition in patients following the development of antiviral resistance.[25] Therefore, a careful management of antiviral resistance is paramount in the anti-HBV treatment. Add-on (combination with different nucleosides or interferon) therapy and switching to an alternative nucleoside monotherapy are two major options for patients with suboptimal response to the initial single nucleoside treatment. Although it is not clear which is the most effective way in the management of resistance, providing additional/alternative agents with high genetic barrier and with different resistance profile from the initial drug are critical. Current anti-HBV arsenal is limited. Therefore it is important to develop novel nucleoside analogs which are active against not only wild type (WT) but also existing HBV drug-resistant mutants. During the course of our drug discovery programs, introduction of fluorine atom onto the sugar moiety generated a number of novel nucleosides with interesting biological interesting nucleosides.[26-35] Therefore, it is of great interest to explore the substitution of fluorine atom on the carbocyclic nucleosides with an 6'-exo-cyclic alkene (6'-methylene). Herein, we would like to report the invention of the interesting fluorinated carbocyclic nucleoside which is active against HBV-WT as well as lamivudine- and adefovir-resistant mutants.

The search for antiviral agents treatment of Hepatitis B virus, Hepatitis C virus, Herpes Simplex virus I and II (HSV I and II), cytomegalovirus (CMV), Varicella-Zoster Virus (VZV) and Epstein Barr virus is an ongoing process and the present invention is directed to those viral disease states.

Alternatively, the following reagents and conditions were used: (a) DIAD, Ph$_3$P, 6-chloropurine, THF, rt; (b) NH$_3$, MeOH, 100° C.; (c) OsO$_4$/NMO, acetone/H$_2$O, rt; (d) i) NaN$_3$, DMF, 140° C.; (ii) H$_2$/Pd/C, EtOH, rt; (e) i) 1-bromocarbonyl-1-methylene acetate, acetonitrile, rt; (ii) Zn/HOAc, DMF; (f) DIAD, Ph$_3$P, THF, 0° C.; (g) TFA, CH$_2$Cl$_2$, rt; (h) DIABAL-H, CH$_2$Cl$_2$, $-78°$ C.

Figure 6:
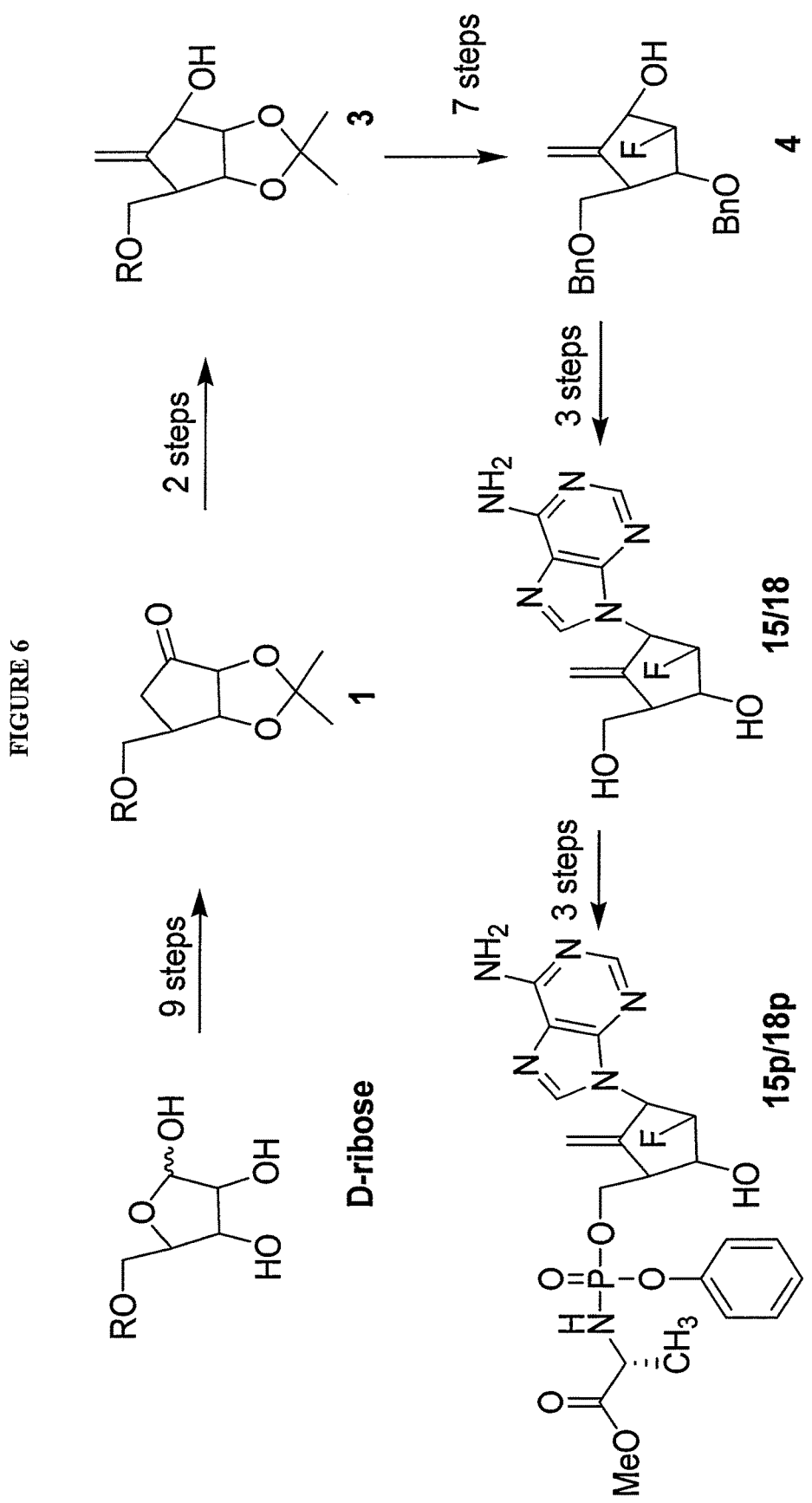

FIG. 6 shows yet another alternative chemical scheme, which provides a series of synthetic steps to compound 15/18. This is an abbreviated method as the synthesis as otherwise provided herein.

Figure 7:
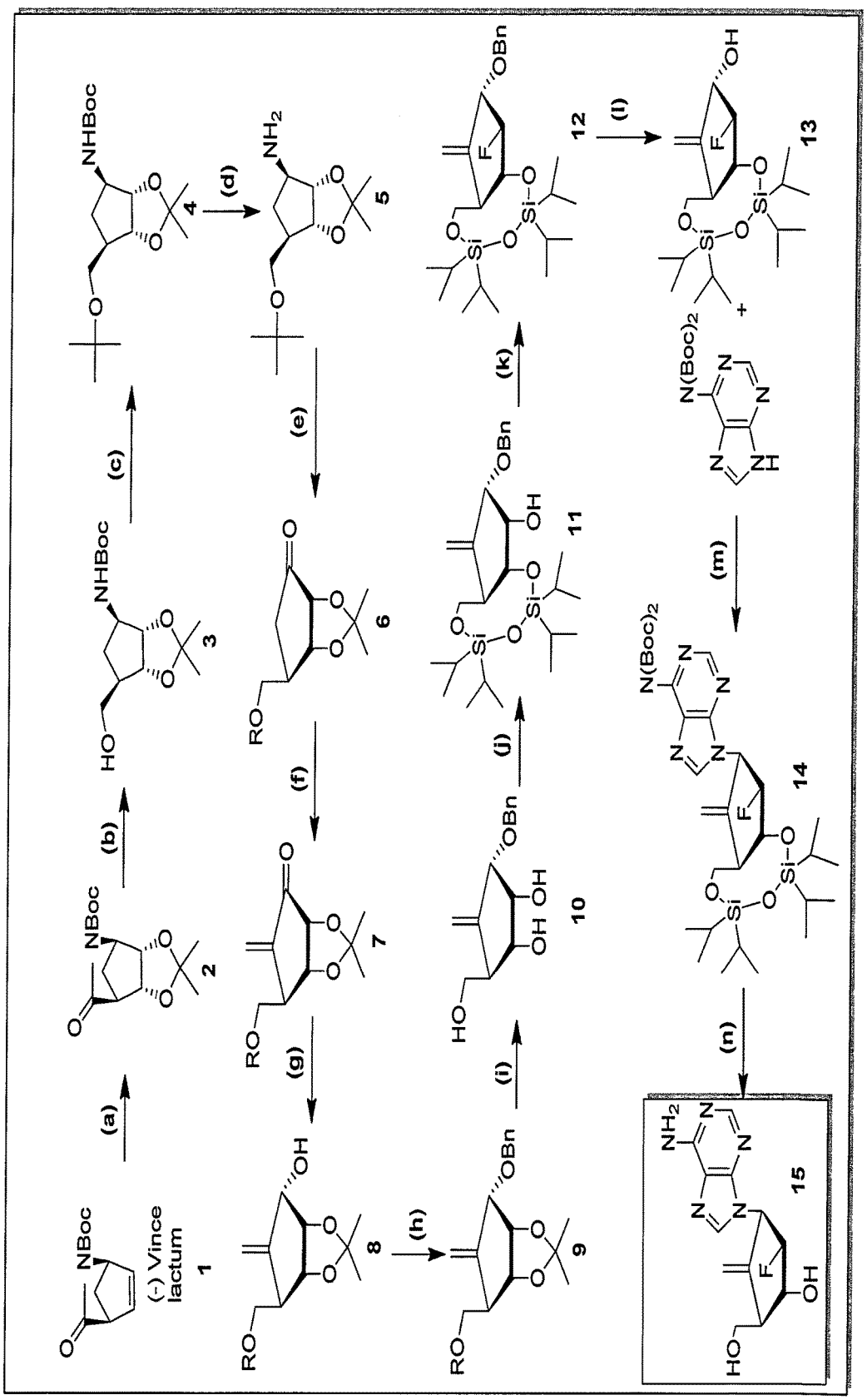

FIG. 7 shows alternative scheme 3, which provides a series of synthetic steps to compound 15/18. The following reagents and conditions are used: (a) i) OsO$_4$/NMO, Acetone/water (ii) dimethoxy propane, PTSA, Acetone (b) NaBH$_4$, Methanol (c) tert-butyl chloride, NaH, DMF (d), TFA, DCM or NaO$^t$Bu, H$_2$O/THF (e) NBS, NaOMe, ethanol, H$^+$ (f) (i) LDA, Eshenmoser's salt, THF, $-78°$ C.; ii) MeI, rt; iii) sat. NaHCO$_3$ solution, rt; (g) NaBH$_4$/CeCl$_3$.7H$_2$O, MeOH (h) NaH, BnBr, DMF, (i) TFA/H$_2$O (2:1), 50° C.; (j) TIDPSCl$_2$/Imidazole, DMF; (k) DAST, CH$_2$Cl$_2$, (l) BCl$_3$, CH$_2$Cl$_2$; (m) DIAD, Ph$_3$P, THF; (m) TFA, CH$_2$Cl$_2$.

Figure 8:
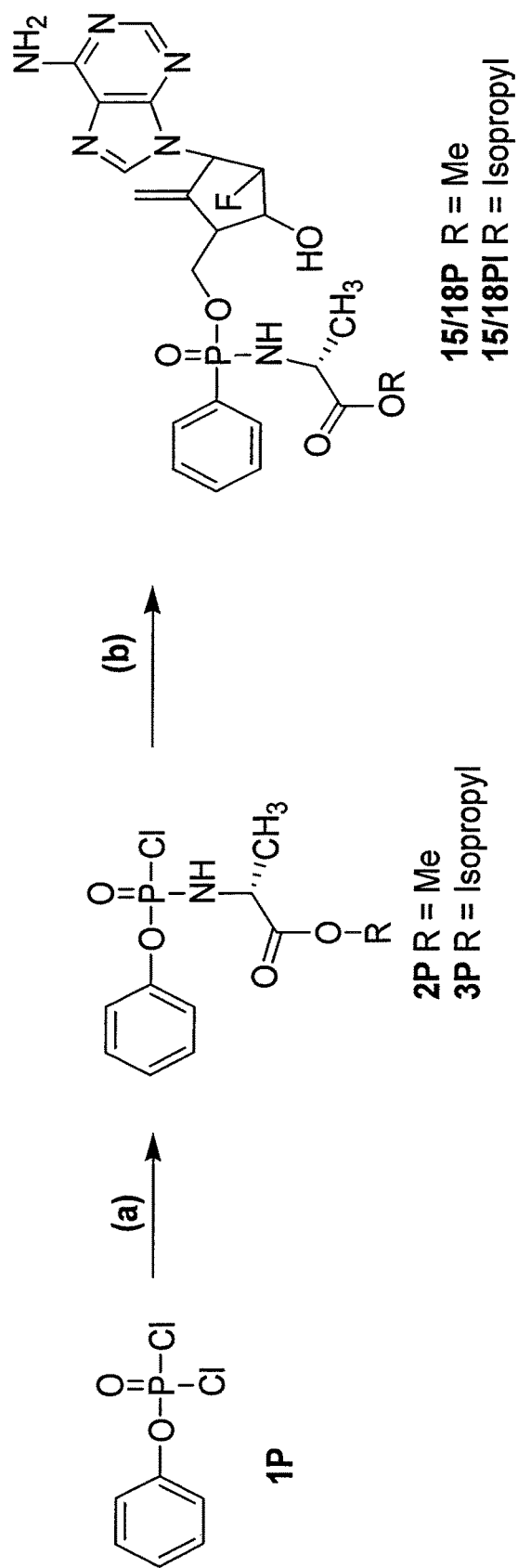

FIG. 8 shows the prodrug synthesis of compound 15P/18P and 15PI/18PI. The synthesis proceeds from the dichlorophosph 1P by reacting L-alanine substituted ester hydrochloride in the presence of triethylamine in methylene chloride solvent to produce 2P or 3P, the methyl ester or isopropyl ester of chlorophenylphosphoryl-L-alaninate. To the phosphoryl intermediate 2P or 3P, is added compound 15/18 in N-Methylimidazole in dry tetrahydrofuran overnight to produce the prodrug analogs 15P/18P and 15PI/18PI as indicated. It is noted that while the methyl and isopropyl ester 15P/18P and 15PI/18PI are shown, the corresponding ethyl and isobutyl esters are also made via the same procedure. The synthesis in FIG. 8 shows a diasteromeric mixture of compounds (both the carbon exhibiting a stereospecific methyl on the alanine group and the phosphorous group are chiral centers, but the phosphorous group shown is racemic, resulting in a diastereomeric mixture of compounds). These diastereomers are readily separated using standard methods available in the art including selective crystallization techniques and/or chiral columns.

Figure 9:
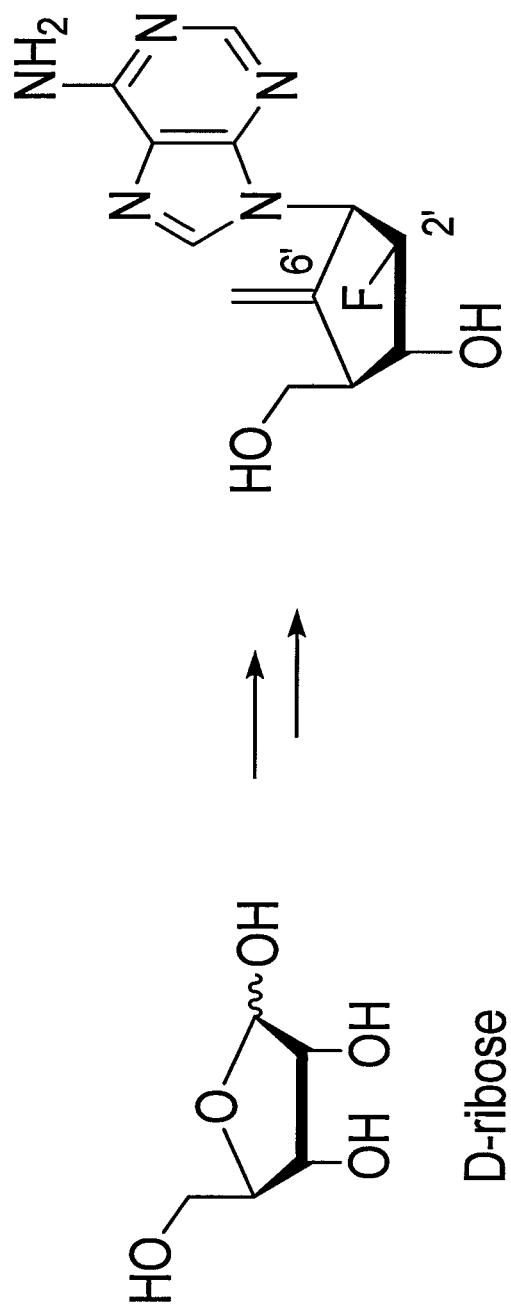

FIG. 9 shows a rough schematic of the chemical schemes otherwise disclosed in the present specification. The present synthesis provides an approach to synthesizing compounds according to the present invention from D-ribose as indicated.

FIG. 10 shows in vitro anti-HBV activity of compound 15/18 against lamivudine and adefovir drug-resistant mutants on the intracellular HBV DNA replication assay. The figure legend for Table 1 is as follows: [a]rtLM/rtMV=rt180M/rtM204V double mutant. [b]Effective concentration required to inhibit 50% of HBV-DNA. [c]Concentration required to reduce infectious virus titer by 90%. [d]The > sign indicates that the 50% inhibition was not reached at the highest concentration tested. [e]The drug concentration required to reduce the viability of cell as determined by MTT assay by 50% of untreated control after 3 day.

FIG. 11 shows Table 2 setting forth the in vitro anti-HBV activity compound 15/18, its monophosphate prodrug 15P/18P, lamivudine and entecavir against wild type and entecavir drug-resistant mutant in Huh7 cells. [a] see reference (22); [b]reference (23) of second set of references.

FIGS. 12A and 12B shows the anti-HBV activity of compound 15P/18P. against HBV genotype C entacavir resistant clone (L180M+S202G+M204V) in Huh7 cells. FIG. 12B shows the $IC_{50}$ value of compound 15/18 of 0.054 μM.

Figure 13:
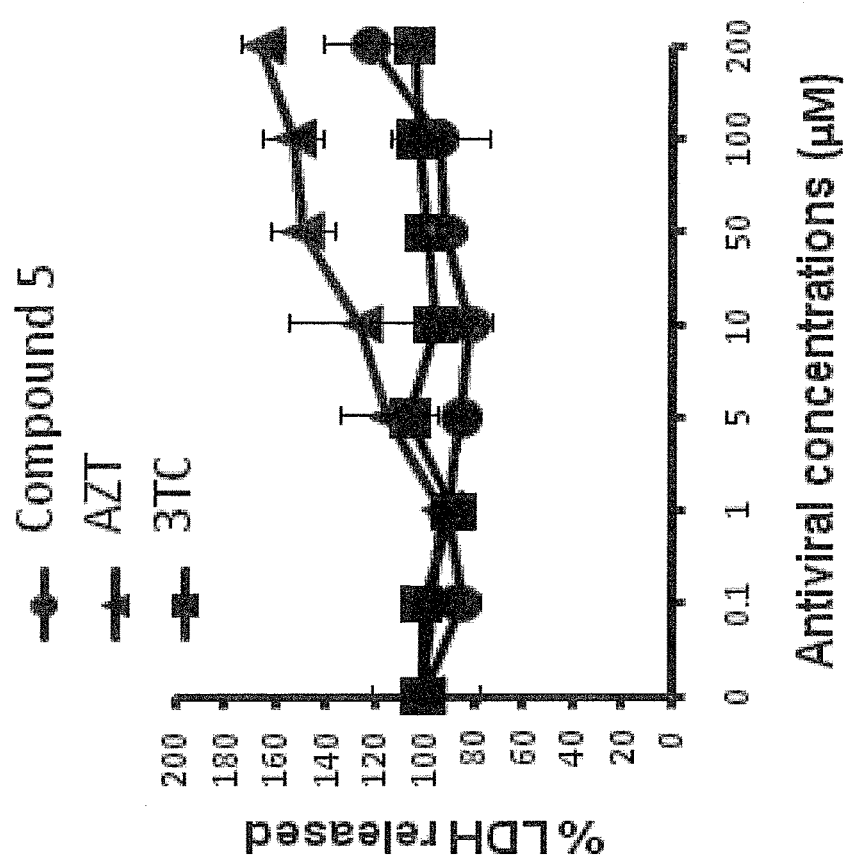

FIG. 13 shows the mitochondrial toxicity of compound 15/18, AZT and 3TC through lactase dehydrogenase release (LDH) assay.

FIG. 14 shows the binding mode and van der Waals interaction of compound 15/18 A) in wild-type HBV and B) in N236T adefovir mutant HBV. Lighter dotted lines are hydrogen bonding interactions (<2.5Å).

Figure 15:
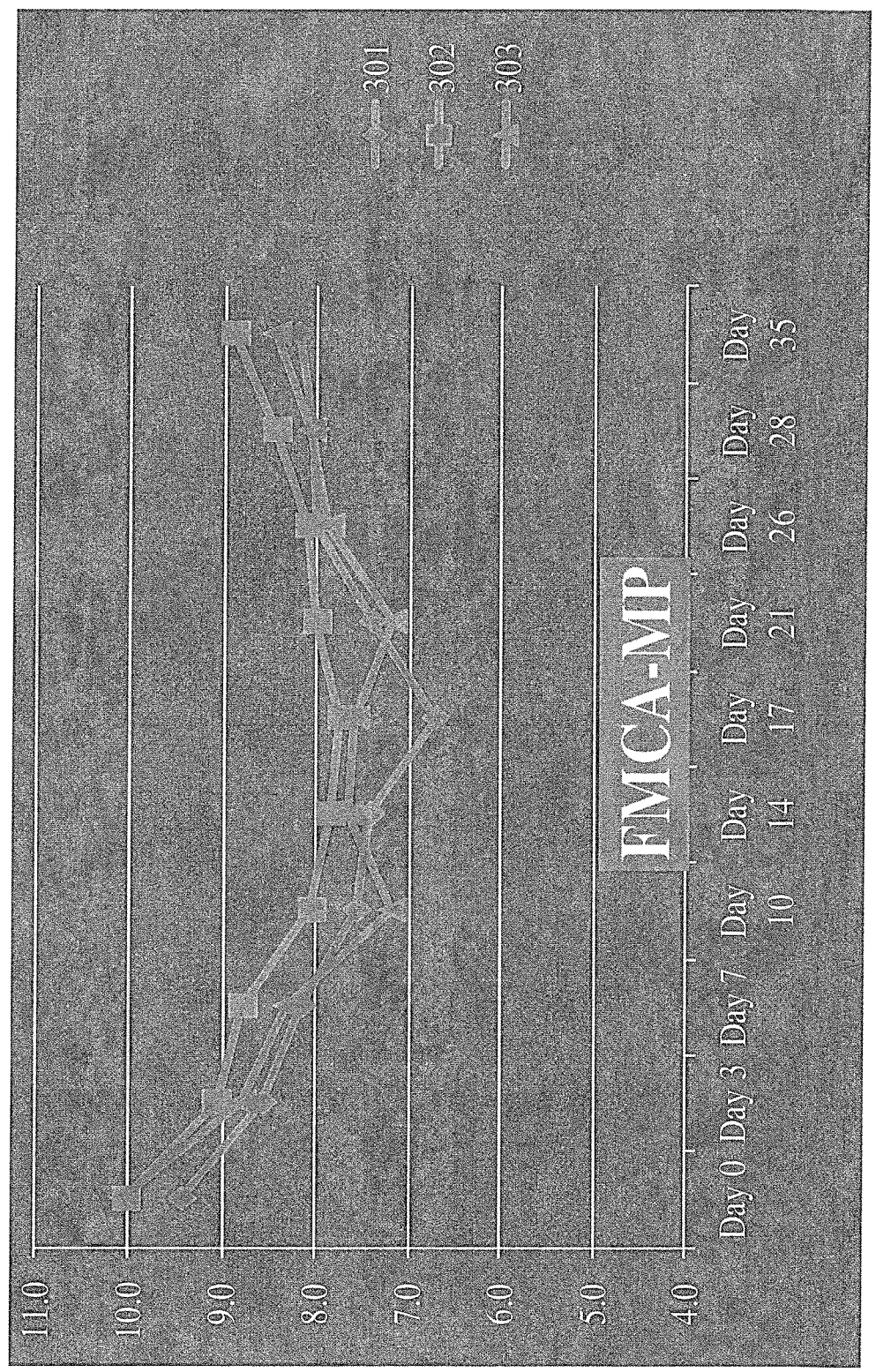

FIG. 15 shows that the FMCA monophosphate prodrug (Compound 15P/18P as per FIG. 8) is active against wild-type HBV with 2 log viral load down.

Figure 16A:
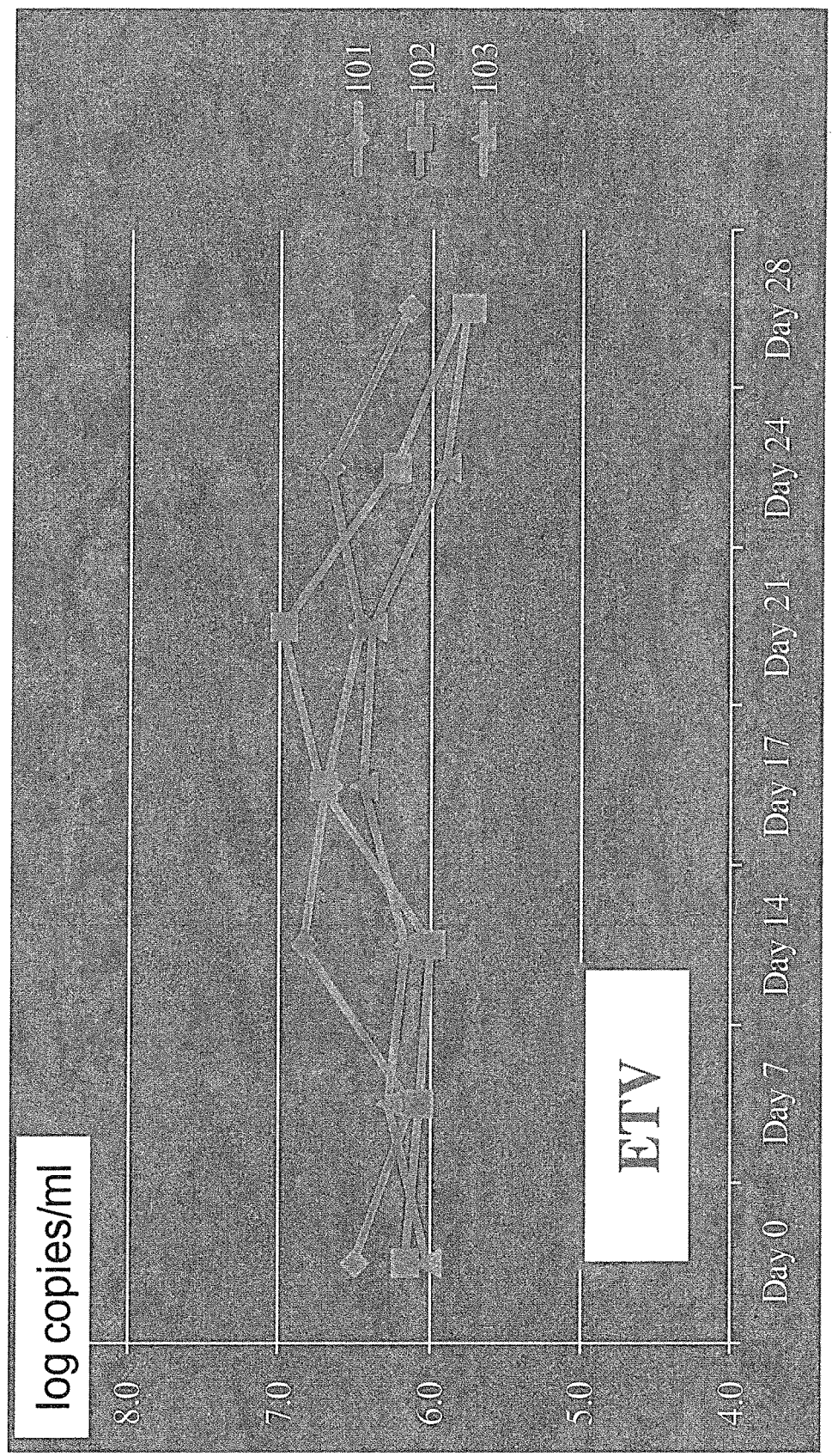

FIG. 16A shows that ETV (entecavir) is not active against entecavir resistant HBV mutant ((L180M+M204V+S202G).

Figure 16B:
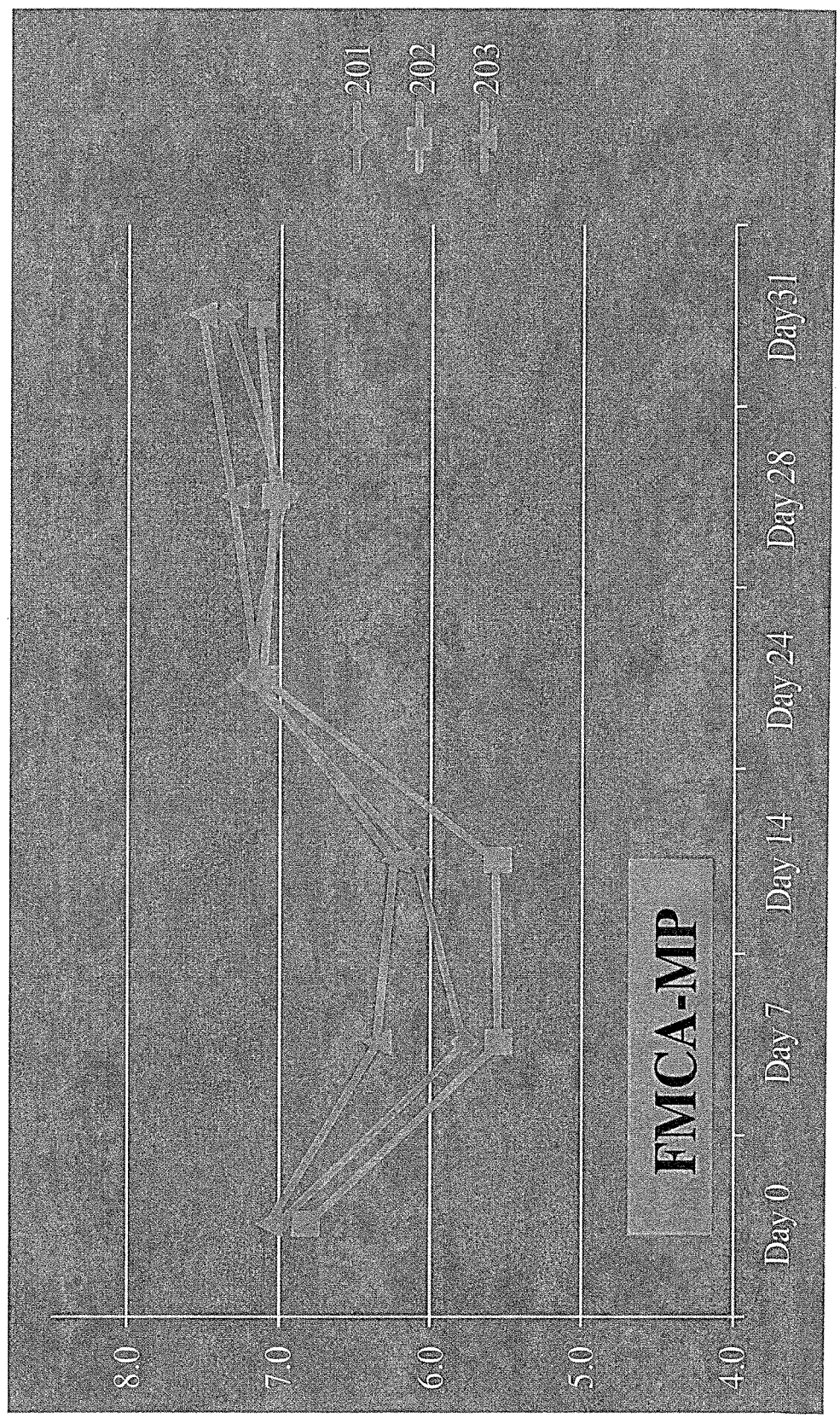

FIG. 16B shows that FMCA monophosphate prodrug (Compound 15P/'8P as per FIG. 8) is active against entecavir resistant HBV mutant (L180M+M204V+S202G) with 1 log viral load down.

BRIEF DESCRIPTION OF THE INVENTION

The present invention relates to carbocyclic nucleoside compounds according to the structure:

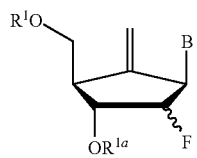

Where B is

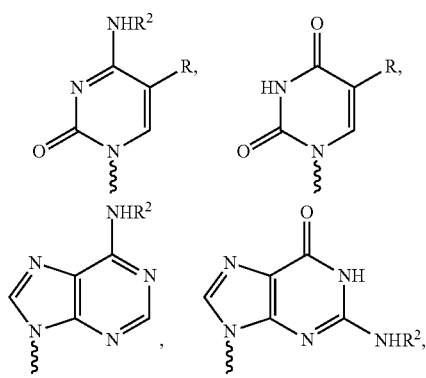

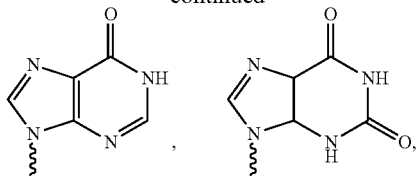

Wherein R is H, F, Cl, Br, I, $C_1$-$C_4$ alkyl (preferably $CH_3$), —C≡N, —C≡C—$R_a$,

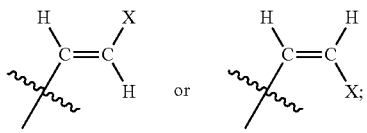

X is H, $C_1$-$C_4$ alkyl (preferably, $CH_3$), F, Cl, Br or I;
$R_q$ is H or a —$C_1$-$C_4$ alkyl group;
$R^1$ and $R^{1a}$ are each independently, H, an acyl group, a $C_1$-$C_{20}$ alkyl or ether group, an amino acid residue (D or L), a phosphate, diphosphate, triphosphate, phosphodiester or phosphoramidate group or together $R^1$ and $R^{1a}$ form a carbodiester, phosphodiester or phosphoramidate group with the oxygen atoms to which they are bonded;
$R^2$ is H, an acyl group, a $C_1$-$C_{20}$ alkyl or ether group or an amino acid residue (D or L);
Or a pharmaceutically acceptable salt, enantiomer, hydrate or solvate thererof.

Preferably $R^{1a}$ is H. Also preferably, $R^1$ and $R^2$ are each independently H or a $C_2$-$C_{20}$ acyl group, more preferably both are H. In certain aspects $R^1$ is a phosphoramidate group.
B is preferably

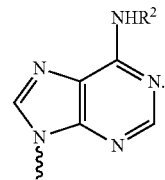

In alternative preferred aspects, the compound is represented by the chemical structure:

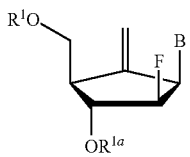

Where B is as described above, preferably

and $R^1$, $R^{1a}$ and $R^2$ are as otherwise described hereinabove. Note that the fluoro group at the 2' position (which may be disposed in an alpha or beta (up or down) configuration in compounds according to the present invention) is preferably disposed in a beta (upward) configuration as depicted. Preferred compounds according to the present invention are prodrug forms where $R^{1a}$ is a phosphoramidate group as otherwise described herein, preferably a phosphoramidate group derived from an amino acid as otherwise described herein. In certain aspects, a particularly preferred $R^1$ group is the phosphoramidate group

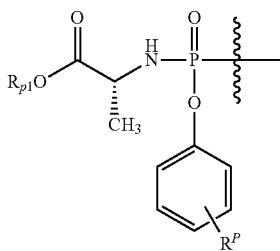

Where $R_{p1}$ is an optionally substituted (i.e., with eg., OH, halo) $C_1$-$C_{20}$ alkyl group, preferably a $C_1$-$C_4$ alkyl group, even more preferably a methyl, ethyl, isopropyl group or isobutyl group; and
$R^P$ is H, nitro, cyano, methoxy, or a $C_1$-$C_3$ alkyl group optionally substituted with from 1-3 halogen substituents (preferably F). The present invention is also directed to individual diastereomers based upon the phosphoramidate group as otherwise described herein (phosphorous is a chiral center).

Preferred phosphoramidate groups for $R^1$ include those according to the chemical structure:

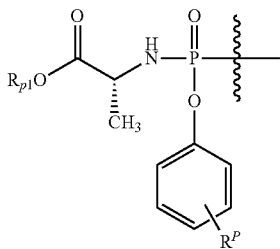

Where $R^P$ is H or $C_1$-$C_3$ alkyl group and $R_{p1}$ is methyl, ethyl, isopropyl or isobutyl, more preferably a methyl or isopropyl group.
Preferably, $R^1$ is a

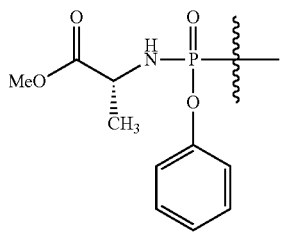 [SMILES: *P(=O)(N[C@H](C)C(=O)OC)Oc1ccccc1]

group.
In particularly preferred aspects of the invention, the anti-HBV compound for use in the present invention is

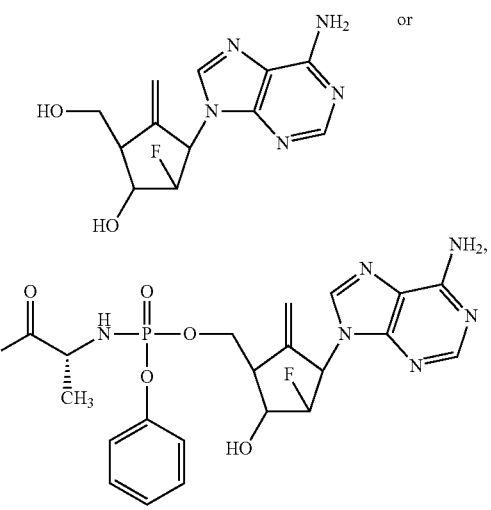

Or a pharmaceutically acceptable salt thereof.

The present invention also relates to pharmaceutical compositions comprising an effective amount of a compound as described above, optionally in combination with a pharmaceutically acceptable carrier, additive or excipient. Alternative embodiments of pharmaceutical compositions comprise an effective amount of a carbocyclic nucleoside compound as otherwise described herein in combination with an additional antiviral agent. Preferred antiviral agents include, for example acyclovir, famciclovir, ganciclovir, valaciclovir, vidaribine, ribavirin, zoster-immune globulin (ZIG), lamivudine, adefovir dipivoxil, entecavir, telbivudine, clevudine, tenofovir and mixtures thereof. Particularly preferred compounds for use in the pharmaceutical aspect of the present invention include

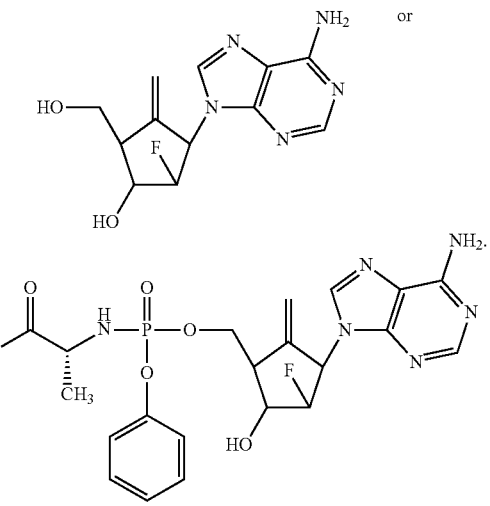

Or a pharmaceutically acceptable salt thereof.

Methods of treatment represent further embodiments according to the present invention. In this aspect a method of treating or reducing the likelihood of a viral infection, wherein the viral infection is caused by Hepatitis B virus (HBV), Hepatitis C virus (HCV), Herpex Simplex I (HSV I), Herpes Simplex II (HSV II), Cytomegalovirusx (CMV), Varicella Zoster Virus (VZV) or Epstein Barr Virus (EBV), comprises administering to a patient in need of therapy or at risk for infection thereof an effective amount of a compound as otherwise described above.

In method aspects of the present invention, preferred compounds for use in the present to treat HBV include:

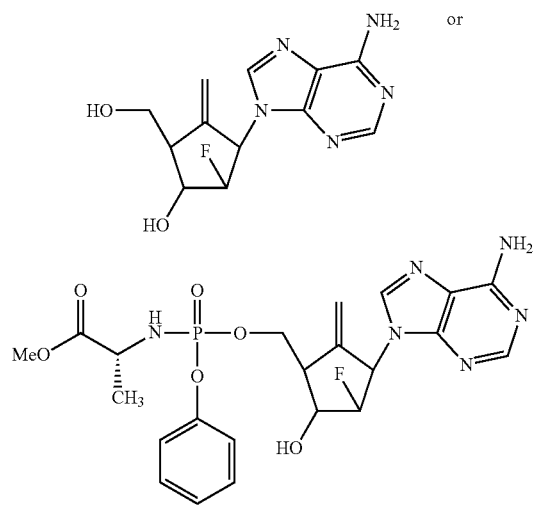

Or a pharmaceutically acceptable salt thereof.

In a preferred method, the present invention relates to a method of treating a HBV infection, including a drug resistant (further including multiple drug resistant) HBV infection, wherein the drug resistance is to any one or more of currently used anti-HBV agents, including adefovir, entecavir and/or lamivudine drug resistance, especially including strains resistant to lamivudine and entecavir, lamivudine and adefovir, entecavir and limuvidine and lamivudine, entecare and adefovir, among others. In this aspect of the invention, preferred compounds for use in the present method to treat a HBV infection, especially including a drug resistant (including a multiple drug resistant as described hereinabove) HBV infection include:

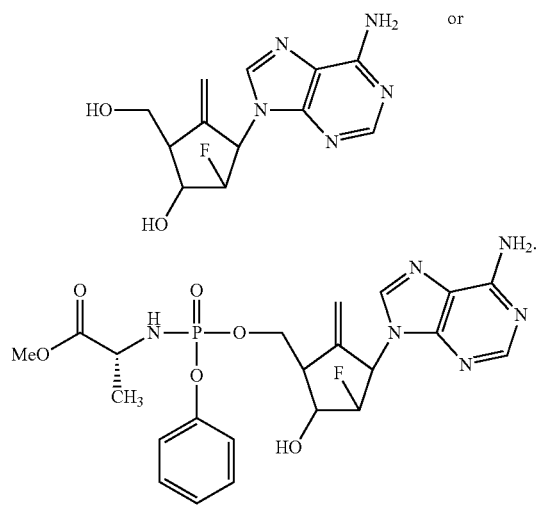

Or a pharmaceutically acceptable salt thereof.

Combination therapy using the present compounds in combination with an additional antiviral agent represent additional aspects of the present invention. Preferred antiviral agents include, for example acyclovir, famciclovir, ganciclovir, valaciclovir, vidaribine, ribavirin, zoster-immune globulin (ZIG), lamivudine, adefovir dipivoxil, entecavir, telbivudine, clevudine, tenofovir and mixtures thereof, including other agents as otherwise described herein. Methods of treating or reducing the likelihood of the development of fibrosis, liver cancer or cirrhosis secondary to a viral infection, including a drug resistant viral infection (especially including HBV and/or HCV) represent additional aspects of the present invention. The use of the following compounds (including their diasteromerically enriched and/or diastereomerically pure compounds) in certain aspects of combination therapy for the treatment of a HBV infection, especially including a drug resistant (including a multiple drug resistant as otherwise described herein) strain of HBV, are particularly preferred:

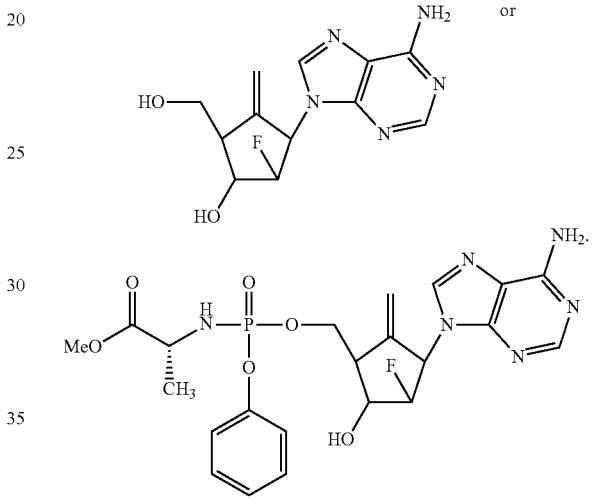

Or a pharmaceutically acceptable salt thereof in combination with any one or more additional anti-HBV agents as otherwise described herein.

DETAILED DESCRIPTION OF THE INVENTION

The following definitions are used to describe the invention. If a term is not specifically defined herein, the meaning given to the term is that which one of ordinary skill would apply to the term within the context of the term's use.

The term "compound", as used herein, unless otherwise indicated, refers to any specific chemical compound disclosed herein, generally refers to β-D nucleoside analogs, but may include, within context, tautomers, regioisomers, geometric isomers, anomers, and where applicable, optical isomers (enantiomers) or diastereomers (two chiral centers) thereof of these compounds, as well as pharmaceutically acceptable salts thereof, solvates and/or polymorphs thereof. Within its use in context, the term compound generally refers to a single compound, but also may include other compounds such as stereoisomers, regioisomers and/or optical isomers (including racemic mixtures and/or diastereomers as described herein) as well as specific enantiomers, enantiomerically enriched or individual diastereomers or mixtures of disclosed compounds. It is noted that in the event that a carbon range is provided for a compound, that range signifies that each and every carbon individually is considered part of the range. For example a $C_1$-$C_{20}$ group describes a group with a single carbon, two carbon atoms, three carbon atoms, four carbon atoms, etc. up to twenty carbons.

The term "patient" or "subject" is used throughout the specification to describe an animal, preferably a domesticated animal especially including a mammal or a human, more preferably a human to whom treatment, including prophylactic treatment, with the compositions according to the present invention is provided. For treatment of those infections, conditions or disease states which are specific for a specific animal such as a human patient, the term patient refers to that specific animal. In general, in the present invention, the term patient refers to a human patient unless otherwise stated. In the present invention, in addition to humans, domesticated animals (e.g., horses, cows, pigs, sheep, gtoats, dogs, cats, etc.) also may be commonly treated.

The term "Hepatitis B virus" or "HBV" is used to describe a virus which infects the liver of hominoidae, including humans, and causes an inflammation called hepatitis. Originally known as "serum hepatitis", the disease has caused epidemics in parts of Asia and Africa, and it is endemic in China. About a third of the world's population, more than 2 billion people, have been infected with the hepatitis B virus. This includes 350 million chronic carriers of the virus. Transmission of hepatitis B virus results from exposure to infectious blood or body fluids containing blood. The acute illness causes liver inflammation, vomiting, jaundice and—rarely—death. Chronic hepatitis B may eventually cause liver cirrhosis and liver cancer—a fatal disease with very poor response to current chemotherapy.

Hepatitis B virus is an hepadnavirus—hepa from hepatotrophic and dna because it is a DNA virus and it has a circular genome composed of partially double-stranded DNA. The viruses replicate through an RNA intermediate form by reverse transcription, and in this respect they are similar to retroviruses. Although replication takes place in the liver, the virus spreads to the blood where virus-specific proteins and their corresponding antibodies are found in infected people. Blood tests for these proteins and antibodies are used to diagnose the infection.

Cirrhosis of the liver and liver cancer may ensue from a Hepatitis B virus infection. The hepatitis B virus primarily interferes with the functions of the liver by replicating in liver cells, known as hepatocytes. The primary method of transmission reflects the prevalence of chronic HBV infection in a given area. In low prevalence areas such as the continental United States and Western Europe, where less than 2% of the population is chronically infected, injection drug abuse and unprotected sex are the primary methods, although other factors may be important. In moderate prevalence areas, which include Eastern Europe, Russia, and Japan, where 2-7% of the population is chronically infected, the disease is predominantly spread among children. In high prevalence areas such as China and South East Asia, transmission during childbirth is most common, although in other areas such as Africa, transmission during childhood is a significant factor. The prevalence of chronic HBV infection in certain areas may be at least 8%.

Transmission of hepatitis B virus results from exposure to infectious blood or body fluids containing blood. Possible forms of transmission include (but are not limited to) unprotected sexual contact, blood transfusions, re-use of contaminated needles & syringes, and vertical transmission from mother to child during childbirth.

Compounds which have been shown to be useful in the treatment and/or inhibition of HBV infections and which may be combined with 2'-fluoronucleoside compounds according to the present invention for the treatment of HBV infections include, for example, Hepsera (adefovir dipivoxil), lamivudine, entecavir, telbivudine, tenofovir, emtricitabine, clevudine, valtoricitabine, amdoxovir, pradefovir, racivir, BAM 205, nitazoxanide, UT 231-B, Bay 41-4109, EHT899, zadaxin (thymosin alpha-1), and mixtures thereof. The term "drug resistant" or "drug resistant mutants" of HBV includes all strains of HBV which are resistant to one or more (including multiple drug resistant strains) of the above-referenced anti-HBV agents, especially including one or more of lamivudine, adefovir and entecavir. These strains include, for example, HBV strains rtM204V, rtM204I, rtL180M, rtLM/rtMV (which is a double mutant of rt180M/rtM204V), rtN236T, L180M+S02I+M202V (an entecavir mutant), among others. The present compounds are useful against all types of drug resistant HBV strains, including multiple drug resistant strains.

The term "Hepatitis C virus" or "HCV" is used to describe a virus which causes a Hepatitis C infection, which is an infectious disease of the liver. The infection is often asymptomatic, but once established, chronic infection can progress to scarring of the liver (fibrosis), and advanced scarring (cirrhosis) which is generally apparent after many years. In some cases, those with cirrhosis will go on to develop liver failure or other complications of cirrhosis, including liver cancer.

The hepatitis C virus (HCV) is spread by blood-to-blood contact. Most people have few, if any symptoms after the initial infection, yet the virus persists in the liver in about 85% of those infected. Those who develop cirrhosis or liver cancer may require a liver transplant, and the virus universally recurs after transplantation.

An estimated 270-300 million people worldwide are infected with hepatitis C. Hepatitis C is a strictly human disease. It cannot be contracted from or given to any animal, although experiments on chimpanzees are possible. Acute hepatitis C refers to the first 6 months after infection with HCV. Between 60% and 70% of people infected develop no symptoms during the acute phase. In the minority of patients who experience acute phase symptoms, they are generally mild and nonspecific, and rarely lead to a specific diagnosis of hepatitis C. Symptoms of acute hepatitis C infection include decreased appetite, fatigue, abdominal pain, jaundice, itching, and flu-like symptoms. Hepatitis C virus is usually detectable in the blood within one to three weeks after infection by PCR, and antibodies to the virus are generally detectable within 3 to 15 weeks. Spontaneous viral clearance rates are highly variable and between 10-60% of persons infected with HCV clear the virus from their bodies during the acute phase as shown by normalization in liver enzymes (alanine transaminase (ALT) & aspartate transaminase (AST)), and plasma HCV-RNA clearance (this is known as spontaneous viral clearance). However, persistent infections are common and most patients develop chronic hepatitis C, i.e., infection lasting more than 6 months. Previous practice was to not treat acute infections to see if the person would spontaneously clear; recent studies have shown that treatment during the acute phase of genotype 1 infections has a greater than 90% success rate with half the treatment time required for chronic infections.

Chronic hepatitis C is defined as infection with the hepatitis C virus persisting for more than six months. Clinically, it is often asymptomatic (without symptoms) and it is mostly discovered accidentally. The natural course of chronic hepatitis C varies considerably from one person to another. Although almost all people infected with HCV have evidence of inflammation on liver biopsy, the rate of progression of liver scarring (fibrosis) shows significant variability among individuals. Accurate estimates of the risk over time are difficult to establish because of the limited time that tests for this virus have been available. Recent data suggest that among untreated patients, roughly one-third progress to liver cirrhosis in less than 20 years. Another third progress to cirrhosis within 30 years. The remainder of patients appear to progress so slowly that they are unlikely to develop cirrhosis within their lifetimes. In contrast the NIH consensus guidelines state that the risk of progression to cirrhosis over a 20-year period is 3-20 percent.

Factors that have been reported to influence the rate of HCV disease progression include age (increasing age associated with more rapid progression), gender (males have more rapid disease progression than females), alcohol consumption (associated with an increased rate of disease progression), HIV coinfection (associated with a markedly increased rate of disease progression), and fatty liver (the presence of fat in liver cells has been associated with an increased rate of disease progression).

Symptoms specifically suggestive of liver disease are typically absent until substantial scarring of the liver has occurred. However, hepatitis C is a systemic disease and patients may experience a wide spectrum of clinical manifestations ranging from an absence of symptoms to a more symptomatic illness prior to the development of advanced liver disease. Generalized signs and symptoms associated with chronic hepatitis C include fatigue, flu-like symptoms, joint pains, itching, sleep disturbances, appetite changes, nausea, and depression.

Once chronic hepatitis C has progressed to cirrhosis, signs and symptoms may appear that are generally caused by either decreased liver function or increased pressure in the liver circulation, a condition known as portal hypertension. Possible signs and symptoms of liver cirrhosis include ascites (accumulation of fluid in the abdomen), bruising and bleeding tendency, varices (enlarged veins, especially in the stomach and esophagus), jaundice, and a syndrome of cognitive impairment known as hepatic encephalopathy. Hepatic encephalopathy is due to the accumulation of ammonia and other substances normally cleared by a healthy liver.

Hepatitis C infection livers show variable elevation of ALT and AST in liver tests. Periodically they might show normal results. Usually prothrombin and albumin results are normal, but may become abnormal, once cirrhosis has developed. The level of elevation of liver tests do not correlate well with the amount of liver injury on biopsy. Viral genotype and viral load also do not correlate with the amount of liver injury. Liver biopsy is the best test to determine the amount of scarring and inflammation. Radiographic studies such as ultrasound or CT scan do not always show liver injury until it is fairly advanced. However, non-invasive tests (blood sample) are coming, with FibroTest and ActiTest, respectively estimating liver fibrosis and necrotico-inflammatory. These tests are validated and recommended in Europe (FDA procedures initiated in USA).

Chronic hepatitis C, more than other forms of hepatitis, can be associated with extrahepatic manifestations associated with the presence of HCV such as porphyria cutanea tarda, cryoglobulinemia (a form of small-vessel vasculitis) and glomerulonephritis (inflammation of the kidney), specifically membranoproliferative glomerulonephritis (MPGN). Hepatitis C is also rarely associated with sicca syndrome (an autoimmune disorder), thrombocytopenia, lichen planus, diabetes mellitus and with B-cell lymphoproliferative disorders.

Compounds which have been shown to be useful in the treatment and/or inhibition of HCV infections and which may be combined with 2'-fluoronucleoside compounds according to the present invention for the treatment of HCV infections include, for example, NM 283, ribavirin, VX-950 (telaprevir), SCH 50304, TMC435, VX-500, BX-813, SCH503034, R1626, ITMN-191 (R7227), R7128, PF-868554, TT033, CGH-759, GI 5005, MK-7009, SIRNA-034, MK-0608, A-837093, GS 9190, ACH-1095, GSK625433, TG4040 (MVA-HCV), A-831, F351, NS5A, NS4B, ANA598, A-689, GNI-104, IDX102, ADX184, GL59728, GL60667, PSI-7851, TLR9Agonist, PHX1766, SP-30 and mixtures thereof, and other antiviral compounds as identified herein.

The term "Herpes simplex virus", "Herpes simplex virus-1" (HSV-1), "Herpes simplex virus-2" (HSV-2), are two species of the herpes virus family, Herpesviridae, which cause infections in humans. As with other herpesviridae, herpes simplex virus may produce life-long infections. They are also called Human Herpes Virus 1 and 2 (HHV-1 and HHV-2) and are neurotropic and neuroinvasive viruses; they enter and hide in the human nervous system, accounting for their durability in the human body. HSV-1 is commonly associated with herpes outbreaks of the face known as cold sores or fever blisters, whereas HSV-2 is more often associated with genital herpes, although each of the two strains of HSV may be found in areas normally associated with the other strain.

An infection by a herpes simplex virus is marked by watery blisters in the skin or mucous membranes of the mouth, lips or genitals. Lesions heal with a scab characteristic of herpetic disease. However, the infection is persistent and symptoms may recur periodically as outbreaks of sores near ear the site of original infection. After the initial, or primary, infection, HSV becomes latent in the cell bodies of nerves in the area. Some infected people experience sporadic episodes of viral reactivation, followed by transportation of the virus via the nerve's axon to the skin, where virus replication and shedding occurs. Herpes is contagious if the carrier is producing and shedding the virus. This is especially likely during an outbreak but possible at other times. There is no cure yet, but there are treatments which reduce the likelihood of viral shedding.

The terms "cytomegalovirus", "CMV" human cytomegalovirus, "HCMV" are used to describe a herpes viral genus of the Herpesviruses group: in humans it is also commonly known as HCMV or Human Herpesvirus 5 (HHV-5). CMV belongs to the Betaherpesvirinae subfamily of Herpesviridae, which also includes Roseolovirus. Other herpesviruses fall into the subfamilies of Alphaherpesvirinae (including HSV 1 and 2 and varicella) or Gammaherpesvirinae (including Epstein-Barr virus)[1] All herpesviruses share a characteristic ability to remain latent within the body over long periods.

HCMV infections are frequently associated with salivary glands, though they may be found throughout the body. HCMV infection can also be life threatening for patients who are immunocompromised (e.g. patients with HIV, organ transplant recipients, or neonates). Other CMV viruses are found in several mammal species, but species isolated from animals differ from HCMV in terms of genomic structure, and have not been reported to cause human disease.

HCMV is found throughout all geographic locations and socioeconomic groups, and infects between 50% and 80% of adults in the United States (40% worldwide) as indicated by the presence of antibodies in much of the general population. Seroprevalence is age-dependent: 58.9% of individuals aged 6 and older are infected with CMV while 90.8% of individuals aged 80 and older are positive for HCMV. HCMV is also the virus most frequently transmitted to a developing fetus. HCMV infection is more widespread in developing countries and in communities with lower socioeconomic status and represents the most significant viral cause of birth defects in industrialized countries.

Most healthy people who are infected by HCMV after birth have no symptoms. Some of them develop an infectious mononucleosis/glandular fever-like syndrome, with prolonged fever, and a mild hepatitis. A sore throat is common. After infection, the virus remains latent in the body for the rest of the person's life. Overt disease rarely occurs unless immunity is suppressed either by drugs, infection or old-age. Initial HCMV infection, which often is asymptomatic is followed by a prolonged, inapparent infection during which the virus resides in cells without causing detectable damage or clinical illness.

Infectious CMV may be shed in the bodily fluids of any infected person, and can be found in urine, saliva, blood, tears, semen, and breast milk. The shedding of virus can occur intermittently, without any detectable signs or symptoms.

The term "Varicella Zoster virus" or "VZV" is used to describe one of eight herpes viruses known to infect humans (and other vertebrates). VZV commonly causes chicken-pox in children and both shingles and postherpetic neuralgia in adults. Varicella-zoster virus is known by many names, including: chickenpox virus, varicella virus, zoster virus, and human herpes virus type 3 (HHV-3). Primary VZV infection results in chickenpox (varicella), which may rarely result in complications including encephalitis or pneumonia. Even when clinical symptoms of chickenpox have resolved, VZV remains dormant in the nervous system of the infected person (virus latency), in the trigeminal and dorsal root ganglia. In about 10-20% of cases, VZV reactivates later in life producing a disease known as herpes zoster or shingles. Serious complications of shingles include postherpetic neuralgia, zoster multiplex, myelitis, herpes ophthalmicus, or zoster sine herpete.

VZV is closely related to the herpes simplex viruses (HSV), sharing much genome homology. Many of the known envelope glycoproteins of VZV correspond with those in HSV. VZV, unlike HSV, fails to produce the LAT (latency-associated transcripts) that play an important role in establishing HSV latency (herpes simplex virus). The virus is very susceptible to disinfectants, notably sodium hypochlorite. Within the human body, along with compounds of the present invention, it can be treated by a number of drugs and therapeutic agents including acyclovir, zoster-immune globulin (ZIG), and vidarabine.

The term "Epstein Barr virus" or "EBV", also called Human herpesvirus 4 (HHV-4), is a virus of the herpes family and is one of the most common viruses in humans. Most people become infected with EBV, which is often asymptomatic, but infection commonly causes infectious mononucleosis (also known as glandular fever). Epstein-Barr virus occurs worldwide. Most people become infected with EBV sometime during their lives, and therefore gain adaptive immunity, preventing repeated sickness from re-infection through EBV antibodies. In the United States, as many as 95% of adults between 35 and 40 years of age have been infected. Infants become susceptible to EBV as soon as maternal antibody protection (present at birth) disappears. When infection with EBV occurs during adolescence or young adulthood, it causes infectious mononucleosis 35% to 69% of the time.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Representative cancers include, for example, stomach, colon, rectal, liver, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, leukemia, melanoma, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, nasopharyngeal, oesophagus, larynx, kidney cancer and lymphoma, among others, which may be treated by one or more compounds according to the present invention. In certain aspects of the invention, the term tumor or cancer refers to hepatocellular cancer, lymphoma, Burkitt's lymphoma, Hodgkin's lymphoma and nasopharyngeal cancer, which are cancers which frequently occur secondary to hepatitis B virus (HBV), hepatitis C virus (HCV) and/or Epstein-Barr virus (EBV) infections.

The term "tumor" is used to describe a malignant or benign growth or tumefacent.

The term "anti-cancer compound" or "anti-cancer agent" is used to describe any compound which may be used to treat cancer. Anti-cancer compounds for use in the present invention may be co-administered with one or more of the compounds according to the present invention to treat cancer which occurs in the presence of a viral infection or secondary to a viral infection. Exemplary anti-cancer compounds for use in the present invention for co-administration with compounds according to the present invention include a number of compounds which are broadly characterized as antimetabolites, inhibitors of topoisomerase I and II, alkylating agents and microtubule inhibitors (e.g., taxol). Anti-cancer compounds for use in the present invention include, for example, Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gleevac, gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolacetone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and mixtures thereof, among others.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids well known in the pharmaceutical art. Sodium and potassium salts are particularly preferred as neutralization salts of the phosphates according to the present invention.

The term "pharmaceutically acceptable derivative" is used throughout the specification to describe any pharmaceutically acceptable prodrug form (such as an ester, ether or amide or other prodrug group) which, upon administration to a patient, provides directly or indirectly the present compound or an active metabolite of the present compound.

The term "alkyl" shall mean within its context a $C_1$-$C_{20}$, preferably a $C_1$-$C_{10}$ linear, branch-chained or cyclic fully saturated hydrocarbon radical, which may be optionally substituted. It is noted that in the event that a carbon range is provided, that range signifies that each and every carbon is considered part of the range. For example a $C_1$-$C_{20}$ group describes a group with a single carbon, two carbon atoms, three carbon atoms, four carbon atoms, etc. The term "ether" shall mean an optionally substituted $C_1$ to $C_{20}$ ether group, formed from an oxygen and an alkyl group, or alternatively, may also contain at least one oxygen within the alkyl or alkylene chain.

The term "aromatic" or "aryl" shall mean within its context a substituted or unsubstituted monovalent carbocyclic aromatic radical having a single ring (e.g., phenyl) or multiple condensed rings (e.g., naphthyl, anthracene, phenanthrene). Other examples include optionally substituted heterocyclic aromatic ring groups ("heteroaromatic" or "heteroaryl") having one or more nitrogen, oxygen, or sulfur atoms in the ring, and preferably include five or six-membered heteroaryl groups, such as imidazole, furyl, pyrrole, furanyl, thiene, thiazole, pyridine, pyrazine, triazole, oxazole, among others, but can also include fused ring heteroaryl groups such as indole groups, among others. The preferred aryl group in compounds according to the present invention is a phenyl or a substituted phenyl group.

The term "heterocycle" shall mean an optionally substituted moiety which is cyclic and contains at least one atom other than a carbon atom, such as a nitrogen, sulfur, oxygen or other atom, which ring may be saturated and/or unsaturated.

The term "unsubstituted" shall mean substituted only with hydrogen atoms. The term "substituted" shall mean, within the chemical context of the compound defined, a substituent (each of which substituent may itself be substituted) selected from a hydrocarbyl (which may be substituted itself, preferably with an optionally substituted alkyl or fluoro group, among others), preferably an alkyl (generally, no greater than about 3 carbon units in length), including $CF_3$, an optionally substituted aryl, halogen (F, Cl, Br, I), thiol, hydroxyl, carboxyl, $C_1$-$C_3$ alkoxy, alkoxycarbonyl, CN, nitro or an optionally substituted amine (e.g. an alkyleneamine or a $C_1$-$C_3$ monoalkyl or dialkyl amine). Various optionally substituted moieties may be substituted with 3 or more substituents, preferably no more than 3 substituents and preferably with 1 or 2 substituents.

The term "acyl" is used throughout the specification to describe a group at the 5' or 3' position of the nucleoside analog (i.e., at the free hydroxyl position in the carbocyclic moiety) or on the exocyclic amine of the nucleoside base which contains a $C_1$ to $C_{20}$ linear, branched or cyclic alkyl chain. The acyl group in combination with the hydroxyl group results in an ester and the acyl group in combination with an exocyclic amine group results in an amide, which, after administration, may be cleaved to produce the free nucleoside form of the present invention. Acyl groups according to the present invention are represented by the structure:

where $R^4$ is a $C_1$ to $C_{20}$ linear, branched or cyclic alkyl group which is optionally substituted preferably with, for example, 1-3 hydroxyl groups, 1-3 halo groups (F, Cl, Br, I) or an amine group (which itself may be optionally substituted with one or two $C_1$-$C_6$ alkyl groups optionally bearing between 1 and 3 hydroxyl groups), alkoxyalkyl (including an ethylene oxide chain which may end in a free hydroxyl group or a $C_1$-$C_{10}$ alkyl group and ranges in molecular weight from about 50 to about 40,000 or about 200 to about 5,000), such as phenoxymethyl, aryl, alkoxy, alkoxycarbonyloxy groups (e.g., [(isopropoxycarbonyl)oxy]-methoxy), aryloxyalkyl, among others, all of which groups may be optionally substituted, as described above. Preferred acyl groups are those where $R^4$ is a $C_1$ to $C_{12}$ alkyl group. Acyl groups according to the present invention also include, for example, those acyl groups derived from benzoic acid and related acids, 3-chlorobenzoic acid, succinic, capric and caproic, lauric, myristic, palmitic, stearic and oleic groups, among numerous others and may include such related groups as sulfone groups such as mesylate groups. All groups may be appropriatedly substituted within context as otherwise described herein. One of ordinary skill in the art will recognize the acyl groups which will have utility in the present invention, either to synthesize the target pharmaceutical compounds or as prodrug of the nucleosides according to the present invention.

The term "amino acid" or "amino acid residue" shall mean, within context, a radical of a D- or L-amino acid which is covalently bound to a nucleoside analog at the 4' exocyclic amine position of the cytosine base or the 5'- or 3'-OH position of the sugar synthon ($R^2$, $R^1$ or $R^{1\alpha}$) through a carboxylic acid moiety of the amino acid, thus forming respectively, an amide or ester group linking the nucleoside to the amino acid. Amino acids may also be used to provide phosphoramidate groups in nucleoside compounds according to the present invention as otherwise described herein. Representative amino acids include both natural and unnatural amino acids, preferably including, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine, among others.

The term "phosphate ester" or "phosphodiester" (which term includes phosphotriester groups and phosphoramidate groups in context) is used throughout the specification to describe mono-phosphate groups formed at the 5' position of the carbocyclic sugar synthon which are mono- or diesterified (or amidated and optionally esterified in the case of a phosphoramidate) such that the phosphate group is negatively charged or is rendered neutral, i.e., has a neutral charge. Phosphate esters, phosphodiesters and/or phosphoramidate groups for use in the present invention include those represented by the structures:

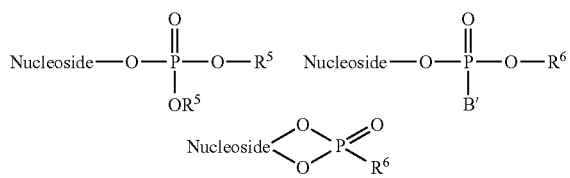

where each $R^5$ and $R^6$ is independently selected from H, a $C_1$ to $C_{20}$ linear, branched or cyclic alkyl group, alkoxyalkyl, aryloxyalkyl, such as phenoxymethyl, optionally substituted aryl (especially an optionallyl substituted phenyl group) and alkoxy, among others, including alkoxycarbonyloxy groups (e.g., (isopropoxycarbonyl)oxy]-methoxy) each of which groups may be optionally substituted (e.g., a phenyl or other group may be optionally substituted as otherwise described herein or preferably with from one to three, $C_1$-$C_6$ alkyl groups, halogen, preferably F, Cl or Br, nitro, cyano, or $C_2$-$C_6$ carboxyester groups) with the proviso that at least one $R^5$ group is other than H, or the two $R^5$ groups together form a five- or six-membered heterocyclic group;

B' is a

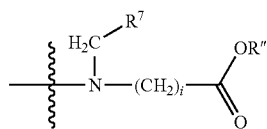

group or a group obtained from an amino acid (a natural or unnatural amino acid such as, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine, among others) to preferably provide a group according to the structure

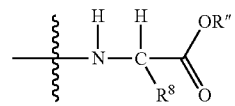

Where i is 0, 1, 2 or 3 (preferably 0)

$R^7$ is a $C_1$ to $C_{20}$ linear, branched or cyclic alkyl or acyl group, alkoxyalkyl, aryloxyalkyl, such as phenoxymethyl, optionally substituted aryl group (as described above) and alkoxy, among others, each of which groups may be optionally substituted;

$R^8$ is sidechain of an amino acid, preferably a sidechain of an amino acid selected from the group consisting of alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine (preferably $R^8$ is derived from alanine, leucine, isoleucine or threonine, more preferably alanine-$R^8$ is methyl), and R" is a $C_1$ to $C_{20}$ linear, branched or cyclic alkyl or a phenyl or heteroaryl group, each of which groups is optionally substituted.

Preferred monophosphate esters for use in prodrug forms according to the present invention are those where $R^5$ is a $C_1$ to $C_{20}$ linear or branched chain alkyl group, more preferably a $C_1$ to $C_3$ alkyl group, all of which groups may be optionally substituted. Other compounds which are preferred are as otherwise set forth herein, especially, where $R^1$ is a phosphoramidate group as otherwise described herein. A preferred phosphoramidate is

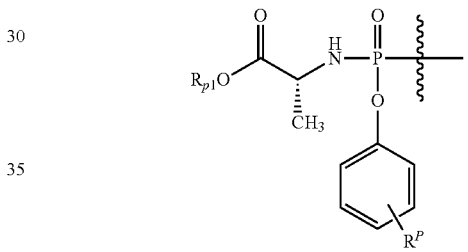

Where $R_{p1}$ is an optionally substituted (OH, halo) $C_1$-$C_{20}$ alkyl group, preferably a $C_1$-$C_4$ alkyl group, even more preferably a methyl, ethyl, isopropyl group or isobutyl group; and $R^P$ is H, nitro, cyano, methoxy, or a $C_1$-$C_3$ alkyl group optionally substituted with from 1-3 halogen substituents (preferably F).

Preferred phosphoramidate groups for $R^1$ include those according to the chemical structure:

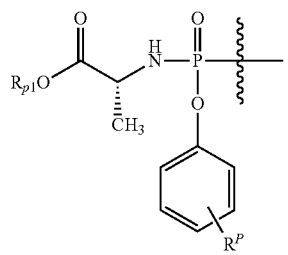

Where $R^P$ is H or $C_1$-$C_3$ alkyl group (preferably H) and $R_{p1}$ is methyl, ethyl, isopropyl or isobutyl group, more preferably a methyl or isopropyl group.

In other embodiments $R^1$ is a

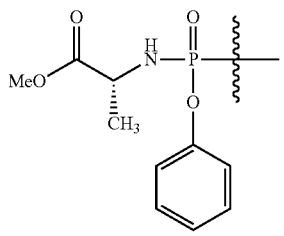

group.

The term "effective amount" shall mean an amount or concentration of a compound according to the present invention which is effective within the context of its administration or use, which may be inhibitory, prophylactic and/or therapeutic. Within context, all active compounds which are used in the present invention are used in effective amounts. The present compound also relates to combinations of compounds which contain effective amounts of each of the compounds used, whether that combination is additive or synergistic in effect, provided that the overall effect of the combination of compounds is to inhibit the growth, reduce the likelihood of or treat viral infections in patients as otherwise described herein.

The term "D-configuration" as used in the context of the present invention refers to the configuration of the nucleoside compounds according to the present invention which mimics the natural configuration of sugar moeties as opposed to the unnatural occurring nucleosides or "L" configuration. The term "β" or "β anomer" is used to describe nucleoside analogs according to the present invention in which the nucleoside base is configured (disposed) above the plane of the carbocyclic moiety in the compound.

The term "enantiomerically enriched" is used throughout the specification to describe a nucleoside which includes at least about 95%, preferably at least about 96%, more preferably at least about 97%, even more preferably, at least about 98%, and even more preferably at least about 100% or more of a single enantiomer of that nucleoside. Carbocyclic nucleoside compounds according to the present invention are generally β-D-nucleoside compounds. When the present compounds according to the present invention are referred to in this specification, it is presumed that the nucleosides have the D-nucleoside configuration and are enantiomerically enriched (preferably, about 100% of the D-nucleoside), unless otherwise stated. The term "diasteromerically pure" is used to describe a single diastereomer of a compound according to the present invention which contains at least 95%, 96%, 97%, 98%, 99%, 99.5% or 100% by weight of a single diastereomer to the exclusion of other possible diastereomers.

The terms "coadminister" and "coadministration" are used synonymously to describe the administration of at least one of the nucleoside compounds according to the present invention in combination with at least one other agent, preferably at least one additional anti-viral agent, including other nucleoside anti-viral agents which are specifically disclosed herein in amounts or at concentrations which would be considered to be effective amounts at or about the same time. While it is preferred that coadministered agents be administered at the same time, agents may be administered at times such that effective concentrations of both (or more) agents appear in the patient at the same time for at least a brief period of time. Alternatively, in certain aspects of the present invention, it may be possible to have each coadministered agent exhibit its inhibitory effect at different times in the patient, with the ultimate result being the inhibition of the virus and the treatment of the aforementioned infections. Of course, when more than one viral or other infection or other condition is present, the present compounds may be combined with agents to treat that other infection or condition as required. In certain preferred compositions and methods, the present carbocyclic nucleoside compounds are coformulated and/or coadministered with at least one additional antiviral agent, preferably wherein the antiviral agent is acyclovir, famciclovir, ganciclovir, valaciclovir, vidarabine, ribavirin, zoster-immune globulin (ZIG), lamivudine, adefovir dipivoxil, entecavir, telbivudine, clevudine, tenofovir or a mixture thereof. In the case of HBV infections, the present 2'-fluorocarbocyclic nucleoside compounds may be coadministered preferably with another anti-HBV agent for example Hepsera (adefovir dipivoxil), lamivudine, entecavir, telbivudine, tenofovir, emtricitabine, clevudine, valtoricitabine, amdoxovir, pradefovir, racivir, BAM 205, nitazoxanide, UT 231-B, Bay 41-4109, EHT899, zadaxin (thymosin alpha-1) and mixtures thereof. In the case of HCV infections, the present 2'-fluorocarbocyclic nucleoside compounds may be coadministered preferably with another anti-HCV agent for example, NM 283, ribavirin, VX-950 (telaprevir), SCH 50304, TMC435, VX-500, BX-813, SCH503034, R1626, ITMN-191 (R7227), R7128, PF-868554, TT033, CGH-759, GI 5005, MK-7009, SIRNA-034, MK-0608, A-837093, GS 9190, ACH-1095, GSK625433, TG4040 (MVA-HCV), A-831, F351, NS5A, NS4B, ANA598, A-689, GNI-104, IDX102, ADX184, GL59728, GL60667, PSI-7851, TLR9 Agonist, PHX1766, SP-30 and mixtures thereof.

In alternative embodiments, especially in the case of HBV, HCV or Epstein-Barr treatment, compounds according to the present invention may also be coadministered with an anticancer agent.

The term "independently" is used herein to indicate that the variable, which is independently applied, varies independently from application to application.

The present invention relates to carbocyclic nucleoside compounds according to the structure:

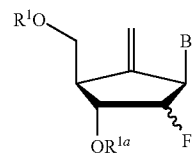

Where B is

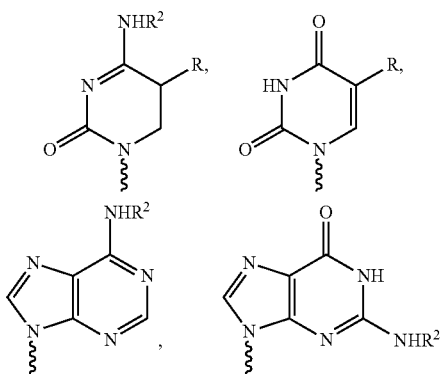

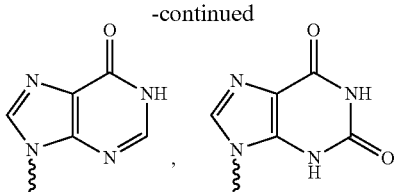

Wherein R is H, F, Cl, Br, I, $C_1$-$C_4$ alkyl (preferably $CH_3$), —C≡N, —C≡C—$R_a$,

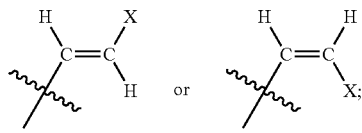

X is H, $C_1$-$C_4$ alkyl (preferably, $CH_3$), F, Cl, Br or I;
$R_q$ is H or a —$C_1$-$C_4$ alkyl group;
$R^1$ and $R^{1a}$ are each independently, H, an acyl group, a $C_1$-$C_{20}$ alkyl or ether group, an amino acid residue (D or L), a phosphate, diphosphate, triphosphate, phosphodiester or phosphoramidate group or together $R^1$ and $R^{1a}$ form a carbodiester, phosphodiester or phosphoramidate group with the oxygen atoms to which they are bonded;
$R^2$ is H, an acyl group, a $C_1$-$C_{20}$ alkyl or ether group or an amino acid residue (D or L);
Or a pharmaceutically acceptable salt, enantiomer, hydrate or solvate thereof.

Preferably $R^{1a}$ is H. Also preferably, $R^1$ and $R^2$ are each independently H or a $C_2$-$C_{20}$ acyl group, more preferably H. In other embodiments, $R^1$ is a phosphoramidate group as otherwise described herein or a phosphoramidate group according to the structure:

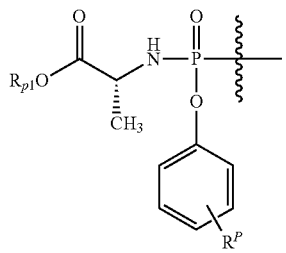

Where $R_{p1}$ is an optionally substituted (OH, halo) $C_1$-$C_{20}$ alkyl group, preferably a $C_1$-$C_4$ alkyl group, even more preferably a methyl, ethyl, isopropyl group or isobutyl group; and
$R^P$ is H, nitro, cyano, methoxy, or a $C_1$-$C_3$ alkyl group optionally substituted with from 1-3 halogen substituents (preferably F).

Preferred phosphoramidate groups for $R^1$ include those according to the chemical structure:

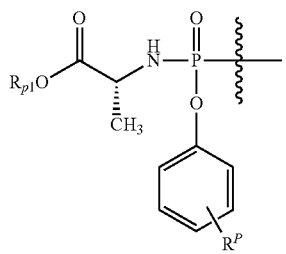

Where $R_{p1}$ is methyl, ethyl, isopropyl or isobutyl and $R^P$ is H, nitro, cyano, methoxy or $C_1$-$C_3$ alkyl, preferably H. In certain aspects of the invention the $R^1$ phosphoramidate group is preferably a

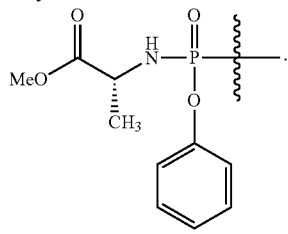

When $R^1$ is a phosphoramidate group as described above, $R^{1a}$ is preferably H and $R^2$ is preferably H or a $C_2$-$C_{20}$ acyl group.
B is preferably

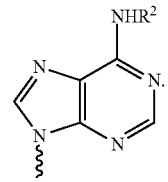

In alternative preferred aspects, the compound is represented by the chemical structure:

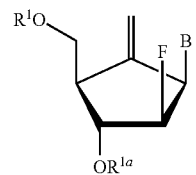

Where B is as described above, is preferably

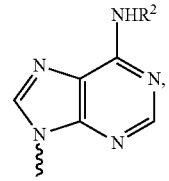

and $R^1$, $R^{1a}$ and $R^2$ are as otherwise described hereinabove, most preferably, $R^{1a}$ and $R^2$ are H and $R^1$ is preferably a phosphoramidate group, especially including a phosphoramidate group according to the structure:

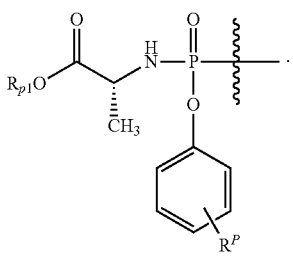

Where $R_{p1}$ is methyl, ethyl, isopropyl or isobutyl and $R^p$ is H.

The present invention also relates to pharmaceutical compositions comprising an effective amount of a compound as described above, optionally in combination with a pharmaceutically acceptable carrier, additive or excipient. In alternative embodiments, pharmaceutical compositions may also contain one or more additional antiviral agents as otherwise described herein in combination with a additive, carrier or excipient.

Methods of treatment represent further embodiments according to the present invention. In this aspect, a method of treating or reducing the likelihood of a viral infection or a secondary disease state or condition thereof, in particular, a viral infection from HBV, HCV, HSV-1, HSV-2, CMV (including HCMV), VZV or EBV infection in a patient in need of therapy or at risk for infection or a secondary disease state or condition thereof comprises administering to said an effective amount of a compound as otherwise described above. Alternative embodiments rely on coadministering compounds according to the present invention in combination with additional antiviral agents to said patient. In preferred aspects, a method of treating or reducing the likelihood of HBV, including a drug resistant strain thereof or a secondary disease or condition which occurs as a consequence of HBV is directed to administering to a patient in need an effective amount of compound according to the present invention as described herein, preferably a compound according to the chemical structure:

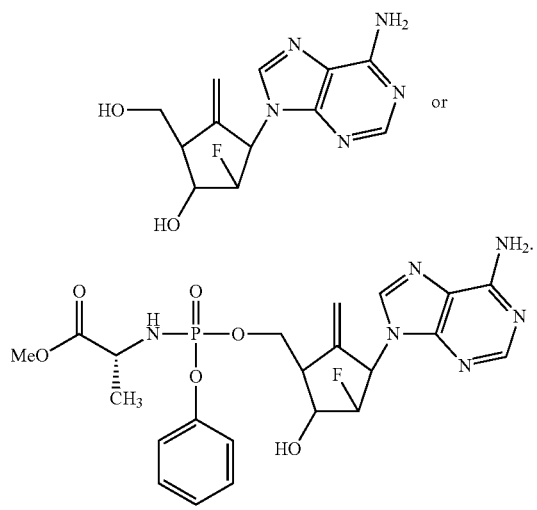

Or a pharmaceutically acceptable salt, solvate or polymorph thereof.

Pharmaceutical compositions based upon the nucleoside compounds according to the present invention comprise one or more of the above-described compounds in an effective amount for treating or reducing the likelihood of a viral infection, especially a HBV, HCV, HSV-1, HSV-2, CMV (HMCV), VZV or EBV infection in a patient in need of therapy thereof, optionally in combination with a pharmaceutically acceptable additive, carrier or excipient. One of ordinary skill in the art will recognize that a therapeutically effective amount will vary with the infection or condition to be treated, its severity, the treatment regimen to be employed, the pharmacokinetics of the agent used, as well as the patient or subject (animal or human) to be treated.

In the pharmaceutical aspect according to the present invention, the compound according to the present invention is formulated preferably in admixture with a pharmaceutically acceptable carrier. In general, it is preferable to administer the pharmaceutical composition in orally-administrable form, but certain formulations may be administered via a parenteral, intravenous, intramuscular, transdermal, buccal, subcutaneous, suppository or other route. Intravenous and intramuscular formulations are preferably administered in sterile saline. In certain instances, transdermal administration may be preferred. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the routineer's skill to modify the route of administration and dosage regimen of a particular compound in order to manage the pharmacokinetics of the present compounds for maximum beneficial effect in patients.

In certain pharmaceutical dosage forms, the pro-drug form of the compounds, especially including acylated (acetylated or other) and ether (alkyl and related) derivatives, phosphate esters and various salt forms of the present compounds, are preferred. One of ordinary skill in the art will recognize how to readily modify the present compounds to pro-drug forms to facilitate delivery of active compounds to a targeted site within the host organism or patient. The routineer also will take advantage of favorable pharmacokinetic parameters of the pro-drug forms, where applicable, in delivering the present compounds to a targeted site within the host organism or patient to maximize the intended effect of the compound.

The amount of compound included within active formulations according to the present invention is an effective amount for treating the infection or condition, especially a viral infection as otherwise described herein. In general, a therapeutically effective amount of the present compound in pharmaceutical dosage form usually ranges from about 0.05 mg/kg to about 100 mg/kg per day or more, more preferably, slightly less than about 1 mg/kg to about 25 mg/kg per day of the patient or considerably more, depending upon the compound used, the condition or infection treated and the route of administration. The active nucleoside compound according to the present invention is preferably administered in amounts ranging from about 0.5 mg/kg to about 25 mg/kg per day of the patient, depending upon the pharmacokinetics of the agent in the patient. This &sage range generally produces effective blood level concentrations of active compound which may range from about 0.05 to about 100 micrograms/cc of blood in the patient. For purposes of the present invention, a prophylactically or preventive effective amount (i.e. an amount which is effective to reduce the likelihood of a patient at risk from contracting a viral infection) of the compositions according to the present invention falls within the same concentration range as set forth above for therapeutically effective amount and is usually the same as a therapeutically effective amount.

Administration of the active compound may range from continuous (intravenous drip) to several oral administrations per day (for example, Q.I.D.) or transdermal administration and may include oral, topical, parenteral, intramuscular, intravenous, sub-cutaneous, transdermal (which may include a penetration enhancement agent), buccal and suppository administration, among other routes of administration. Enteric coated oral tablets may also be used to enhance bioavailability of the compounds from an oral route of administration. The most effective dosage form will depend upon the bioavailability/pharmacokinetics of the particular agent chosen as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques. The use of these dosage forms may significantly enhance the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free nucleosides, acyl/alkyl nucleosides or phosphate ester pro-drug forms of the nucleoside compounds according to the present invention.

In particularly preferred embodiments according to the present invention, the compounds and compositions are used to treat, prevent or delay the onset of a viral infection as otherwise disclosed herein (HBV, HCV, HSV-1, HSV-2, CMV, VZV and/or EBV). Preferably, to treat, prevent or delay the onset of these infections or disease states and/or conditions which occur secondary to these viral infections (especially cirrhosis, fibrosis and/or liver cancer secondary to HBV and/or HCV infections), the compositions will be administered in oral dosage form in amounts ranging from about 250 micrograms up to about 500 mg or more at least once a day, preferably, up to four times a day. The present compounds are preferably administered orally, but may be administered parenterally, topically or in suppository form.

In the case of the co-administration of the present compounds in combination with an another compound used to treat a viral infection, in particular, a viral infection such as a HBV, HCV, HSV-1, HSV-2, CMV, VZV and/or EBV infection, the amount of the carbocyclic nucleoside compound according to the present to be administered ranges from about 1 mg/kg. of the patient to about 500 mg/kg. or more of the patient or considerably more, depending upon the second agent to be co-administered and its potency against each of the viral infections to be inhibited, the condition or infection treated and the route of administration. In the case of coadministration, the other antiviral agent may be preferably administered in amounts ranging from about 100 ug/kg (micrograms per kilogram) to about 500 mg/kg. In certain preferred embodiments, these compounds may be preferably administered in an amount ranging from about 1 mg/kg to about 50 mg/kg or more (usually up to about 100 mg/kg), generally depending upon the pharmacokinetics of the two agents in the patient. These dosage ranges generally produce effective blood level concentrations of active compound in the patient. Typical antiviral agents which may be coadministered with compounds according to the present invention include acyclovir, famciclovir, ganciclovir, valaciclovir, vidaribine, ribavirin, zoster-immune globulin (ZIG), lamivudine, adefovir dipivoxil, entecavir, telbivudine, clevudine, tenofovir and mixtures thereof. In the case of treating HBV infections, preferred compounds for combining with the present 2'-fluorocarbocyclic nucleoside compounds include, for example, Hepsera (adefovir dipivoxil), lamivudine, entecavir telbivudine, tenofovir, emtricitabine, clevudine, valtoricitabine, amdoxovir, pradefovir, racivir, BAM 205, nitazoxanide, UT 231-B, Bay 41-4109, EHT899, zadaxin (thymosin alpha-1) and mixtures thereof. In the case of HCV infections, the present 2'-fluorocarbocyclic nucleoside compounds may be coadministered preferably with another anti-HCV agent for example, NM 283, VX-950 (telaprevir), SCH 50304, TMC435, VX-500, BX-813, SCH503034, R1626, ITMN-191 (R7227), R7128, PF-868554, TT033, CGH-759, GI 5005, MK-7009, SIRNA-034, MK-0608, A-837093, GS 9190, ACH-1095, GSK625433, TG4040 (MVA-HCV), A-831, F351, NS5A, NS4B, ANA598, A-689, GNI-104, IDX102, ADX184, GL59728, GL60667, PSI-7851, TLR9 Agonist, PHX1766, SP-30 and mixtures thereof.

The compounds according to the present invention, may advantageously be employed prophylactically to prevent or reduce the likelihood of a viral infection or to prevent or reduce the likelihood of the occurrence of clinical symptoms associated with the viral infection or to prevent or reduce the likelihood of the spread of a viral infection to another person. Thus, the present invention also encompasses methods for the prophylactic treatment of a HBV, HCV, HSV-1, HSV-2, CMV, VZV and/or EBV infection. In this aspect according to the present invention, the present compositions may be used to prevent, reduce the likelihood of and/or delay the onset of a viral infection or a virus related disease state or condition (e.g., cirrhosis, fibrosis and/or liver cancer) or the spread of infection to other people. This prophylactic method comprises administering to a patient in need of such treatment or who is at risk for the development of a HBV, HCV, HSV-1, HSV-2, CMV, VZV and/or EBV infection, including a virus related disease state or condition or an infected patient who wishes to prevent or reduce the likelihood of a viral infection from spreading to another person, an amount of a compound according to the present invention alone or in combination with another anti-viral effective for alleviating, preventing or delaying the onset of the viral infection. In the prophylactic treatment according to the present invention, it is preferred that the antiviral compound utilized should be as low in toxicity and preferably non-toxic to the patient. It is particularly preferred in this aspect of the present invention that the compound which is used should be maximally effective against the virus and should exhibit a minimum of toxicity to the patient. In the case of compounds of the present invention for the prophylactic treatment of viral infections, these compounds may be administered within the same dosage range for therapeutic treatment (i.e., about 250 micrograms up to about 500 mg. or more from one to four times per day for an oral dosage form) as a prophylactic agent to prevent the proliferation of the viral infection or alternatively, to prolong the onset of or reduce the likelihood of a patient contracting a virus infection which manifests itself in clinical symptoms.

In addition, compounds according to the present invention may be administered alone or in combination with other agents, including other compounds of the present invention. Certain compounds according to the present invention may be effective for enhancing the biological activity of certain agents according to the present invention by reducing the metabolism, catabolism or inactivation of other compounds and as such, are co-administered for this intended effect.

Chemical Synthesis

Figure 1:
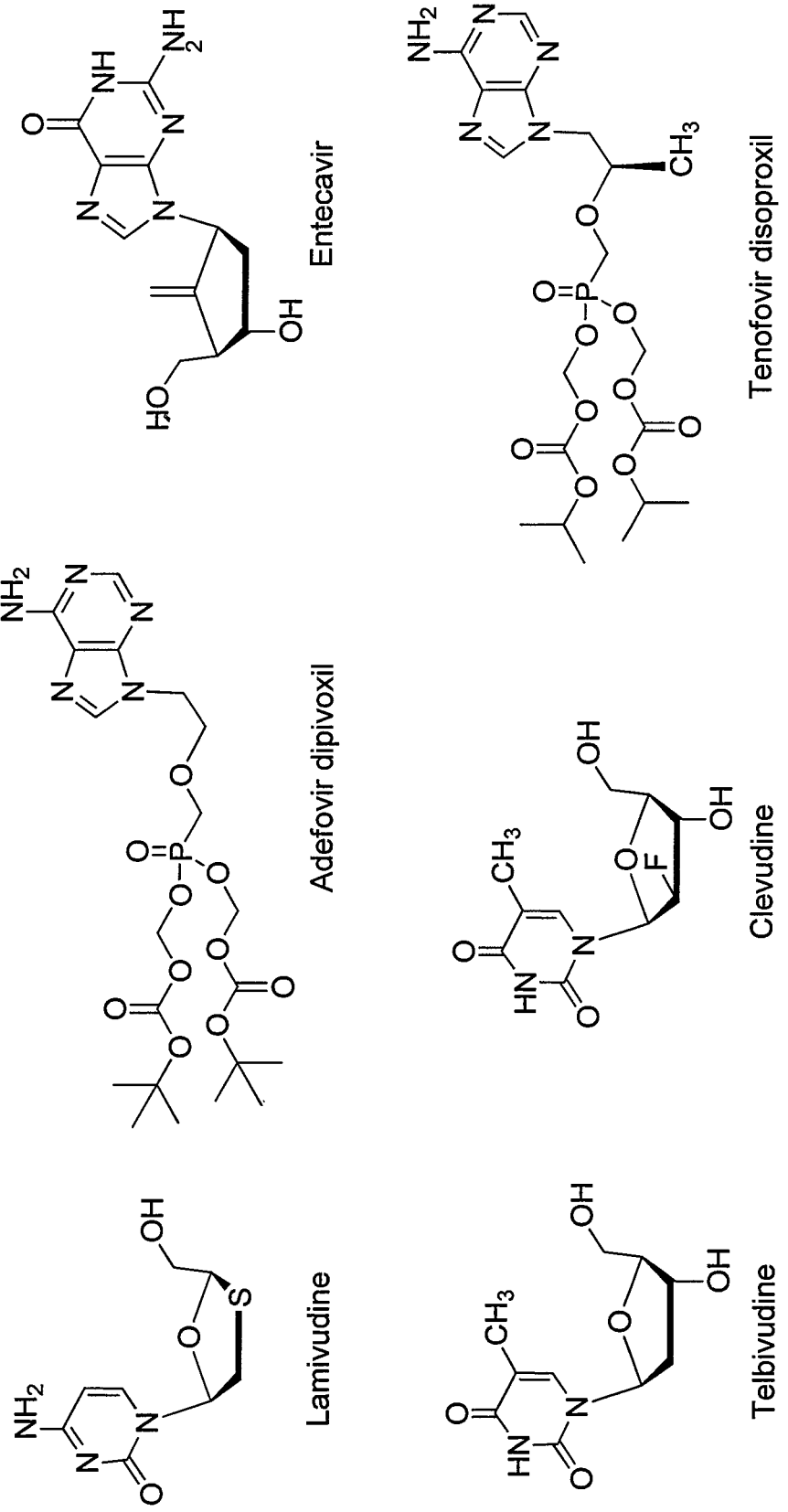
FIG. 1 shows a number of current anti-HBV nucleosides/nucleotides.
Figure 2:
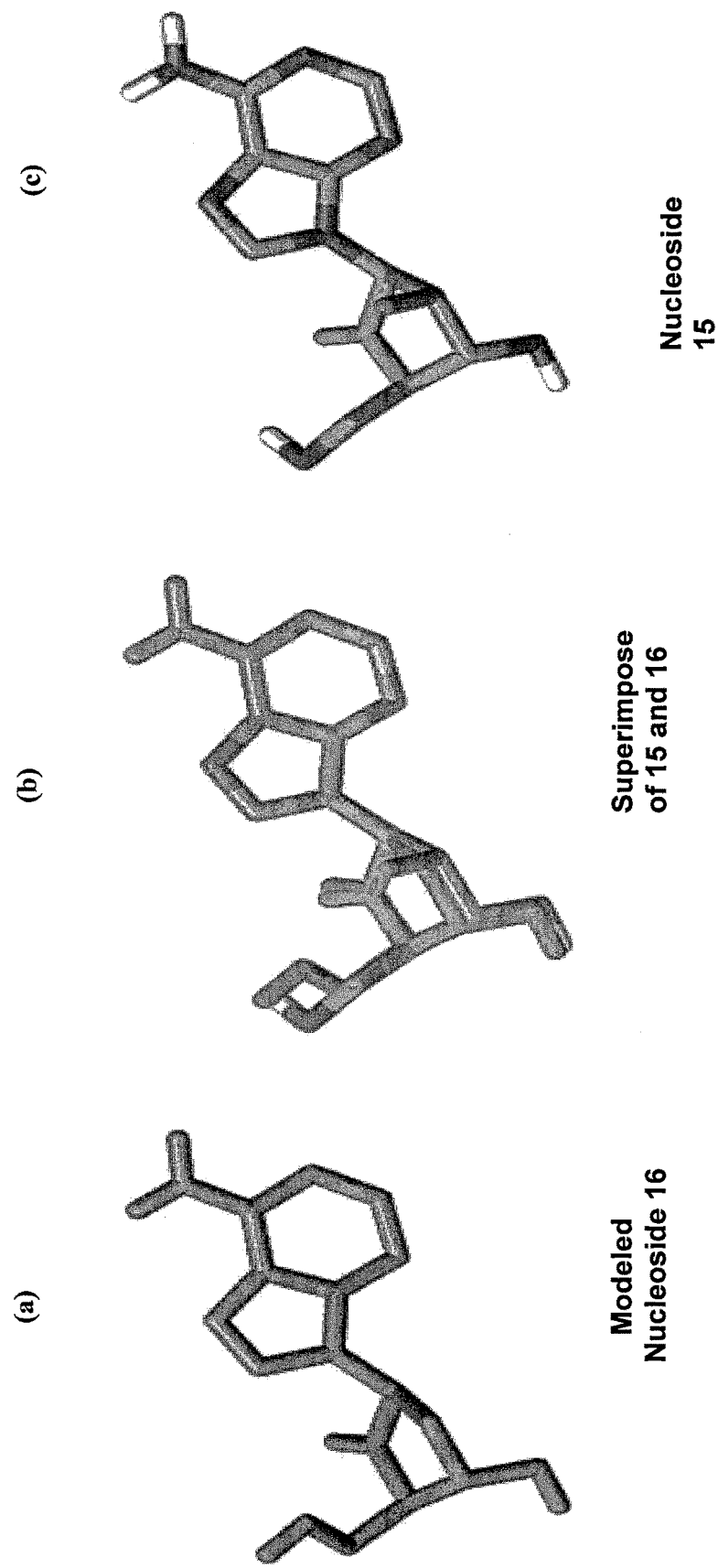
FIG. 2 shows (a) Low-energy conformer of modeled nucleoside 16 (indicated in blue) adopted a 2'-endo, Southern conformation. Although this conformer is not global minimum, the energy barrier between them is as low as 0.5 kJ/mol. (b) The superimposed the structures of 16 and 15 indicated the similarity between the conformations of two molecules. (c) Fluorinated carbocyclic nucleoside 15 (C: gray, N: blue, 0: red, F: green, H: white) also preferred a 2'-endo, Southern conformation.
Figure 3:
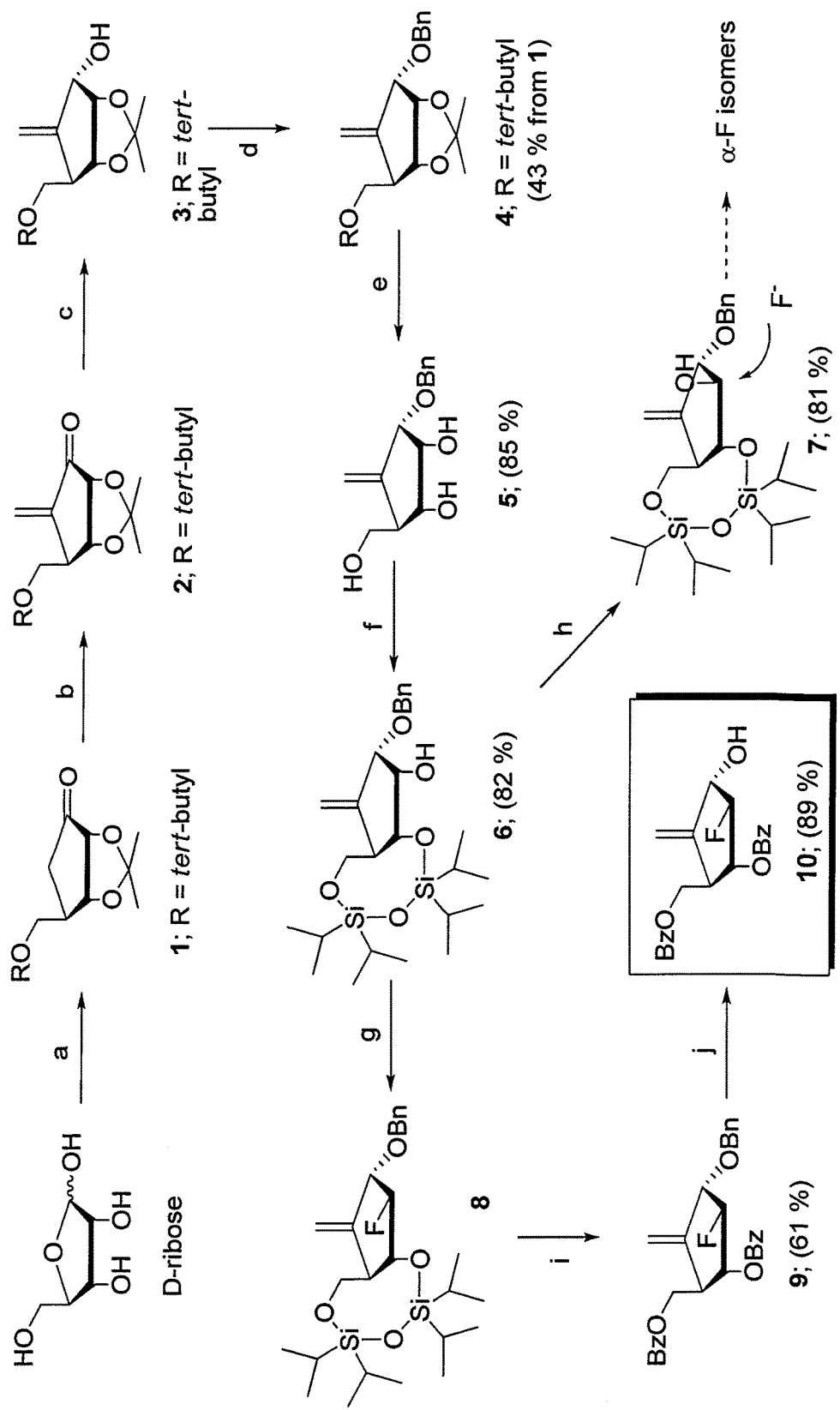
FIG. 3 shows synthetic scheme 1, which provides a series of synthetic steps to sugar synthon intermediate 10. The following reagents and conditions were used: (a) Ref. 33, 34, 40, $J.$ $Org.$ $Chem.$ 2003, 68, 9012-9018; (b) i) LDA, Echenmoser's salt, THF, $-78°$ C., ii) MeI, rt, iii) sat. NaHCO$_3$ solution, rt; (c) NaBH$_4$/CeCl$_3$.7H$_2$O, THF, $-78°$ C.; (d) NaH, BnBr, TBAI, THF, rt; (e) 3N HCl, MeOH, 90° C.; (f) TIPDSCl, Py, $-30°$ C. to rt; (g) DAST, CH$_2$Cl$_2$, rt; (h) i) Tf$_2$O, Py, $-30°$ C. to rt, ii) CeOAc, 18-Crown-6, benzene, 50° C.; iii) NaOMe, MeOH, rt; (i) i) TBAF/HOAc, THF, rt, ii) B$_z$Cl, Py, rt; (j) BCl$_3$, CH$_2$Cl$_2$, $-78°$ C.
Figure 4:
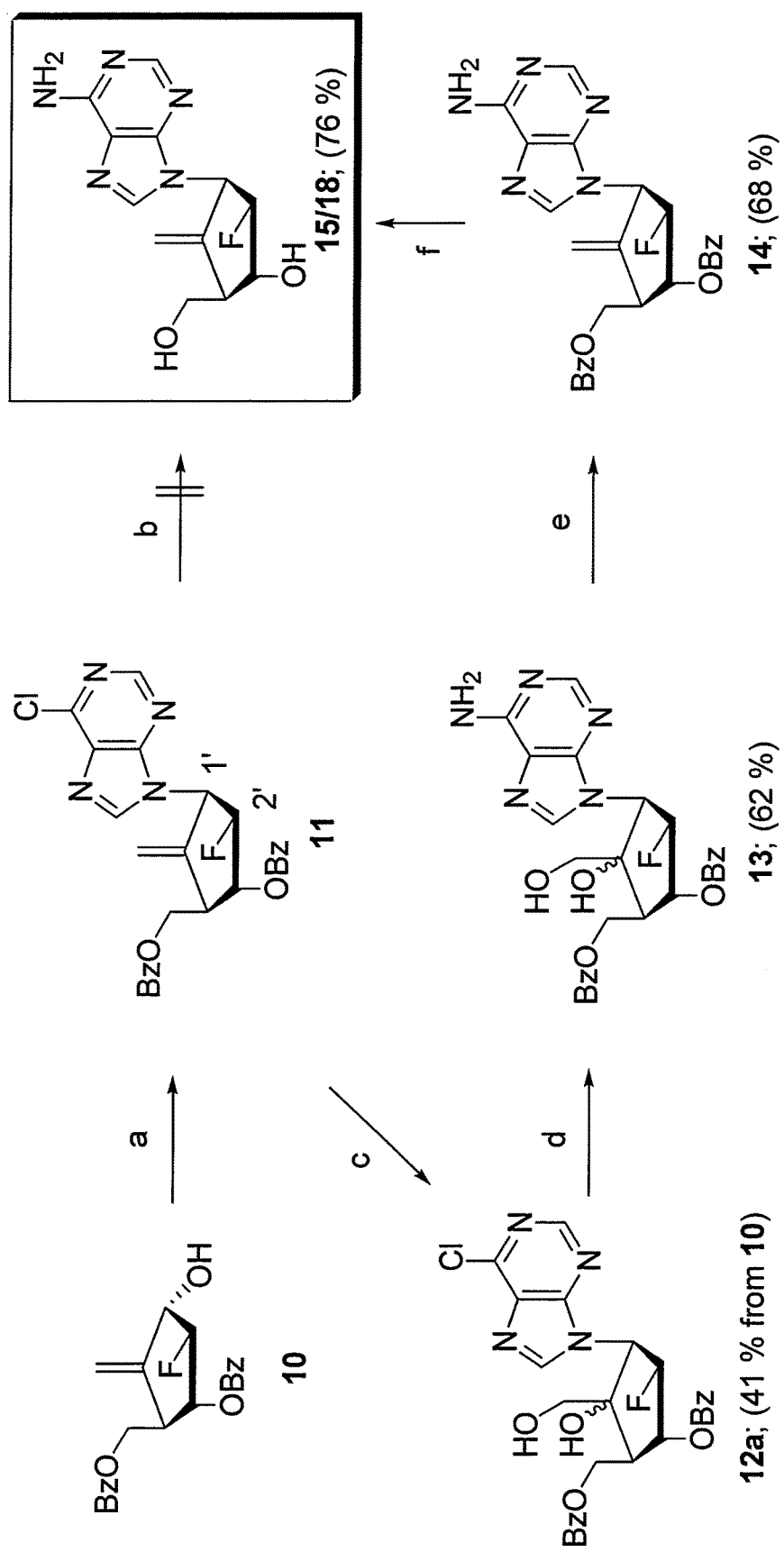
FIG. 4 shows synthetic scheme 2, which provides a series of synthetic steps to nucleoside compound 15/18. The following reagents and conditions were used: (a) DIAD, Ph$_3$P, 6-chloropurine, THF, rt; (b) NH$_3$, MeOH, 100° C. or NaN$_3$, DMF followed by H$_2$O; (c) i) OsO$_4$/NMO, Acetone/H$_2$O, rt, ii) NaN$_3$, DMF, 140° C., iii) H$_2$/Pd/C, EtOH, rt; (d) i) 1-bromocarbonyl-1-methylethyl acetate, acetonitrile, $-30°$ C.-rt, ii) Zn/HOAc, DMF, rt; (e) DIBAL-H, CH$_2$Cl$_2$, $-78°$ C.
Figure 5:
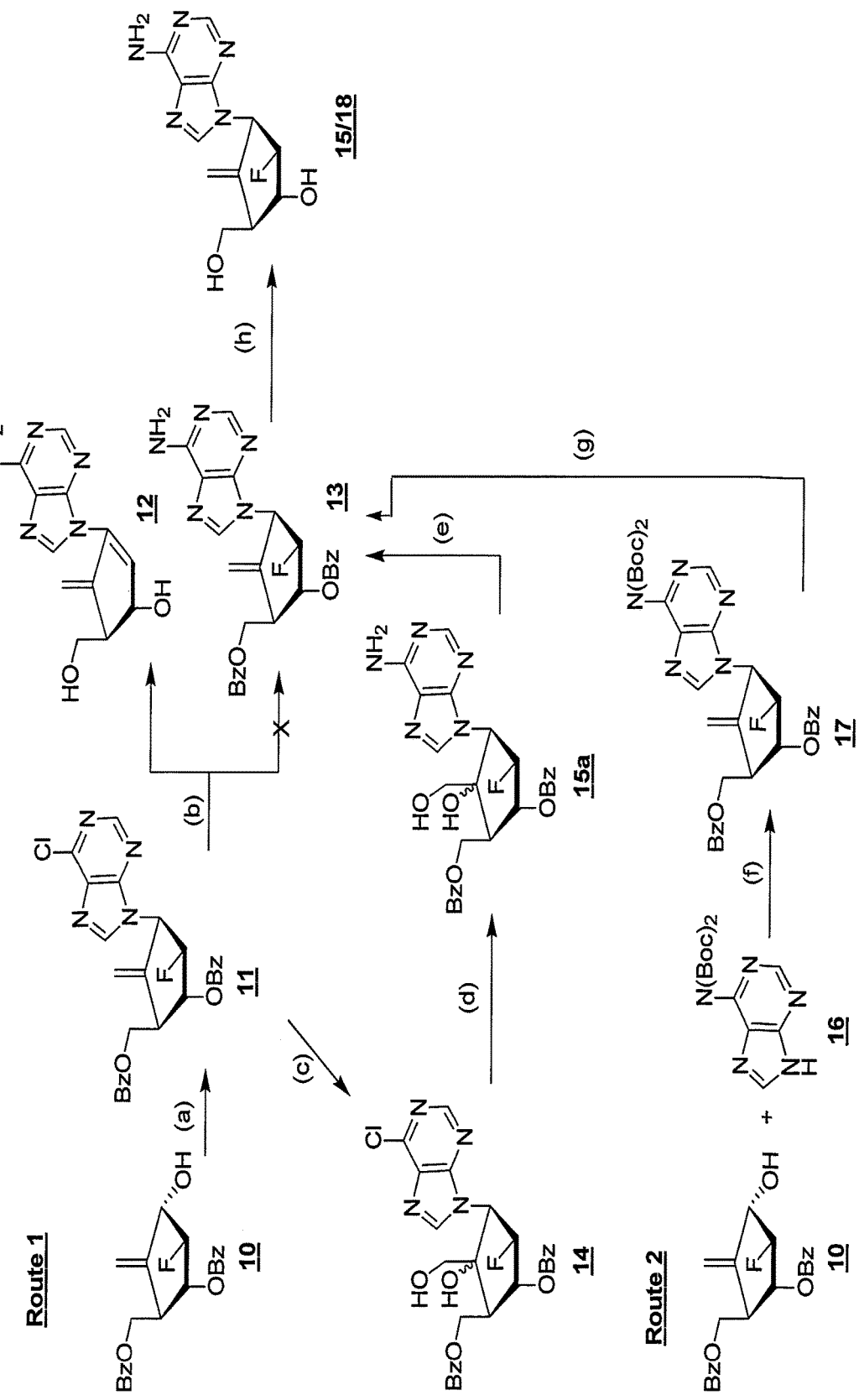
FIG. 5 shows alternative scheme 2, which provides a series of synthetic steps to compound 15/18, which was used in testing against wild-type and mutant HBV as described in the examples section. The following reagents and conditions were used: (a) see Jin, et al., $J.$ $Org.$ $Chem.,$ 2003, 68, 9012-9018 (b) i) LDA, Eshenmoser's salt, THF, $-78°$ C.; ii) MeI, rt; iii) sat. NaHCO$_3$ solution, rt; (c) NaBH$_4$/CeCl$_3$.7H$_2$O, MeOH, $-78°$ C.; (d) NaH, BnBr, DMF, 0° C.; (e) TFA/H$_2$O (2:1), 50° C.; (f) TIDPSCl$_2$/Imidazole, DMF, 0° C.; (g) DAST, CH$_2$Cl$_2$, rt; (h) TBAF/AcOH, THF, rt; (i) BzCl, Pyridine, rt; (j) BCl$_3$, CH$_2$Cl$_2$, $-78°$ C.

In general, compositions according to the present invention are synthesized readily from D-ribose according to schemes I, II and alternative scheme II, which are presented in attached FIGS. 3, 4, 5 and 8. In this scheme, D-ribose is first converted through a series of chemical steps to a protected carbocyclic five-membered ring as depicted in scheme 1, FIG. 3 (compound 10). Pursuant to scheme I, compound 10 is then converted to a compound according to the present invention (compound 15/18) by condensing a nucleoside base (in the figure, a 6-chloroadenine to produce compound 11, which is subsequently converted to an amine group as presented to produce compound 15/18. In alternative scheme II (FIG. 5), compound 15/18, is synthesized from compound 10 using alternative approaches as outlined in alternative scheme II (FIG. 5). Alternative scheme III, FIG. 8 shows that compound 15/18 and its prodrug 15P containing a phosphoramide group on the 5' position of the sugar synthon Each compound according to the present invention may be produced by analogy following the general chemical scheme presented in FIGS. 3, 4, 5, 6 and 7.

Each of the carbocyclic nucleoside compounds prepared as above may be readily converted to prodrug or alternative forms of the present invention (e.g., acylated, phosphate or phosphodiester derivatives, etc. as otherwise described herein) utilizing standard synthetic chemistry for introducing various groups onto the hydroxyl positions at 2', 3' and/or 5' positions of the carbocyclic moiety or alternatively, at the exocyclic amine position at the 4-position of the cytosine base. Acylation proceeds through well known synthetic methods (acyl anhydride, acyl halide, etc.) and phosphorylation may be performed using standard chemical techniques which are well-known in the art. One of ordinary skill may readily synthesize compounds according to the present invention by utilizing specific chemical steps which are presented herein or by way of analogy, through the use of chemical steps which are in the literature, by way of analogy.

In the synthesis of carbocyclic nucleosides, the construction of desired carbocycles in decent yield and scale is often troublesome. There are only a few reports aimed at preparation of carbocyclic core with 6'-exo-cyclic alkene, including the protocol of the synthesis of entecavir from Bristol-Meyer Squibb or, through the radical cyclization reactions.[36-39] However, these methodologies are not very suitable for the modification on the 2'-position of the carboring. Recently, the efficient and practical synthetic methodology of the key intermediates 1 has been also accomplished by our group.[33,34,40] Therefore, an alternative route (Scheme 1 and 2) has been developed in order to prepare 2'-F-6'-methylene carbocyclic nucleosides.

More specifically, the cyclopentanone 1 was prepared according to the known procedure.[33,34,40] Reaction of the enolate of 1 with Eschenmoser's salt placed an N,N-dimethylaminomethyl group on the α-position of the ketone. After Hofmann elimination, a 6'-methylene was installed in decent yield. Due to the steric hindrance on the α-face, the α,β-unsaturated ketone 2 was reduced by a typical Luche reduction condition to give exclusively α-hydroxyl compound 3. Protection of allylic alcohol by the benzyl group smoothly generated compound 4 in 43% yield from cyclopentanone 1. Simultaneously deprotection of acetonide and tert-butyl groups under acidic condition provided triol 5 in 85% yield. Treatment of triol 5 with dichlorotetraisopropyldisiloxane (TIPDSCl) in pyridine gave a high yield of 3',5'-diprotected compound 6. The free 2'-α-OH in 6 is ready for a fluorination reaction. Furthermore, when compound 6 was subjected to a three-step protocol including triflation, $S_N 2$ replacement and deacetylation, 2'-α-OH compound 7 was obtained in 81% yield, which can be used for the preparation of 2'-α-F isomers. Reaction of 6 with (diethylamino)sulfur trifluoride (DAST) yielded a major product as 2'-β-F compound 7. However, subsequent debenzylation was not successful in the presence of silyl group under either Birch reduction or Lewis's acid conditions. Therefore, the silyl group was replaced by benzoyl group via standard procedure to provide 10. Compound 10 was then subjected to the borontrichloride ($BCl_3$) at −78° C. and successfully produced the fully elaborated intermediate 11 in 89% yield (Scheme 1).

Construction of nucleoside 12 was accomplished by typical Mitsunobu conditions[33,34] by treating 11 with 6-chloropurine in the presence of triphenylphosphine and diisopropyl azodicarboxylate in THF at 0° C. to room temperature for 1 hour. Unfortunately, direct amination of chlorine atom to amino group and simultaneous hydrolysis of benzoyl groups by methanolic ammonia was unsuccessful. One molecule of HF was eliminated under such condition as confirmed by $^1$H-NMR and $^{19}$F-NMR. Interestingly, even very mild condition, such as Staudinger reaction, failed to achieve the transformation. It was reasoned that the 6'-methylene group activated the 1'-proton to undergo a trans-elimination reaction to form a stable diene. In order to circumvent the effect of 6'-methylene group, a temporal protection is preferred. Dihydroxylation of the exo-cyclic alkene was performed using osmium tetraoxide/NMO to provide a mixture of diasteromers 12. As expected, conversion of 12 to the adenine derivative 13 went smoothly by reacting with sodium azide followed by $H_{2-}$ reduction in 62% yield. Several conditions were then studied to regenerate the olefin from diol. The Corey's olefin synthesis by the desulfurization of 1,3-dioxolane-2-thiones with 1,3-dimethyl-2-phenyl-1,3,2-diazaphospholidine is well known due to its mildness and effectiveness.[41] However, when we applied this condition to compound 13, only complex reaction mixture was obtained. Another general method by heating 2-methoxy-1,3-dioxolane derivatives in acetic anhydride was also unsuccessful in the present case, which may be due to the high reaction temperature.[42] Finally, we adopted the reductive elimination protocol which was widely used in the synthesis of 2',3'-dideoxy-2',3'-dihydro nucleosides or 2',3'-dideoxy nucleosides.[43-45] Diol 13 was reacted with 1-bromocarbonyl-1-methylethyl acetate at −30° C. to room temperature followed by activated Zn metal in DMF in the presence of catalytic amount of HOAc at room temperature for 8 hours.

The desired nucleoside 14 with 6'-methylene group was obtained in 68% yield in two steps. Based on our previous experience, basic condition would not be compatible with 14 to deblock the benzoyl groups, as 6'-methylene group and 2'-F are present simultaneously in the molecule. Therefore, a reductive cleavage method was applied. After treating 14 with diisobutyl alumina hydride (DIBAL-H) in $CH_2Cl_2$ at −78° C. for 30 min, the target adenosine analog 15 was eventually obtained in 76% yield (Scheme 2). Assignment of the structures of newly synthesized nucleosides was accomplished by NMR, elemental analysis, high resolution mass spectroscopy, and UV spectroscopy.

An alternative approach may also be taken to produce compound 15 (labeled as compound 18 in alternative scheme II, FIG. 5), the synthetic steps which are set forth alternative chemical syntheses (FIG. 5) were used. Several approaches were taken to produce compound 18 (same as compound 15 of FIG. 4). Compound 10 was condensed with 6-chloropurine under the standard Mitsunobu condition to give 11 in 76% yield. However, attempted amination of 11 to obtain the corresponding adenine derivative 13 by methanolic ammonia was unsuccessful. Only the byproduct 12 was isolated, which was probably formed by losing HF under basic conditions. It was speculated that the stability of the elimination-product 12, a conjugated diene, is the driving force to promote the side reaction. Therefore, transient protection of exocyclic double bond was required. Compound 11 was hence treated with osmium tetroxide/NMO to provide 14 in 41% of yield. This was treated with $NaN_3$, followed by $H_2$ reduction resulted in 62% of the adenine derivative 15a. Reductive elimination of 15a with 1-bromo-carbonyl-1-methylethyl acetate followed by activated Zn in the presence of catalytic amounts of AcOH furnished the desired nucleoside 13 in 68% yield.

Due to the multiple step synthesis as well as low yield of 13 in the route-1, recently the inventors revised the synthesis to the route-2. N-Boc protected adenine 16 was synthesized according to the reported protocol in literature[15] and condensed with 10 to obtain 17 in 76% yield. The deprotection of the Boc group was carried out by TFA to afford 82% of 13. Eventually, the treatment of 13 with DIBAL-H gave the target compound 18 (compound 15) in 76% yield. Analytical data for compound 15/18 is presented in the examples section below.

FIG. 6 provides another depiction of the synthesis of compounds 15/18. In the scheme set forth in FIG. 6, the synthesis of target compound 15/18 commenced with ketone 1 as the key intermediate as briefly described in the FIG. 6 scheme. Starting from D-ribose, the ketone 1 was synthesized via nine steps according to the know procedure of Jin, et al., *J. Org. Chem.*, 68: 9012-9018 (2003). The exocyclic methylene group was introduced with Mannich base (Eshenmoser's salt) followed by the Hoffmann degradation to an enone, which was selectively reduced by using sodium borohydride to exclusively give the α-hydroxyl compound 3 in good yield. The compound 3 was converted to 2-fluorine derivative 4 in 7 steps, which was condensed with N-Boc protected adenine according to the reported protocol of Dey and Garner, *J. Org. Chem.*, 65:7697 (2000), from which the final nucleoside 15/18 was obtained in three steps. The monophosphate prodrug 15p/18p was also prepared according to the literature procedure of McGuigan, et al, *J. Med. Chem.*, 53:4949-4957 (2010).

In another synthesis, pursuant to the chemical scheme set forth in the chemical scheme of FIG. 7, compound 15/18 is synthesized from protected lactum (−) Vince lactum. Each of the steps and reagents used is presented in the description of FIG. 7, above.

The phosphoramidate prodrug compound 15P/18P was prepared as presented in the scheme of FIG. 8. In that scheme, the phenylphosphoryldichloride (compound 1P in FIG. 8) is reacted with L-alanine substituted ester hydrochloride in the presence of triethylamine in methylene chloride to produce the appropriately substituted chlorophenylphorphoryl-L-alaninate (2P or 3P of FIG. 8). Compound 2P or 3P of FIG. 8 is then reacted with compound 15/18 in N-Methylisoimidazole in solvent (tetrahydrofuran) overnight to produce the prodrug compound 15P/18P or compound 15PI/18PI. The experimental procedure for the presentation of the synthesis in FIG. 8 is presented in the experimental section. It is noted that the corresponding ethyl and isobutyl ester analogs of the methyl ester 15P/18P and isopropyl ester 15PI/18PI are prepared in the same manner using analogous reactants. It is also noted that the phosphorous group is a chiral center and the presentation in FIG. 8 provides a diastereomeric mixture of 15P/18P and 15PI/18PI. The diastereomeric mixture may be separated into purified diastereomers using methods well-known in the art including selective crystallization (one diastereomer crystallizes out of solution to the exclusion of the other diastereomer), chiral column chromatography (HPLC, etc.).

Antiviral Activity Against HBV-WT and Mutation Strains

Lamivudine is the first licensed anti-HBV nucleoside which led to the breakthrough in the field of HBV therapy. The treatment of patients with lamivudine is often associated with significant reduction of serum HBV DNA level and serological conversion and histological improvement in comparison to the placebo groups.[11,46] However, the rate of lamivudine-resistant mutations is relatively high (70% after 5 years treatment), which limits lamivudine's clinical impact.[11-14] The primary mutation is rtM204V/I and compensatory mutations are including rtV173L, rtL180M and rtL80I.[9,10] From a structural perspective, the rtM204V/I induced the resistance by means steric hindrance between the side chain of Val/Ile204 and L-sugar ring of lamivudine.[47,48] Considering the same L-configuration, telbivudine is inevitably cross-resistant to the lamivudine resistance, such as rtM204I.[15] Another important clinical HBV mutation is rtN236T, which is associated with adefovir therapy at a rate as high as 29% after 5 years treatment[16-18] Molecule modeling study indicated that the mutation from Asp to Thr on condon 236 resulted in the loss of hydrogen bonding between the γ-phosphate of adefovir-diphosphate and original Asp236, which decreased the binding affinity and therefore compromised the antiviral activity of adefovir-against rtN236T mutant.[49,50]

In view of the significance of lamivudine- and adefovir-resistant mutations in the clinical application of anti-HBV treatment, the synthesized nucleoside 15/18 was tested against HBV WT as well as lamivudine- and adefovir-resistant mutants. The screening data are summarized in Table 1, FIG. 10. Nucleoside 15/10 exhibited a potent antiviral activity against HBV-WT with a 50% effective concentration ($EC_{50}$) of 1.5 μM and 90% effective concentration ($EC_{90}$) of 4.5 μM. Interestingly, nucleoside 15/18 is also active against lamivudine-resistant mutants including rtM204V/I±rtL180M. The fold increase is around 1.0-1.2, which is comparable to that of adefovir. Furthermore, compound 15/18 did not lose any activity against adefovir mutant (rtN236T) either, with an $EC_{90}$ value of 4.6 μM.

The structure of 15/18 is analogous to the approved anti-HBV nucleoside, entecavir, except bearing an extra β-fluorine atom on the 2'-position. The conformations of low-energy conformers of two nucleosides are also similar as indicated in our modeling study (vide infra). However, the fluorinated nucleoside 15 is not cross-resistant to all the tested lamivudine-resistant mutants while entecavir lost activity by a fold of 8.[50] Although the detailed mechanism is still unknown, the 2'-fluorine substitution may be very important.

The synthesized nucleoside 15/18 was evaluated for its antiviral activity against wild-type HBV as well as drug resistant mutants in vitro, and the results are summarized in Table 1, below. As compound 15/18 is a derivative of an adenine analog, the inventors compared the antiviral activity to adefovir instead of entecavir, a guanine analog although the carbocyclic moiety is similar to that of entecavir. From the anti-HBV evaluation, the compound 15/18 demonstrated significant anti-HBV activity against wild-type HBV with $EC_{50}$ value of 1.5 μM. The antiviral potency was similar to adefovir, while being 7 fold less potent than that of lamivudine. The concentration of compound required to inhibit 90% ($EC_{90}$) of HBV DNA in wild-type is 4.5 μM, which is a 1.5 fold more potent than that of adefovir (7.1 μM).

Compound 15/18 also showed excellent activity against both lamivudine- and adefovir-associated HBV mutants. It was found that compound 15/18 imparts a 4.5-fold enhanced $EC_{50}$ value (1.7 μM) and a 7.8-fold more favorable $EC_{90}$ value (4.6 μM) against adefovir mutant rtN236T. For rtM204V and rtM204I, compound 18 showed $EC_{50}$ value of 1.8 and 1.0 μM, respectively. For rtM204V mutant, the potency of adefovir and compound 15/18 is similar, but for rtM204I, compound 15/18 was more potent than that of adefovir in $EC_{50}$ as well as $EC_{90}$ values. For mutant rtL180M, the antiviral activity of compound 15/18 was similar to that of lamivudine in the $EC_{50}$ value (2.1 vs. 1.5), while it exhibited a 4.3 fold increased antiviral activity in the $EC_{90}$ value (5.1 vs. 22.0). Compound 15/18 was more potent than that of adefovir against the same mutant in both $EC_{50}$ and $EC_{90}$ values.

Compound 15/18 was also tested against double mutant rtL180M/rtM204V and it exhibited $EC_{50}$ value of 2.2 μM, that was equal to that of adefovir, while the $EC_{90}$ value (5.5 μM) of 15/18 was more effective than that of adefovir (8.5 μM).

Compound 15/18 was also evaluated against entecavir resistant clone (L180M+S202I+M202V) in which compound 5 demonstrated anti-HBV activity ($EC_{50}$ 0.67 μM) similar to that of the wild-type virus while in case of entecavir there is significant decrease its antiviral potency ($EC_{50}$ 1.2 μM) (FIG. 11, Table 2).

Molecular Modeling

Figure 14A:
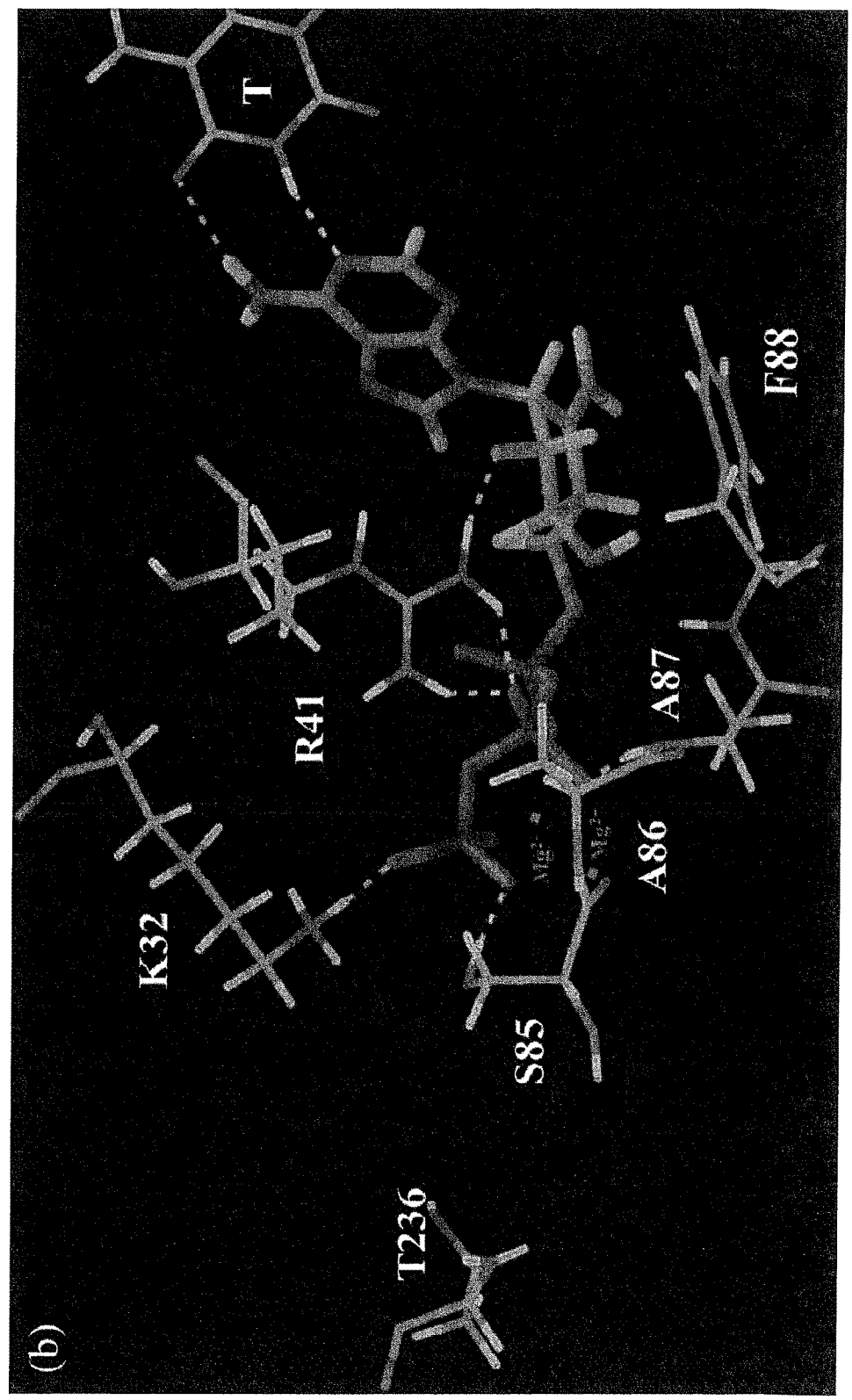

It was of interest to know how the compound 15/18 demonstrated the favorable anti-HBV activity in comparison to that of adefovir. Therefore, molecular modeling studies were conducted to obtain the insight of the molecular mechanism of compound 15/18 by using the Schrodinger module (1-Second set of references). The homology model of HBV RT was constructed based on the published X-ray crystal structure of HIV reverse transcriptase (PDB code: 1RTD), which was previously used for molecular mechanism studies of several anti-HBV nucleosides (17). In the homology model of HBV polymerase, the relative position of α-, β- and γ-phosphates of compound 15/18 with respect to the catalytic triad were assumed to occupy the similar position to the dNTP in the crystal structure of the HIV-1 RT-DNA-dNTP complex. The molecular docking of compound 15/18 shows that the triphosphate forms all the network of hydrogen bonds with the active site residues, S85, A86, A87, R41, K32 (FIG. 14a). The γ-phosphate of 15/18 maintains a critical H-bonding with the OH of S85 with connection of hydrogen bonds between S85 and N236. Generally, the N236T mutant loses the hydrogen bond to S85, which results in destabilization of the S85 to γ-phosphate interaction, thus causes resistance. However, compound 15/18 (as its triphosphate) maintains a critical H-bonding with S85 (FIG. 14b) similar to that as observed in WT (FIG. 14a).

Figure 14B:
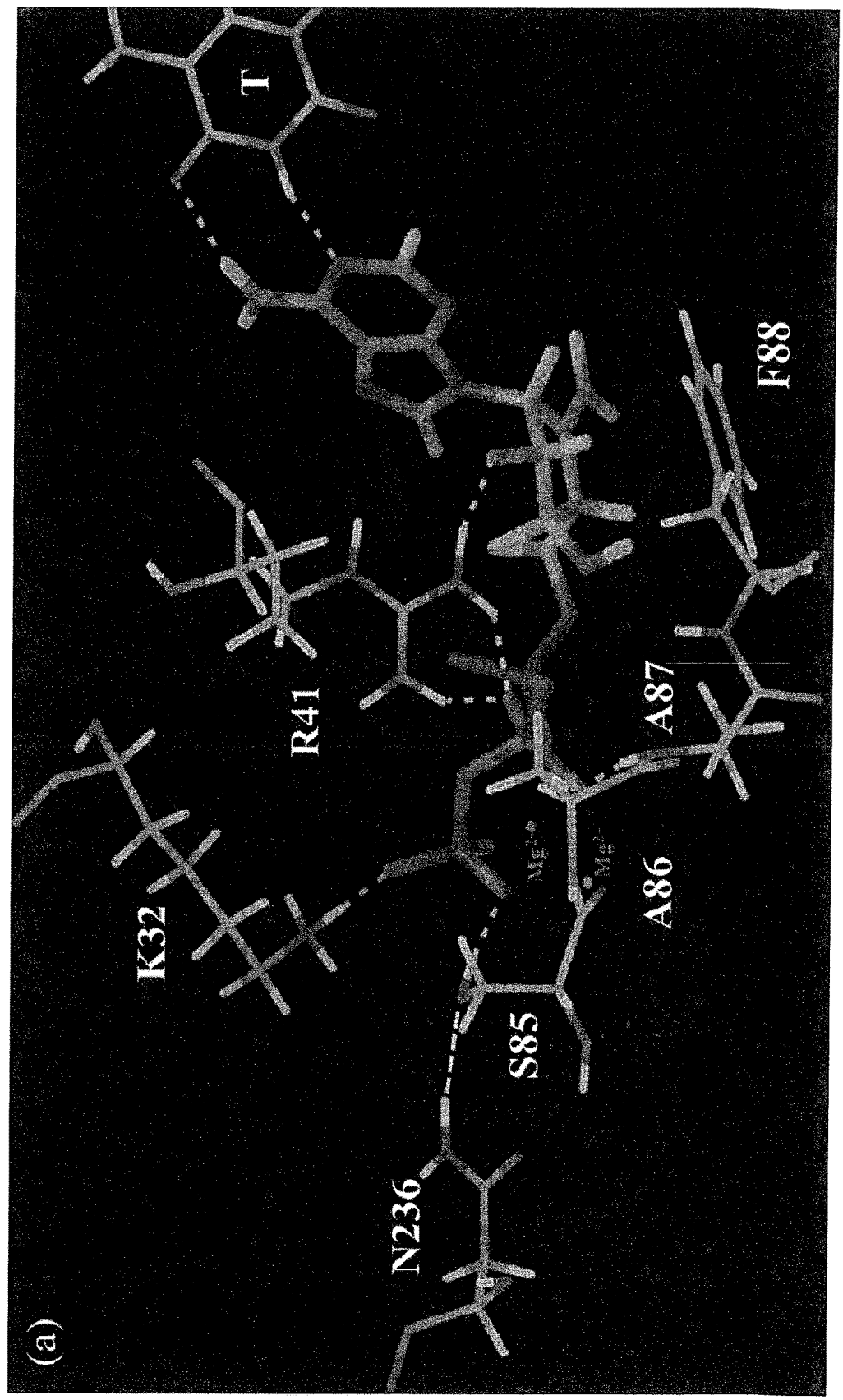

The carbocyclic ring with an exocyclic alkene of 15/18 occupies the hydrophobic pocket (residues F88, L180 and M204) and makes the favorable van der Waals interaction with F88 (FIGS. 14a & 14b). The 2'-fluorine substituent in the carbocyclic ring of 5 appears to promote an additional binding with R41 as shown in FIGS. 14a & 14b, which corroborates with the antiviral activity of 15/18 shown in FIG. 10, Table 1. Overall, the modeling studies can qualitatively explain the favorable anti-HBV activity of the newly discovered compound 15/18 in WT (FIG. 14a) as well as against adefovir resistant mutant, N236T (FIG. 14b). These modeling studies are informative, and therefore, more quantitative calculation is warranted in the future.

In summary, a novel carbocyclic adenosine derivative 15/18 (FMCA) and its monophosphate prodrug 15P/18P (FMCAP) were synthesized, and their anti-HBV activity were evaluated. From these studies, both the nucleoside and the prodrug demonstrated significant anti-HBV activity against both the wild-type as well as all the major nucleoside-resistant HBV mutants. In view of these promising anti-HBV activities, low mitochondrial and cellular toxicity as well as the stability against adenosine deaminase, further biological and biochemical studies of the nucleoside 15/18 and its prodrug 15P/18P are planned to corroborate the in vitro activity in vivo and assess the full potential of these agents as anti-HBV agents.

The present invention is now described, purely by way of illustration, in the following examples. It will be understood by one of ordinary skill in the art that these examples are in no way limiting and that variations of detail can be made without departing from the spirit and scope of the present invention.

EXAMPLES

Experimental (Chemical Synthesis)

General Methods.

Melting points were determined on a Mel-temp II apparatus and were uncorrected. Nuclear magnetic resonance spectra were recorded on a Varian Mercury 400 spectrometer at 400 MHz for $^1$H NMR and 100 MHz for $^{13}$C NMR or Varian Inova 500 spectrometer at 500 MHz for $^1$H NMR and 125 MHz for $^{13}$C NMR with tetramethylsilane as the internal standard. Chemical shifts (□) are reported as s (singlet), d (doublet), t (triplet), q (quartet), m (multiplet), or bs (broad singlet). UV spectra were recorded on a Beckman DU-650 spectrophotometer. Optical rotations were measured on a Jasco DIP-370 digital polarimeter. High resolution mass spectra were recorded on a Micromass Autospec high-resolution mass spectrometer. TLC was performed on Uniplates (silica gel) purchased from Analtech Co. Column chromatography was performed using either silica gel-60 (220-440 mesh) for flash chromatography or silica gel G (TLC grade, >440 mesh) for vacuum flash column chromatography. Elemental analyses were performed by Atlantic Microlab Inc., Norcross, Ga.

(−)-(3aR,4S,6R,6aR)-4-(benzyloxy)-6-(tert-butoxymethyl)-2,2-dimethyl-5-methylenetetrahydro-3aH-cyclopenta[d][1,3]dioxole (4)

To a mixture of compound 1 (8.4 g, 34.6 mmol)[33,34,40] in THF solution lithium diisopropylamine (2.0 M solution, 19.1 mL, 38.1 mmol) was added slowly at −78° C. After stirring at the same temperature for 3 h, Eshenmoser's salt (25.9 g, 138.4 mmol) was added in one portion. The mixture was stirred for additional 3 h at the same temperature and overnight at room temperature. Then iodomethane (108.8 mL, 1.73 mol) was added and stirred for 4 h at room temperature before quenching with 10% aqueous $NaHCO_3$ solution (100 mL). The mixture was stirred for 1 h and extracted with diethyl ether (2×400 mL). The combined ether extracts were washed with 10% aqueous $NaHCO_3$ followed by brine and dried over anhydrous $Na_2SO_4$, filtered and concentrated in vacuum. The residue was purified by vacuum silica gel column chromatography (EtOAc:Hexanes=1:30 to 1:10) to give an oil (4.6 g) which was dissolved in MeOH and treated with $CeCl_3 \cdot 7H_2O$ (7.5 g, 19.6 mmol) for 10 min at room temperature. After cooling down to −78° C., $NaBH_4$ (0.75 g, 20.0 mmol) was added slowly. The reaction was kept at the same temperature for 20 min and quenched with HOAc. Solvent was removed in vacuo and the residue was dissolved in EtOAc and washed with $H_2O$ and brine, dried over $Na_2SO_4$. The solvent was removed under reduced pressure and the residue was purified by vacuum silica gel column chromatography (EtOAc:Hexanes=1:30 to 1:10) to give white solid (4.0 g) which was used directly for next step. White solid ontained from last step (8.0 g, 31.2 mmol) was dissolved in THF and treated with NaH (60%, 1.62 g, 40.5 mmol) for 15 min at room temperature. Benzyl bromide (4.81 mL, 40.5 mmol) and tetrabutylammonium iodide (TBAI) were added subsequently and the mixture was stirred for 3.5 h at 40° C. After quenching with ice/water, the mixture was taken into $Et_2O$ and washed with $H_2O$ and brine, dried over $Na_2SO_4$. The solvent was removed under reduced pressure and the residue was purified by vacuum silica gel column chromatography (EtOAc:Hexanes=1:30 to 1:20) to give desired compound 4 (9.7 g, 43% from 1). $[\alpha]^{24}_D$ −121.09° (c 0.83, $CHCl_3$); $^1H$ NMR (500 MHz, $CDCl_3$) δ 7.43-7.26 (m, 5H), 5.28 (d, J=1.0 Hz, 1H), 5.07 (t, J=1.0 Hz, 1H), 4.83 (d, J=12.0 Hz, 1H), 4.68 (d, J=13.0 Hz, 1H), 4.56 (t, J=5.5 Hz, 1H), 4.44 (t, J=1.0 Hz, 1H), 4.32-4.30 (m, 1H), 3.42 (dd, J=4.0 and 8.5 Hz, 1H), 3.21 (dd, J=5.0 and 8.5 Hz, 1H), 2.59-2.57 (m, 1H), 1.46 (s, 3H), 1.34 (s, 3H), 1.02 (s, 9H); $^{13}C$ NMR (125 MHz, $CDCl_3$) δ 150.6, 138.6, 128.3, 127.8, 127.6, 110.8, 108.9, 81.3, 79.7, 78.5, 72.6, 71.8, 64.5, 49.9, 27.3, 26.9, 25.3; HR-MS Calcd. for $(C_{21}H_{30}O_4+H)^+$ 347.2222, found 347.2225.

(−)-(1S,2S,3S,5R)-3-(benzyloxy)-5-(hydroxymethyl)-4-methylenecyclopentane-1,2-diol (5)

Compound 4 (450 mg, 1.3 mmol) was dissolved in MeOH and treated with 3 N HCl at refluxed temperature for 3.5 h. After neutralized with solid $NaHCO_3$, the solvent was removed and the residue was purified by vacuum silica gel column chromatography ($MeOH:CH_2Cl_2$=1:30 to 1:10) to give triol 5 (280 mg, 85%) as a white solid. mp 122-124° C.; $[\alpha]^{24}_D$ −123.05° (c 0.37, MeOH); $^1H$ NMR (500 MHz, $CD_3OD$) δ 7.46-7.30 (m, 5H), 5.34 (dd, J=1.0 and 3.0 Hz, 1H), 5.21 (s, 1H), 4.77 (d, J=12.0 Hz, 1H), 4.62 (d, J=12.5 Hz, 1H), 4.17-4.14 (m, 2H), 3.95-3.93 (m, 1H), 3.82-3.73 (m, 2H), 2.69-2.66 (m, 1H); $^{13}C$ NMR (125 MHz, $CD_3OD$) δ 148.9, 138.3, 128.0, 127.6, 127.3, 109.1, 80.8, 71.7, 71.0, 70.8, 61.8, 49.6; HR-MS Calcd. for $(C_{14}H_{18}O_4+H)^+$ 251.1283, found 251.1281.

(−)-(6aR,8S,9R,9aR)-8-(benzyloxy)-2,2,4,4-tetraisopropyl-7-methyleneperhydrocyclopenta[f][1,3,5,2,4]trioxadisilocin-9-ol (6)

1,3-Dichloro-1,1,3,3-tetraisopropyldisiloxane (5.5 mL, 16.8 mmol) was added dropwise to a solution of triol 5 (4.0 g, 16.0 mmol) in anhydrous pyridine at −30° C. The reaction mixture was allowed to warm up to room temperature gradually and kept at the same temperature for 2 h. After removing the pyridine in vacuo, the residue was dissolved in EtOAc and washed with $H_2O$ and brine, dried over magnesium sulfate, filtered and concentrated in vacuo. The residue was purified by column chromatography on a silica gel (EtOAc:Hexanes=1:30 to 1:5) to yield the alcohol 6 (6.5 g, 82%) as a syrup. $[\alpha]^{24}_D$ −105.94° (c 0.58, $CHCl_3$); $^1H$ NMR (500 MHz, $CDCl_3$) δ 7.41-7.26 (m, 5H), 5.36 (t, J=2.5 Hz, 1H), 5.11 (t, J=2.5 Hz, 1H), 4.77 (d, J=12.0 Hz, 1H), 4.62 (d, J=12.5 Hz, 1H), 4.18-4.14 (m, 2H), 4.05 (dd, J=4.5 and 12.0 Hz, 1H), 3.78 (dd, J=8.0 and 12.0 Hz, 1H), 2.90-2.88 (m, 1H), 1.08-0.97 (m, 27H); $^{13}C$ NMR (125 MHz, $CDCl_3$) δ 147.3, 138.1, 128.4, 127.6, 127.5, 111.1, 80.2, 74.2, 71.2, 71.1, 64.9, 50.1, 17.6, 17.5, 17.4, 17.3, 17.2, 17.1, 17.0. Anal. Calcd. for $C_{26}H_{44}O_5Si_2$: C, 63.37; H, 9.00. Found: C, 63.64; H, 9.05.

(−)-(6aR,8S,9R,9aR)-8-(benzyloxy)-2,2,4,4-tetraisopropyl-7-methyleneperhydrocyclopenta[f][1,3,5,2,4]trioxadisilocin-9-ol (7)

A solution of compound 6 (2.1 g, 4.3 mmol) and anhydrous pyridine (1.05 mL, 12.6 mmol) in anhydrous $CH_2Cl_2$ (20 mL) was treated with trifluoromethanesulfonic anhydride (0.94 mL, 5.6 mmol) at −78° C. The reaction mixture was allowed to warm up to room temperature gradually and kept at the same temperature for 20 min. After removing the solvent in vacuo, the residue was dissolved in EtOAc and washed with $H_2O$ and brine, dried over magnesium sulfate, filtered and concentrated in vacuo. The residue was dissolved in anhydrous benzene (40 mL), and 18-crown-6 (2.25 g, 8.6 mmol) and cesium acetate (2.47 g, 12.6 mmol) were added. The suspension was heated at 50° C. for 30 min and cooled to room temperature. After removing the solvent, the residue was dissolved in the MeOH and treated with sodium methoxide at room temperature for 3 h and concentrated in vacuo. The residue was purified by column chromatography on a silica gel (EtOAc:Hexanes=1:10 to 1:3) to give 7 (1.7 g, 81% from 6). $[\alpha]^{24}_D$ −76.47° (c 0.82, $CHCl_3$); $^1H$ NMR (500 MHz, $CDCl_3$) δ 7.41-7.26 (m, 5H), 5.34 (t, J=2.5 Hz, 1H), 5.16 (t, J=2.0 Hz, 1H), 4.80 (q, J=12.0 Hz, 2H), 4.12-3.89 (m, 5H), 2.60 (m, 1H), 1.09-0.94 (m, 27H); $^{13}C$ NMR (125 MHz, $CDCl_3$) δ 144.4, 138.6, 128.5, 127.7, 127.6, 111.5, 82.4, 82.3, 77.3, 77.0, 76.8, 76.2, 71.8, 62.7, 49.4, 17.6, 17.5, 17.4, 17.3, 17.2, 17.1, 17.0, 13.6, 13.4, 12.8, 12.6. HR-MS Calcd. for $(C_{26}H_{44}O_5Si_2+H)^+$ 493.2806, found 493.2736.

(−)-(6aR,8S,9R,9aR)-8-(benzyloxy)-9-fluoro-2,2,4,4-tetraisopropyl-7-methylenehexahydrocyclopenta[f][1,3,5,2,4]trioxadisilocine (8)

To a solution of alcohol 6 (6.5 g, 13.2 mmol) in anhydrous $CH_2Cl_2$, (diethylamino)sulfur trifluoride (DAST, 1.84 mL, 13.9 mmol) was added slowly at room temperature. The reaction mixture was quenched with iced H$_2$O after 20 min. The organic layer was collected and the aqueous phase was extracted with dichloromethane. The organic layer was then combined, dried over magnesium sulfate, filtered and concentrated in vacuo. The crude residue was used immediately for the next deprotection step. The analytic sample of 8 was obtained by the purification using column chromatography on a silica gel (EtOAc:Hexanes=1:100 to 1:20). [α]$^{24}_D$ −104.08° (c 0.51, CHCl$_3$); $^1$H NMR (500 MHz, CDCl$_3$) δ 7.39-7.26 (m, 5H), 5.36 (t, J=2.5 Hz, 1H), 5.20 (dd, J=2.5 and 5.0 Hz, 1H), 4.92 (ddd, J=6.0, 7.5 and 55.0 Hz, 1H), 4.78 (d, J=11.5 Hz, 1H), 4.65 (d, J=11.5 Hz, 1H), 4.31-4.26 (m, 1H), 4.23-4.16 (m, 1H), 4.01-3.92 (m, 1H), 1.08-0.94 (m, 27H); $^{13}$C NMR (100 MHz, CDCl$_3$) □ 142.6 (d, J=9.2 Hz), 137.9, 128.4, 127.8, 127.7, 112.7, 103.4 (d, J=189.0 Hz), 80.4 (d, J=21.3 Hz), 73.8 (d, J=19.8 Hz), 71.3, 61.6, 48.8 (d, J=5.3 Hz), 17.5, 17.4, 17.1, 17.0, 16.9, 16.8, 13.4, 13.3, 12.7, 12.5. HR-MS Calcd. for (C$_{26}$H$_{43}$FO$_4$Si$_2$+H)$^+$ 495.2762, found 495.2769.

(−)-[(1R,2Ri3R,4R)-2-(benzoyloxy)-4-(benzyloxy)-3-fluoro-5-methylenecyclopentyl]methyl benzoate (9)

The crude fluorinated compound 8 (directly from last step) was dissolved in THF and treated with acetic acid (3.2 mL, 53.0 mmol) followed by tetrabutylammonium fluoride (TBAF) (40 mL, 40.0 mmol) at room temperature for 1 h. After removing the solvent in vacuo, the residue was dissolved in isopropyl alcohol/chloroform (4:1) co-solvent and washed with H$_2$O. The organic layer was collected, dried over magnesium sulfate, filtered and concentrated in vacuo. The residue was purified by column chromatography on a silica gel (EtOAc:Hexanes=1:4 to 1:1) to give a diol. Diol (1.0 g, 4.0 mmol) was dissolved in anhydrous pyridine and was treated with benzoyl chloride (1.88 mL, 16.0 mmol) at room temperature. Pyridine was removed in vacuo after 4 h and the residue was dissolved in EtOAc. The solution was washed with H$_2$O and brine, dried over magnesium sulfate, filtered and concentrated under in vacuo. The residue was purified by column chromatography on a silica gel (EtOAc:Hexanes=1:20 to 1:3) to give 9 (1.8 g, 61%). [α]$^{24}_D$ −52.71° (c 0.55, CHCl$_3$); $^1$H NMR (500 MHz, CDCl$_3$) □ 8.03-7.26 (m, 15H), 5.68-5.61 (m, 1H), 5.49 (t, J=2.5 Hz, 1H), 5.34 (dd, J=2.5 and 4.5 Hz, 1H), 5.20 (td, J=6.0 and 53.0 Hz, 1H), 4.82 (d, J=11.5 Hz, 1H), 4.73 (d, J=11.5 Hz, 1H), 4.62 (dd, J=5.0 and 10.5 Hz, 1H), 4.55-4.50 (m, 2H), 3.24-3.23 (m, 1H); $^{13}$C NMR (125 MHz, CDCl$_3$) □ 166.3, 165.7, 142.8 (d, J=7.6 Hz), 137.5, 133.4, 133.0, 129.8, 129.6, 129.5, 129.3, 128.5, 128.4, 128.3, 128.0, 127.9, 114.3, 99.9 (d, J=189.9 Hz), 81.2 (d, J=22.0 Hz), 76.2 (d, J=23.8 Hz), 71.7, 64.9, 45.0 (d, J=4.5 Hz). HR-MS Calcd. for (C$_{28}$H$_{25}$FO$_5$+H)$^+$ 461.1764, found 461.1756.

(−)-[(1R,2R,3R,4R)-2-(benzoyloxy)-3-fluoro-4-hydroxy-5-methylenecyclopentyl]methyl benzoate (10)

A solution of compound 9 (1.4 g, 3.0 mmol) in anhydrous CH$_2$Cl$_2$ was treated with boron trichloride (9.1 mL of 1M solution in CH$_2$Cl$_2$, 9.1 mmol) at −78° C. After stirred at the same temperature for 30 min, additional portion of boron trichloride (6.1 mL of 1M solution in CH$_2$Cl$_2$, 6.1 mmol) was added. The reaction was quenched with MeOH at −78° C. after another 15 min and concentrated in vacuo. The residue was purified by column chromatography on a silica gel (EtOAc:Hexanes=1:10 to 1:3) to give 10 (1.0 g, 89%) as a syrup. [α]$^{26}_D$ −53.55° (c 0.25, CHCl$_3$); $^1$H NMR (500 MHz, CDCl$_3$) δ 8.03-7.32 (m, 10H), 5.66 (td, J=6.8 and 16.4 Hz, 1H), 5.49 (t, J=2.0 Hz, 1H), 5.32 (dd, J=2.0 and 4.4 Hz, 1H), 4.96 (td, J=6.8 and 54.4 Hz, 1H), 4.80 (m, 1H), 4.64-4.52 (m, 2H), 3.21 (m, 1H), 2.66 (d, J=7.0 Hz, D$_2$O exchangeable, 1H); $^{13}$C NMR (125 MHz, CDCl$_3$) δ 166.3, 165.8, 144.4 (d, J=8.4 Hz), 133.4, 133.1, 129.8, 129.6, 129.2, 128.4, 128.3, 113.1, 99.9 (d, J=191.3 Hz), 75.3, 75.2, 75.1, 75.0, 65.4, 44.8 (d, J=3.8 Hz). Anal. Calcd. for C$_{21}$H$_{19}$FO$_5$: C, 68.10; H, 5.17. Found: C, 67.78; H, 5.27.

(1R,3R,4R,5R)-5-(benzoyloxy)-3-(6-chloro-9H-9-purinyl)-4-fluoro-2-hydroxy-2-(hydroxymethyl)cyclopentyl]methyl benzoate (12)

To a solution of compound 10 (1.07 g, 2.89 mmol), triphenylphosphine (TPP, 1.13 g, 4.33 mmol) and 6-chloropurine (0.67 g, 4.33 mmol) in anhydrous THF (20 mL) and diisopropyl azodicarboxylate (DIAD, 0.89 mL, 4.33 mmol) was added at 0° C. during 5 min. The reaction was allowed to warm up to room temperature and kept for 1 h. The reaction was quenched by adding MeOH (1 mL) and evaporated in vacuo. The residue was purified by column chromatography on a silica gel (EtOAc:Hexanes=1:4 to 1:2) to give a coupling nucleoside 11 as a mixture which was contaminated with the reduced DIAD species. The crude compound 11 (660 mg) was dissolved acetone/H$_2$O (15 mL/2.5 mL) and treated with osmium tetroxide (1.3 mL 5% H$_2$O solution)/NMO (480 mg) for 24 h. The reaction mixture was quenched with saturated sodium thiosulfate aqueous solution. The organic solution was removed in vacuo and the aqueous phase was extracted with isopropyl alcohol/chloroform (4:1) co-solvent. The organic layer was collected and dried over Na$_2$SO$_4$ and filtered. The filtrate was concentrated in vacuo and the residue was purified by column chromatography on a silica gel (MeOH:CH$_2$Cl$_2$=1:60 to 1:40) to give compound 12 as a mixture of diastereomers (640 mg, 41% from 10). Major isomer: $^1$H NMR (500 MHz, CD$_3$OD) δ 8.80 (d, J=5.0 Hz, 1H), 8.78 (s, 1H), 7.95-7.11 (m, 10H), 6.10 (ddd, J=3.0, 12.5 and 17.5 Hz, 1H), 5.80 (dd, J=10.0 and 35.0 Hz, 1H), 5.38 (ddd, J=3.0, 10.5 and 67.5 Hz, 1H), 4.80 (m, 2H), 3.73 (d, J=14.5 Hz, 1H), 3.40 (d, J=14.5 Hz, 1H), 3.00 (m, 1H); $^{13}$C NMR (100 MHz, CDCl$_3$) 166.4, 165.6, 153.1, 151.8, 151.7, 149.9, 148.2, 148.1, 129.4, 129.1, 128.2, 127.9, 93.1 (d, J=193.1 Hz), 80.8, 79.3 (d, J=26.2 Hz), 62.8, 61.9 (d, J=5.0 Hz), 60.2 (d, J=13.4 Hz), 48.6 (d, J=5.6 Hz). HR-MS Calcd. for (C$_{26}$H$_{22}$ClFN$_4$O$_6$+H)$^+$ 541.1290, found 541.1290.

[(1R,3R,4R,5R)-3-(6-amino-9H-9-purinyl)-5-(benzoyloxy)-4-fluoro-2-hydroxy-2-(hydroxymethyl)cyclopentyl]methyl benzoate (13)

Nucleoside 12 (620 mg, 1.15 mmol) in anhydrous DMF was treated with sodium azide (750 mg, 11.5 mmol) at 70-80° C. for 1.5 h. The volatile was removed in vacuo and the residue was dissolved in isopropyl alcohol/chloroform (4:1) co-solvent and washed with H$_2$O, dried over Na$_2$SO$_4$ and evaporated to dryness. The resulting crude azide compound was dissolved in EtOH and treated with Pd/C (200 mg) under H$_2$ atmosphere at 40° C. for 3 h. After removing the solid, the filtrate was evaporated and the residue was purified by column chromatography on a silica gel (MeOH:CH$_2$Cl$_2$=1:40 to 1:20) to give desired adenosine analogue 13 (370 mg, 62%) as a mixture of diastereomers. Major isomer: UV (MeOH) λ$_{max}$ 259.0 nm; $^1$H NMR (500 MHz, CD$_3$OD) δ 8.43 (d, J=4.0 Hz, 1H), 8.29 (s, 1H), 7.99-7.16 (m, 10H), 6.11 (ddd, J=2.5, 9.5 and 14.5 Hz, 1H), 5.59 (dd, J=8.0 and 29.0 Hz, 1H), 5.35 (ddd, J=2.5, 8.5 and 43.5 Hz, 1H), 4.89 (m, 2H), 3.72 (d, J=11.0 Hz, 1H), 3.50 (d, J=11.0 Hz, 1H), 3.00 (m, 1H); $^{13}$C NMR (100 MHz, CDCl$_3$) δ166.4, 165.6, 156.0, 152.4, 150.5, 142.8, 142.7, 133.1, 132.7, 129.4, 129.1, 128.2, 127.8, 117.7, 93.3 (d, J=193.1 Hz), 80.8, 79.4 (d, J=26.2 Hz), 63.0, 61.9 (d, J=17.6 Hz), 60.3, 48.9 (d, J=5.2 Hz). HR-MS Calcd. for (C$_{26}$H$_{25}$FN$_5$O$_6$+H)$^+$ 522.1789, found 522.1774.

(+)-[(1R,3R,4R,5R)-3-(6-amino-9H-9-purinyl)-5-(benzoyloxy)-4-fluoro-2-methylenecyclopentyl] methyl benzoate (14)

Compound 13 (260 mg, 0.50 mmol) was dissolved in moist acetonitrile (9 μL H$_2$O was added into 10 mL anhydrous acetonitrile) and cooled to −30° C. Excess 1-bromocarbonyl-methylethylacetate (0.54 mL, 3.68 mmol) was added dropwise into the mixture and allowed to warm up to room temperature. After stirring at room temperature for 1 h, the reaction mixture was again cooled to −30° C. and additional 1-bromocarbonyl-methylethylacetate (0.2 mL, 1.47 mmol) was added. Crushed ice was added to quenched the reaction and neutralized with saturated NaHCO$_3$ (20 mL) solution and extracted with EtOAc (100 mL×2). The combined organic layer was washed with brine, dried over Na$_2$SO$_4$ and filtered. The filtrate was concentrated in vacuo and the residue was dissolved in anhydrous DMF and treated with activated zinc (c.a. 2.0 g) and HOAc (0.2 mL) and stirred at room temperature for 8 h. The volatile was removed in vacuo and the residue was dissolved in isopropyl alcohol/chloroform (4:1) co-solvent and washed with saturated NaHCO$_3$ (15 mL) solution, H$_2$O and brine. The organic layer was collected and dried over Na$_2$SO$_4$ and filtered. The filtrate was concentrated in vacuo and the residue was purified by column chromatography on a silica gel (EtOAc:Hexanes=2:1 to 4:1) to give exo-cyclic alkene nucleoside 14 (165.0 mg, 68%) as a white solid. mp: 195-198° C. (dec.) [□]$^{25}_D$ +77.66° (c 0.27, CHCl$_3$); UV (MeOH) λ$_{max}$ 231.0, 259.0 nm; $^1$H NMR (400 MHz, CDCl$_3$) δ 8.40 (s, 1H), 8.12-8.06 (m, 2H), 7.94 (d, J=3.6 Hz, 1H), 7.65-7.44 (m, 3H), 6.0 (dd, J=2.4 and 33.2 Hz, 1H), 5.86 (br, 2H, D$_2$O exchangeable), 5.75 (d, (d, J=14.8 Hz, 1H), 5.50 (s, 1H), 5.21 (dd, J=4.0 and 50.8 Hz, 1H), 4.98 (d, J=1.2 Hz, 1H), 4.82-4.64 (m, 1H), 4.66-4.61 (m, 1H), 3.42 (m, 1H); $^{13}$C NMR (100 MHz, CDCl$_3$) δ 166.4, 165.0, 155.5, 153.2, 150.5, 144.4, 140.9, 140.8, 133.8, 133.3, 130.0, 129.7, 129.6, 128.7, 128.6, 128.5, 118.8, 113.2, 93.6 (d, J=184.4 Hz), 75.8 (d, J=29.0 Hz), 64.4 (d, J=3.1 Hz), 58.3 (d, J=17.5 Hz), 46.5. HR-MS Calcd. for (C$_{26}$H$_{22}$FN$_5$O$_4$+H)$^+$ 488.1734, found 488.1731.

(+)-(1R,2R,3R,5R)-3-(6-amino-9H-9-purinyl)-2-fluoro-5-(hydroxymethyl)-4-methylenecyclopentan-1-ol (15)

Diisobutylaluminum hydride (DIBAL-H, 1.6 mL, 1.0 M in toluene) was added slowly into the solution of compound 14 (160.0 mg, 0.33 mmol) in anhydrous CH$_2$Cl$_2$ at −78° C. After 30 min at the same temperature, the reaction was diluted with isopropyl alcohol/chloroform (4:1) co-solvent (30 mL) and saturated potassium sodium tartrate solution (10 mL) was added. The mixture was stirred at room temperature for 2 h and the organic layer was collected. The aqueous layer was extracted with isopropyl alcohol/chloroform (4:1) co-solvent (3×10 mL) and organic layer were combined, dried over Na$_2$SO$_4$ and filtered. The filtrate was concentrated in vacuo and the residue was purified by column chromatography on a silica gel (MeOH:CH$_2$Cl$_2$=1:20 to 1:10) to give adenosine analogue 15 (70.0 mg, 76%) as a white solid. mp: 215-218° C. (dec.) [α]$^{25}_D$ +151.80° (c 0.23, CHCl$_3$) UV (H$_2$O) λ$_{max}$ 259.0 nm (c 13998, pH 2), 260.0 nm (c 15590, pH 7), 260.0 nm (ε 15579, pH 11); $^1$H NMR (400 MHz, CDCl$_3$) δ 8.22 (s, 1H), 8.06 (d, J=2.4 Hz, 1H), 5.86 (dd, J=2.4 and 25.6 Hz, 1H), 5.42 (t, J=2.4 Hz, 1H), 4.93 (td, J=3.2 and 52.4 Hz, 1H), 4.92 (s, 1H, partially buried inside the H$_2$O peak), 4.40 (td, J=3.2 and 10.8 Hz, 1H), 3.88-3.76 (m, 2H), 2.78 (m, 1H); $^{13}$C NMR (100 MHz, CDCl$_3$) δ 156.0, 152.5, 149.9, 146.1 (d, J=1.0 Hz), 141.1 (d, J=5.2 Hz), 117.9, 111.8, 95.9 (d, J=186.0 Hz), 72.9 (d, J=22.9 Hz), 61.8 (d, J=3.4 Hz), 57.6 (d, J=17.2 Hz), 51.1. Anal. Calcd. for C$_{12}$H$_{14}$FN$_5$O$_2$: C, 51.61; H, 5.05; N, 25.08. Found: C, 51.74; H, 5.09; N, 24.92.

Compound 18 (FIG. 5)

Compound 18 (identical to compound 15 of scheme 2, but synthesized by the alternative route(s) presented in FIG. 5) was synthesized following one or more of the approaches which are set forth in attached FIG. 5. Selected analytical data for compound 18 was identical for that of compound 15, above.

Experimental Protocol for Compounds 15P/18P and 15PI/18PI

N-Methylimidazole (NMI, 5.0 mmol) was added to a stirring suspension of FMCA (1 mmol) in dry THF under argon atmosphere at −78° C. The appropriate substituted chlorophenylphosphoryl-L-alaninate (2P or 3P, 3.0 mmol) dissolve in THF was added dropwise, slowly heated up to room temperature and continue stirred over night at rt. Volatiles was evaporated, and the residue was dissolved in dichloromethane (DCM) and washed with 0.5 M HCL. The organic layer dried over Na$_2$SO$_4$ filtered, reduced to dryness, and purified by flash chromatography to give the prodrug of FMCA (15/18 & 15P/18P).

Analytical data of compound 15P/18P $^1$H NMR (500 Mz, CD$_3$OD) d 8.35 (s, 1H), 7.86 (d, J=3.0 Hz, 1H), 7.34-7.15 (m, 5H), 5.95 (m, 3H), 5.26 d, J=8.0 Hz, 1H), 5.01-4.90 (m, 1H), 4.83 (s, 1H), 4.50-4.41 (m, 2H), 4.25-4.04 (m, 3H), 3.71 (s, 3H), 3.07 (s, 1H), 1.40 (d, J=6.5 Hz, 3H); $^{19}$F NMR (500 MHz, CDCl$_3$) δ −192.86 (m, 1F); $^{13}$C NMR (125 MHz, CD$_3$OD) d171, 159.0, 156.5, 152.5, 150.4, 142.9, 130.1, 121.2, 120.3, 106.7, 102.4, 72.2, 71.1, 62.3, 51.9, 46.3, 43.9, 19.1; $^{31}$P NMR (CDCl$_3$, 202 MHz): δ 2.67, 2.99. Anal. Calcd. For C$_{22}$H$_{26}$FN$_6$O$_6$P.0.5H$_2$O: C, 49.91; H, 5.14; N, 15.87; Found C, 49.84; H, 5.06; N, 15.22.

Analytical Data of compound 15PI/18PI $^1$H NMR (500 Mz, CD$_3$OD) d 8.36 (s, 1H), 7.84 (d, J=30.0 Hz, 1H), 7.34-7.07 (m, 5H), 5.94 (d, J=23 Hz, 1H), 5.76 (bs, 2H NH$_2$), 5.30 (m, 1H), 5.04-4.86 (m, 3H), 4.50-4.44 (m, 2H), 4.21 (m, 1H), 4.11-3.80 (m, 3H), 3.09 (s, 1H), 1.40 (d, J=14.5 Hz, 3H), 1.28 (d, J=14.0 Hz, 6H); $^{19}$F NMR (500 MHz, CDCl$_3$) δ −192.96 (m, 1F); $^{31}$P NMR (CDCl$_3$, 202 MHz): δ 2.84, 2.32.

Antiviral Assay.

Drug susceptibility assays were performed as previously described. Cytotoxicity assays in PBM, CEM and Vero cells were conducted as previously described. Two compounds were used for testing, the first, an adenine nucleoside analog which contained hydroxyl groups at R$^1$ and R$^{1a}$ on the sugar portion of the molecule (compound 15/18) and the second, a prodrug nucleoside compound 15P/18P which is based upon compound 15/18 which contained a phosphoramidate group on R$^1$ (R$^{1a}$ was H) containing a phenyl group as R$^6$ and B' was an amino acid group derived from alanine, where R$^8$ was methyl and R'' was a methyl group, forming a methyl ester. These compounds were tested in a standard HBV assay in the laboratory of Dr. Brent Korba. The following results were obtained. Note that the compounds according to the present invention tested were more than 1000 fold more potent than was 3TC in this assay. The prodrug compound (second compound tested where $R^1$ was a phosphoramidate group $R^6$=phenyl and B' was derived from alanine and contained a methyl ester ($R^8$ is methyl and R" is methyl) was more than 10 times more active than the compound where both $R^1$ and $R^{1a}$ are H.

HBV Assay Results

| Test Number | CC50 | EC50 | EC90 | SI | Control: 3TC (µM) EC50 |
|---|---|---|---|---|---|
| 1 | >300 | 0.548 | 6 | >50 | 2421 |
| 2 | >300 | 0.062 | 0.462 | >649 | 2421 |

As previously described, Compound 15/18 was also tested against wild-type and drug resistant forms of HBV. The testing is described above and the results are presented in Table 1, which is set forth in attached FIG. 10 hereof.

Figure 12:
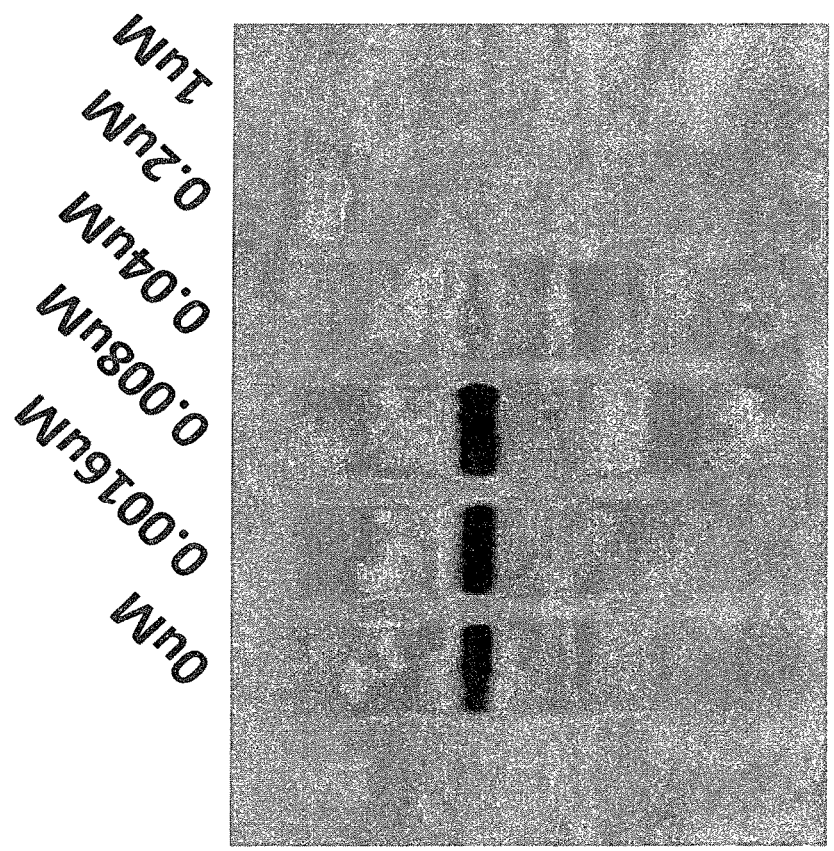
Figure 12:
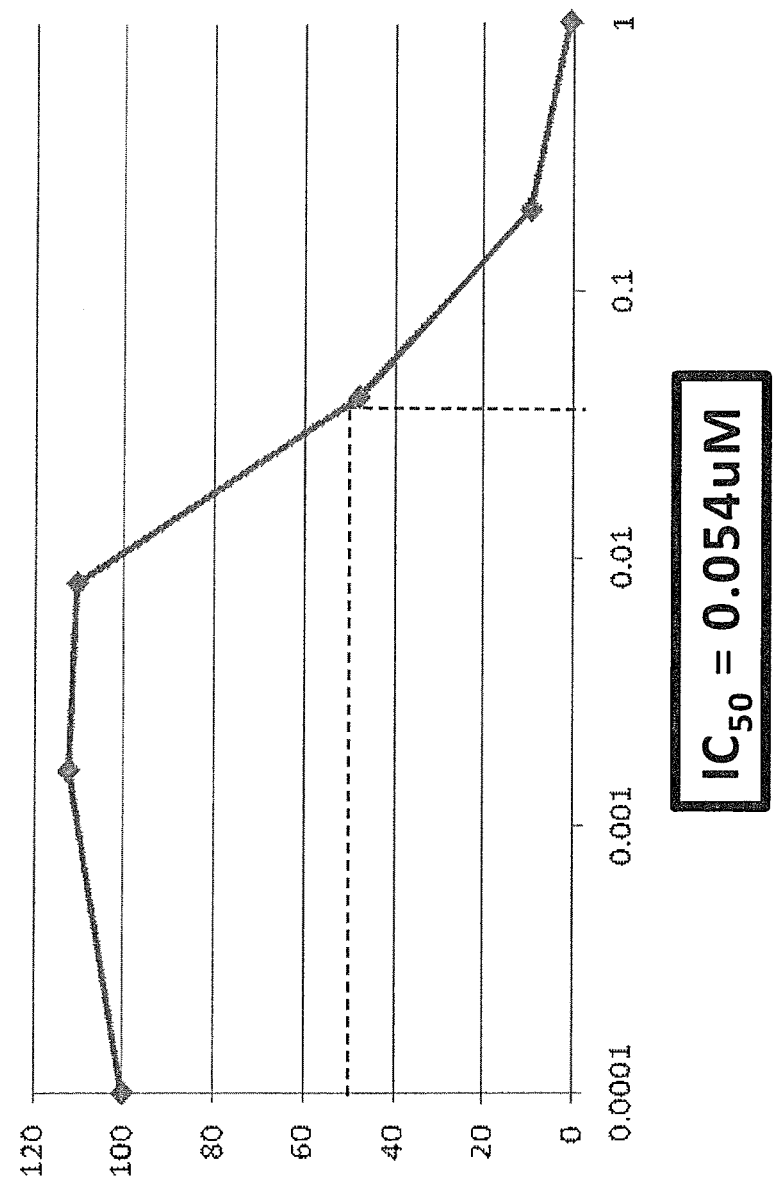

A mono-phosphate prodrug can be useful not only to bypass the rate limiting initial phosphorylation step by the nucleoside kinase, thereby to increase the antiviral potency, but also it may potentially target the liver. Therefore, a phosphoramidite, compound 15P/18P was also synthesized. In separate antiviral evaluation experiments, it was observed that the anti-HBV potency of 15P/18P in vitro was enhanced 7- and 13-fold in the $EC_{50}$ and $EC_{90}$ value, respectively, against WT HBV in comparison to the parent compound 15/18 without significant increase of cellular toxicity (Table 2, FIG. 11). The mono-phosphate prodrug 15P/18P ($IC_{50}$=0.05 µM) was also evaluated against HBV genotype C entecavir resistant clone (L180M+M204V+S202G) in Huh7 cells (16) as shown in FIG. 11, Table 2, and interestingly, the compounds 15/18 FMCA and 15P/18P FMCA monophosphate prodrug still maintain the antiviral potency against the entecavir mutant. FIG. 12 shows the anti-HBV activity of Prodrug 15P/18P against HBV genotype C entecavir resistant clone (L180M+S202G+M204V) in Huh7 cells.

The FMCA monophosphate prodrug compound (15P/18P) was also tested in chimeric mice for activity. In these in vivo studies, FMCA monophosphate prodrug 15P/18P was shown to be active against wild-type HBV with 2 log viral load down (FIG. 15). In further in vivo studies (mice), ETV (entecavir) is found to be inactive against entecavir resistant HBV mutant ((L180M+M204V+S202G) (FIG. 16A), while in contrast, FMCA monophosphate prodrug (15P/'8P) was shown to be active against entecavir resistant HBV mutant (L180M+M204V+S202G) with 1 log viral load down (FIG. 16B). These studies evidence in vivo efficacy of the compounds according to the present invention as represented by FMCA (compound 15/18) and especially the FMCA monophosphate prodrug compound (15P/18P).

Mitochondrial Study

Mitochondrial toxicity studies in HepG2 cells by measuring the lactic dehydrogenase release (13) suggest that FMCA 15/18 did not exhibit any significant toxicity up to 100 µM as in lamivudine (3TC), while azidothymidine (AZT) shows significant toxicity (FIG. 13). In addition, deamination studies with adenosine deaminase from calf thymus indicated that compound 15/18 was completely stable (20).

Molecular Modeling Study

Conformational search: The initial conformations of compound 15/18 and entecavir analog 16 were constructed by builder module in MACROMODEL®, version 8.5 (Schrodinger, Inc.) The Monte Carlo conformational search was performed in 5,000-step, in the presence of GB/SA water model using MMFFs force field in MACROMODEL®. Pseudorotation analysis: The online pesudorotation analysis tool PROSIT (http://cactus.nci.nih.gov/prosit/) was used to calculated all the pseudorotation parameters.[51]

The following conclusions, inter alia can be drawn about the present invention:

1. The present compounds and their monophosphate prodrugs are active against lamivudine, adeforvir and entecavir resistant mutants in vitro;
2. The 2'-F moiety appears to strengthen the binding of FMCA-TP to HBV polymerase by a hydrogen bond and these compounds are particularly active within this series;
3. The present compounds, including FMCA, exhibit low cellular and mitochondrial toxicity and are useful for prophylaxis as well as therapy;
4. In preliminary in vivo efficacy studies in chimeric mice infected with lamivudine-adeforvir-entecavir triple mutant, the FMCA-MP prodrug exhibited antiviral activity while entecavir did not, an unexpected result showing that the present compounds are particularly useful in therapy, including inclusion in a therapeutic cocktail against drug resistant HBV and resulting infections.

REFERENCES (FIRST SET)

1. Mast, E. E.; Alter, M. J.; Margolis, H. S. Strategies to prevent and control hepatitis B and C virus infections: a global perspective. *Vaccine* 1999, 17, 1730-3.
2. Lee, W. M. Hepatitis B virus infection. *N Engl J Med* 1997, 337, 1733-45.
3. Perrillo, R. P.; Schiff, E. R.; Davis, G. L.; Bodenheimer, H. C., Jr.; Lindsay, K.; Payne, J.; Dienstag, J. L.; O'Brien, C.; Tamburro, C.; Jacobson, I. M.; et al. A randomized, controlled trial of interferon alfa-2b alone and after prednisone withdrawal for the treatment of chronic hepatitis B. The Hepatitis Interventional Therapy Group. *N Engl J Med* 1990, 323, 295-301.
4. Wong, D. K.; Cheung, A. M.; O'Rourke, K.; Naylor, C. D.; Detsky, A. S.; Heathcote, J. Effect of alpha-interferon treatment in patients with hepatitis B e antigen-positive chronic hepatitis B. A meta-analysis. *Ann Intern Med* 1993, 119, 312-23.
5. Kim, W. R.; Benson, J. T.; Hindman, A.; Brosgart, C.; Fortner-Burton, C. Decline in the need for liver transplantation for end stage liver disease secondary to hepatitis B in the US. *Hepatology* 2007, 46(Suppl), 238A.
6. Tuttleman, J. S.; Pourcel, C.; Summers, J. Formation of the pool of covalently closed circular viral DNA in hepadnavirus-infected cells. *Cell* 1986, 47, 451-60.
7. Zoulim, F. Mechanism of viral persistence and resistance to nucleoside and nucleotide analogs in chronic hepatitis B virus infection. *Antiviral Res* 2004, 64, 1-15.
8. Ghany, M. G.; Doo, E. C. Antiviral resistance and hepatitis B therapy. *Hepatology* 2009, 49, S174-84.
9. Ono, S. K.; Kato, N.; Shiratori, Y.; Kato, J.; Goto, T.; Schinazi, R. F.; Carrilho, F. J.; Omata, M. The polymerase L528M mutation cooperates with nucleotide binding-site mutations, increasing hepatitis B virus replication and drug resistance. *J Clin Invest* 2001, 107, 449-55.

10. Allen, M. I.; Deslauriers, M.; Andrews, C. W.; Tipples, G. A.; Walters, K. A.; Tyrrell, D. L.; Brown, N.; Condreay, L. D. Identification and characterization of mutations in hepatitis B virus resistant to lamivudine. Lamivudine Clinical Investigation Group. *Hepatology* 1998, 27, 1670-7.

11. Dienstag, J. L.; Schiff, E. R.; Wright, T. L.; Perrillo, R. P.; Hann, H. W.; Goodman, Z.; Crowther, L.; Condreay, L. D.; Woessner, M.; Rubin, M.; Brown, N. A. Lamivudine as initial treatment for chronic hepatitis B in the United States. *N Engl J Med* 1999, 341, 1256-63.

12. Lai, C. L.; Chien, R. N.; Leung, N. W.; Chang, T. T.; Guan, R.; Tai, D. I.; Ng, K. Y.; Wu, P. C.; Dent, J. C.; Barber, J.; Stephenson, S. L.; Gray, D. F. A one-year trial of lamivudine for chronic hepatitis B. Asia Hepatitis Lamivudine Study Group. *N Engl J Med* 1998, 339, 61-8.

13. Marcellin, P.; Lau, G. K.; Bonino, F.; Farci, P.; Hadziyannis, S.; Jin, R.; Lu, Z. M.; Piratvisuth, T.; Germanidis, G.; Yurdaydin, C; Diago, M.; Gurel, S.; Lai, M. Y.; Button, P.; Pluck, N. Peginterferon alfa-2a alone, lamivudine alone, and the two in combination in patients with HBeAg-negative chronic hepatitis B. *N Engl J Med* 2004, 351, 1206-17.

14. Yuen, M. F.; Seto, W. K.; Chow, D. H.; Tsui, K.; Wong, D. K.; Ngai, V. W.; Wong, B. C.; Fung, J.; Yuen, J. C.; Lai, C. L. Long-term lamivudine therapy reduces the risk of long-term complications of chronic hepatitis B infection even in patients without advanced disease. *Antivir Ther* 2007, 12, 1295-303.

15. Lai, C. L.; Gane, E.; Liaw, Y. F.; Hsu, C. W.; Thongsawat, S.; Wang, Y.; Chen, Y.; Heathcote, E. J.; Rasenack, J.; Bzowej, N.; Naoumov, N. V.; Di Bisceglie, A. M.; Zeuzem, S.; Moon, Y. M.; Goodman, Z.; Chao, G.; Constance, B. F.; Brown, N. A. Telbivudine versus lamivudine in patients with chronic hepatitis B. N Engl J Med 2007, 357, 2576-88.

16. Angus, P.; Vaughan, R.; Xiong, S.; Yang, H.; Delaney, W.; Gibbs, C.; Brosgart, C.; Colledge, D.; Edwards, R.; Ayres, A.; Bartholomeusz, A.; Locarnini, S. Resistance to adefovir dipivoxil therapy associated with the selection of a novel mutation in the HBV polymerase. *Gastroenterology* 2003, 125, 292-7.

17. Qi, X.; Xiong, S.; Yang, H.; Miller, M.; Delaney, W. E. t. In vitro susceptibility of adefovir-associated hepatitis B virus polymerase mutations to other antiviral agents. *Antivir Ther* 2007, 12, 355-62.

18. Villeneuve, J. P.; Durantel, D.; Durantel, S.; Westland, C.; Xiong, S.; Brosgart, C. L.; Gibbs, C. S.; Parvaz, P.; Werle, B.; Trepo, C.; Zoulim, F. Selection of a hepatitis B virus strain resistant to adefovir in a liver transplantation patient. *J Hepatol* 2003, 39, 1085-9.

19. Curtis, M.; Zhu, Y.; Borroto-Esoda, K. Hepatitis B virus containing the I233V mutation in the polymerase reverse-transcriptase domain remains sensitive to inhibition by adefovir. *J Infect Dis* 2007, 196, 1483-6.

20. Schildgen, O.; Sirma, H.; Funk, A.; Olotu, C.; Wend, U. C.; Hartmann, H.; Helm, M.; Rockstroh, J. K.; Willems, W. R.; Will, H.; Gerlich, W. H. Variant of hepatitis B virus with primary resistance to adefovir. *N Engl J Med* 2006, 354, 1807-12.

21. Hadziyannis, S. J.; Tassopoulos, N. C.; Heathcote, E. J.; Chang, T. T.; Kitis, G.; Rizzetto, M.; Marcellin, P.; Lim, S. G.; Goodman, Z.; Ma, J.; Brosgart, C. L.; Borroto-Esoda, K.; Arterburn, S.; Chuck, S. L. Long-term therapy with adefovir dipivoxil for HBeAg-negative chronic hepatitis B for up to 5 years. *Gastroenterology* 2006, 131, 1743-51.

22. Sherman, M.; Yurdaydin, C.; Sollano, J.; Silva, M.; Liaw, Y. F.; Cianciara, J.; Boron-Kaczmarska, A.; Martin, P.; Goodman, Z.; Colonno, R.; Cross, A.; Denisky, G.; Kreter, B.; Hindes, R. Entecavir for treatment of lamivudine-refractory, HBeAg-positive chronic hepatitis B. *Gastroenterology* 2006, 130, 2039-49.

23. Tenny, D. J.; Pokornowski, K. A.; Rose, B. E.; al., e. Entecavir at five years shows long-term maintenance of high genetic barrier to hepatitis B virus resistance. *Heptol Int* 2008, 2, 302-303.

24. Dienstag, J. L.; Goldin, R. D.; Heathcote, E. J.; Hann, H. W.; Woessner, M.; Stephenson, S. L.; Gardner, S.; Gray, D. F.; Schiff, E. R. Histological outcome during long-term lamivudine therapy. *Gastroenterology* 2003, 124, 105-17.

25. Lok, A. S.; Lai, C. L.; Leung, N.; Yao, G. B.; Cui, Z. Y.; Schiff, E. R.; Dienstag, J. L.; Heathcote, E. J.; Little, N. R.; Griffiths, D. A.; Gardner, S. D.; Castiglia, M. Long-term safety of lamivudine treatment in patients with chronic hepatitis B. *Gastroenterology* 2003, 125, 1714-22.

26. Choi, Y.; Lee, K.; Hong, J. H.; Schinazi, R. F.; Chu, C. K. Synthesis and anti-HIV activity of L-2'-fluoro-2',3'-unsaturated purine nucleosides. *Tetrahedron Lett* 1998, 39, 4437-4440.

27. Chong, Y.; Choo, H.; Choi, Y.; Mathew, J.; Schinazi, R. F.; Chu, C. K. Stereoselective synthesis and antiviral activity of D-2',3'-didehydro-2',3'-dideoxy-2'-fluoro-4'-thionucleosides. *J Med Chem* 2002, 45, 4888-98.

28. Chong, Y.; Gumina, G.; Mathew, J. S.; Schinazi, R. F.; Chu, C. K. 1-2',3'-Didehydro-2',3'-dideoxy-3'-fluoronucleosides: synthesis, anti-HIV activity, chemical and enzymatic stability, and mechanism of resistance. *J Med Chem* 2003, 46, 3245-56.

29. Choo, H.; Chong, Y.; Choi, Y.; Mathew, J.; Schinazi, R. F.; Chu, C. K. Synthesis, anti-HIV activity, and molecular mechanism of drug resistance of L-2',3'-didehydro-2',3'-dideoxy-2'-fluoro-4'-thionucleosides. *J Med Chem* 2003, 46, 389-98.

30. Chu, C. K.; Ma, T.; Shanmuganathan, K.; Wang, C.; Xiang, Y.; Pai, S. B.; Yao, G. Q.; Sommadossi, J. P.; Cheng, Y. C. Use of 2'-fluoro-5-methyl-beta-L-arabinofuranosyluracil as a novel antiviral agent for hepatitis B virus and Epstein-Barr virus. *Antimicrob Agents Chemother* 1995, 39, 979-81.

31. Lee, K.; Choi, Y.; Gullen, E.; Schlueter-Wirtz, S.; Schinazi, R. F.; Cheng, Y. C.; Chu, C. K. Synthesis and anti-HIV and anti-HBV activities of 2'-fluoro-2',3'-unsaturated L-nucleosides. *J Med Chem* 1999, 42, 1320-8.

32. Lee, K.; Choi, Y.; Gumina, G.; Zhou, W.; Schinazi, R. F.; Chu, C. K. Structure-activity relationships of 2'-fluoro-2',3'-unsaturated D-nucleosides as anti-HIV-1 agents. *J Med Chem* 2002, 45, 1313-20.

33. Wang, J.; Jin, Y.; Rapp, K. L.; Bennett, M.; Schinazi, R. F.; Chu, C. K. Synthesis, antiviral activity, and mechanism of drug resistance of D- and L-2',3'-didehydro-2',3'-dideoxy-2'-fluorocarbocyclic nucleosides. *J Med Chem* 2005, 48, 3736-48.

34. Wang, J.; Jin, Y.; Rapp, K. L.; Schinazi, R. F.; Chu, C. K. D- and L-2',3'-didehydro-2',3'-dideoxy-3'-fluoro-carbocyclic nucleosides: synthesis, anti-HIV activity and mechanism of resistance. *J Med Chem* 2007, 50, 1828-39.

35. Zhou, W.; Gumina, G.; Chong, Y.; Wang, J.; Schinazi, R. F.; Chu, C. K. Synthesis, structure-activity relationships, and drug resistance of beta-d-3'-fluoro-2',3'-unsaturated nucleosides as anti-HIV Agents. *J Med Chem* 2004, 47, 3399-408.

36. Bisacchi, G. S.; Chao, S. T.; Bachard, C.; Daris, J. P.; Innaimo, S.; Jacobs, G. A.; Kocy, O.; Lapointe, P.; Martel, A.; Merchant, Z.; Slusarchyk, W. A.; Sundeen, J. E.; Young, M. G.; Colonno, R.; Zahler, R. BMS-200475, a novel carbocyclic 22-deoxyguanosine analog with potent and selective anti-hepatitis B virus activity in vitro. *Bioorg Med Chem Lett* 1997, 7, 127-132.

37. Gaudino, J. J.; Wilcox, C. S. A concise approach to enantiomerically pure carbocyclic ribose analogs. Synthesis of (4S,5R,6R,7R)-7-(hydroxymethyl)spiro[2.4] heptane-4,5,6-triol 7-O-(dihydrogen phosphate). *J Am Chem Soc* 1990, 112, 4374-4380.

38. Takagi, C.; Sukeda, M.; Kim, H. S.; Wataya, Y.; Yabe, S.; Kitade, Y.; Matsuda, A.; Shuto, S. Synthesis of 5'-methyleneariesteromycin and its 2-fluoro derivative with potent antimalarial activity due to inhibition of the parasite S-adenosylhomocysteine hydrolase. *Org Biomol Chem* 2005, 3, 1245-51.

39. Ziegler, F. E.; Sarpong, M. A. Radical cyclization studies directed toward the synthesis of BMS-200475 'entecavir': the carbocyclic core. *Tetrahedron* 2003, 59, 9013-9018.

40. Wang, P.; Agrofoglio, L. A.; Newton, M. G.; Chu, C. K. Chiral Synthesis of Carbocyclic Analogues of L-ribofuranosides. *J Org Chem* 1999, 64, 4173-4178.

41. Corey, E. J.; Winter, R. A. E. A New, Stereospecific Olefin Synthesis from 1,2-Diols. *J Am Chem Soc* 1963, 85, 2677-2678.

42. Ando, M.; Ohhara, H.; Takase, K. A mild and stereospecific conversion of vicinal diols into olefins via 2-methoxy-1,3-dioxolane derivatives. *Chem Letter* 1986, 15, 879-882.

43. Manchand, P. S.; Belica, P. S.; Holman, M. J.; Huang, T. N.; Maehr, H.; Tam, S. Y. K.; Yang, R. T. Syntheses of the anti-AIDS drug 2',3'-dideoxycytidine from cytidine. *J Org Chem* 1992, 57, 3473-3478.

44. Robins, M. J.; Hansske, F.; Low, N. H.; Park, J. I. A mild conversion of vicinal diols to alkenes. Efficient transformation of ribonucleosides into 2'-ene and 2',3'-dideoxynucleosides. *Tetrahedron Lett* 1984, 25, 367-370.

45. Van Aerschot, A.; Everaert, D.; Balzarini, J.; Augustyns, K.; Jie, L.; Janssen, G.; Peeters, O.; Blaton, N.; De Ranter, C.; De Clercq, E.; et al. Synthesis and anti-HIV evaluation of 2',3'-dideoxyribo-5-chloropyrimidine analogues: reduced toxicity of 5-chlorinated 2',3'-dideoxynucleosides. *J Med Chem* 1990, 33, 1833-9.

46. Tassopoulos, N. C.; Volpes, R.; Pastore, G.; Heathcote, J.; Buti, M.; Goldin, R. D.; Hawley, S.; Barber, J.; Condreay, L.; Gray, D. F. Efficacy of lamivudine in patients with hepatitis B e antigen-negative/hepatitis B virus DNA-positive (precore mutant) chronic hepatitis B. Lamivudine Precore Mutant Study Group. *Hepatology* 1999, 29, 889-96.

47. Das, K.; Xiong, X.; Yang, H.; Westland, C. E.; Gibbs, C. S.; Sarafianos, S. G.; Arnold, E. Molecular modeling and biochemical characterization reveal the mechanism of hepatitis B virus polymerase resistance to lamivudine (3TC) and emtricitabine (FTC). *J Virol* 2001, 75, 4771-9.

48. Chong, Y.; Chu, C. K. Understanding the molecular mechanism of drug resistance of anti-HIV nucleosides by molecular modeling. *Front Biosci* 2004, 9, 164-86.

49. Yadav, V.; Chu, C. K. Molecular mechanisms of adefovir sensitivity and resistance in HBV polymerase mutants: a molecular dynamics study. *Bioorg Med Chem Lett* 2004, 14, 4313-7.

50. Langley, D. R.; Walsh, A. W.; Baldick, C. J.; Eggers, B. J.; Rose, R. E.; Levine, S. M.; Kapur, A. J.; Colonno, R. J.; Tenney, D J Inhibition of hepatitis B virus polymerase by entecavir. *J Virol* 2007, 81, 3992-4001.

51. Sun, G.; Voigt, J. H.; Marquez, V. E.; Nicklaus, M. C. Prosit, an online service to calculate pseudorotational parameters of nucleosides and nucleotides. *Nucleosides Nucleotides Nucleic Acids* 2005, 24, 1029-32.

52. Chong, Y.; Chu, C. K. Understanding the unique mechanism of L-FMAU (clevudine) against hepatitis B virus: molecular dynamics studies. *Bioorg Med Chem Lett* 2002, 12, 3459-62.

REFERENCES (SECOND SET)

1. Compound data incorporated into text.
2. Compound data incorporated into text.
3. Chu, C. K., T. Ma, K. Shanmuganathan, C. Wang, Y. Xiang, S. B. Pai, G. Q. Yao, J. P. Sommadossi, and Y. C. Cheng. 1995. Use of 2'-fluoro-5-methyl-beta-L-arabinofuranosyluracil as a novel antiviral agent for hepatitis B virus and Epstein-Barr virus. Antimicrobial agents and chemotherapy 39:979.
4. Crimmins, M. T. 1998. New developments in the enantioselective synthesis of cyclopentyl carbocyclic nucleosides. Tetrahedron 54:9229-9272.
5. Delaney, W. E., S. Locarnini, and T. Shaw. 2001. Resistance of hepatitis B virus to antiviral drugs: current aspects and directions for future investigation. Antiviral chemistry & chemotherapy 12:1-35.
5. Dey, S., and P. Garner. 2000. Synthesis of tert-butoxycarbonyl (Boc)-protected purines. The Journal of Organic Chemistry 65:7697-7699.
6. Ferrero, M., and V. Gotor. 2000. Biocatalytic selective modifications of conventional nucleosides, carbocyclic nucleosides, and C-nucleosides. Chemical Reviews 100: 4319-4348.
7. Ganem, D., and A. M. Prince. 2004. Hepatitis B virus infection—natural history and clinical consequences. New England Journal of Medicine 350:1118-1129.
8. Genovesi, E. V., L. Lamb, I. Medina, D. Taylor, M. Seifer, S. Innaimo, R. J. Colonno, D. N. Standring, and J. M. Clark. 1998. Efficacy of the Carbocyclic 2'-Deoxyguanosine Nucleoside BMS-200475 in the Woodchuck Model of Hepatitis B Virus Infection. Antimicrob. Agents Chemother. 42:3209-3217.
9. Iyer, R. P., Y. Jin, A. Roland, J. D. Morrey, S. Mounir, and B. Korba. 2004. Phosphorothioate Di- and Trinucleotides as a Novel Class of Anti-Hepatitis B Virus Agents. Antimicrob. Agents Chemother. 48:2199-2205.
10. Jin, Y. H., P. Liu, J. Wang, R. Baker, J. Huggins, and C. K. Chu. 2003. Practical synthesis of D- and L-2-cyclopentenone and their utility for the synthesis of carbocyclic antiviral nucleosides against *orthopox* viruses (smallpox, monkeypox, and cowpox virus). The Journal of Organic Chemistry 68:9012-9018.
12. Korba, B. E., and J. L. Gerin. 1992. Use of a standardized cell culture assay to assess activities of nucleoside analogs against hepatitis B virus replication. Antiviral research 19:55-70.
13. Lai, Y., C. M. Tse, and J. D. Unadkat. 2004. Mitochondrial expression of the human equilibrative nucleoside transporter 1 (hENT1) results in enhanced mitochondrial toxicity of antiviral drugs. Journal of Biological Chemistry 279:4490.

14. McGuigan, C., A. Gilles, K. Madela, M. Aljarah, S. Holl, S. Jones, J. Vernachio, J. Hutchins, B. Ames, K. D. Bryant, E. Gorovits, B. Ganguly, D. Hunley, A. Hall, A. Kolykhalov, Y. Liu, J. Muhammad, N. Raja, R. Walters, J. Wang, S. Chamberlain, and G. Henson. 2010. Phosphoramidate ProTides of 2'-C-Methylguanosine as Highly Potent Inhibitors of Hepatitis C Virus. Study of Their in Vitro and in Vivo Properties. Journal of medicinal chemistry 53:4949-4957.
15. Montgomery, J. A., A. T. Shortnacy-Fowler, S. D. Clayton, J. M. Riordan, and J. A. Secrist. 1992. Synthesis and biological activity of 2'-fluoro-2-halo derivatives of 9-.beta.-D-arabinofuranosyladenine. Journal of medicinal chemistry 35:397-401.
16. Mukaide, M., Y. Tanaka, T. Shin-I, M. F. Yuen, F. Kurbanov, O. Yokosuka, M. Sata, Y. Karino, G. Yamada, and K. Sakaguchi. 2010. Mechanism of Entecavir Resistance of Hepatitis B Virus with Viral. Breakthrough as Determined by Long-Term Clinical Assessment and Molecular Docking Simulation. Antimicrobial agents and chemotherapy 54:882.
17. Sharon, A., and C. K. Chu. 2008. Understanding the molecular basis of HBV drug resistance by molecular modeling. Antiviral research 80:339-353.
18. Sharon, A., A. K. Jha, and C. K. Chu. 2010. Clevudine, to Treat Hepatitis B Viral Infection, p. 383-408. In J. Fisher and C. R. Ganellin (ed.), Analogue-based Drug Discovery II. WILEY-VCH Verlag GmbH & Co.: KGaA, Weinheim.
19. Sorrell, M. F., E. A. Belongia, J. Costa, I. F. Gareen, J. L. Grem, J. M. Inadomi, E. R. Kern, J. A. McHugh, G. M. Petersen, and M. F. Rein. 2009. National Institutes of Health consensus development conference statement: management of hepatitis B. Hepatology 49:S4-S12.
20. Stoeckler, J. D., C. A. Bell, R. E. Parks Jr, C. K. Chu, J. J. Fox, and M. Ikehara. 1982. C(2')-substituted purine nucleoside analogs: Interactions with adenosine deaminase and purine nucleoside phosphorylase and formation of analog nucleotides. Biochemical Pharmacology 31:1723-1728.
21. Suzuki, Y., F. Suzuki, Y. Kawamura, H. Yatsuji, H. Sezaki, T. Hosaka, N. Akuta, M. Kobayashi, S. Saitoh, and Y. Arase. 2009. Efficacy of entecavir treatment for lamivudine resistant hepatitis B over 3 years: Histological improvement or entecavir resistance? Journal of gastroenterology and hepatology 24:429-435.
22. Villet, S., A. Ollivet, C. Pichoud, L. Barraud, J.-P. Villeneuve, C. Trépo, and F. Zoulim. 2007. Stepwise process for the development of entecavir resistance in a chronic hepatitis B virus infected patient. Journal of Hepatology 46:531-538.
23. Walsh, A. W., D. R. Langley, R. J. Colonno, and D. J. Tenney. 2010. Mechanistic characterization and molecular modeling of hepatitis B virus polymerase resistance to entecavir. PloS one 5:e9195.
24. Wang, J., Y. Jin, K. L. Rapp, M. Bennett, R. F. Schinazi, and C. K. Chu. 2005. Synthesis, antiviral activity, and mechanism of drug resistance of D- and L-2',3'-didehydro-2',3'-dideoxy-2'-fluorocarbocyclic nucleosides. Journal of medicinal chemistry 48:3736-3748.
25. Yuen, M. F., and C. L. Lai. 2004. Adefovir dipivoxil in chronic hepatitis B infection. Expert Opinion on Pharmacotherapy 5:2361-2367.

The invention claimed is:

1. A nucleoside compound according to the structure:

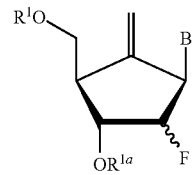

Where B is

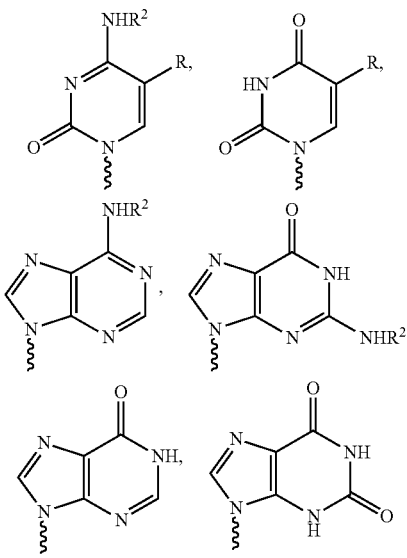

Wherein R is H, $CH_3$,

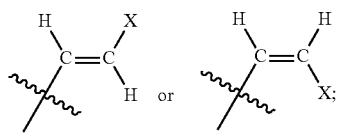

X is H;

$R_a$ is H or a $—C_1-C_4$ alkyl group;

$R^1$ and $R^{1a}$ are each independently, H, an acyl group, a $C_1-C_{20}$ alkyl or ether group, an amino acid residue (D or L), a phosphate, diphosphate, triphosphate, phosphodiester or phosphoramidate group or together $R^1$ and $R^{1a}$ form a carbodiester or phosphodiester group with the oxygen atoms to which they are bonded;

$R^2$ is H, an acyl group, a $C_1-C_{20}$ alkyl or ether group or an amino acid residue (D or L);

Or a pharmaceutically acceptable salt or enantiomer thereof.

2. The compound according to claim 1, wherein $R^{1a}$ is H.

3. The compound according to claim 1 wherein $R^1$ and $R^2$ are each independently H or a $C_2-C_{20}$ acyl group.

4. The compound according claim 1 wherein $R^1$, $R^{1a}$ and $R^2$ are each H.

5. The compound according to claim 1 wherein B is

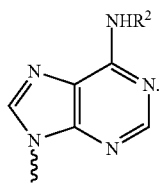

6. The compound according to claim 1 which is represented by the chemical structure:

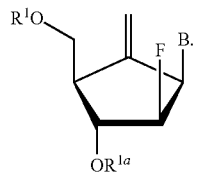

7. The compound according to claim 6 wherein $R^1$, $R^{1a}$ and $R^2$ are each independently H or a $C_2$-$C_{20}$ acyl group.

8. The compound according to claim 1 wherein R is H or F.

9. The compound according to claim 1 wherein $R^{1a}$ is H and $R^1$ and $R^2$ are each independently H or a $C_2$-$C_{20}$ acyl group.

10. The compound according to claim 1 wherein $R^1$ is an acyl group, a phosphate, phosphdiester or phosphoramidate group.

11. The compound according to claim 1 wherein $R^1$ together with the nucleoside to which it is attached forms a group according to the structure:

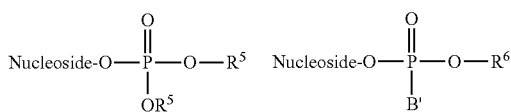

where each $R^5$ and $R^6$ is independently selected from H, a $C_1$ to $C_{20}$ linear, branched or cyclic alkyl group, alkoxyalkyl, aryloxyalkyl, aryl, alkoxy or alkoxycarbonyloxy group, each of which groups may be optionally substituted, with the proviso that at least one $R^5$ group is other than H, or the two $R^5$ groups together form a five- or six-membered heterocyclic group;

B' is a group according to the structure

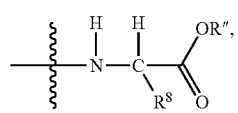

Where $R^8$ is sidechain of an amino acid; and

Each R" is independently a $C_1$ to $C_{20}$ linear, branched or cyclic alkyl or a phenyl or heteroaryl group, each of which groups may be optionally substituted.

12. The compound according to claim 1 wherein $R^1$, together with the nucleoside to which it is attached is a group according to the structure:

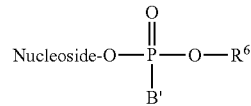

Where $R^6$ is a $C_1$-$C_{20}$ alkyl or an optionally substituted phenyl group;

B' is a group according to the structure

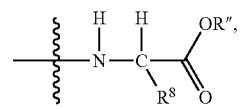

Where $R^8$ is a $C_1$-$C_3$ linear or branch-chained alkyl group; and

R" is a $C_1$-$C_{20}$ linear, cyclic or branch-chained alkyl group or an optionally substituted phenyl group.

13. A compound according to claim 1 wherein $R^2$ and $R^{1a}$ are each independently H or a $C_2$-$C_{20}$ acyl group; and $R^1$ is a

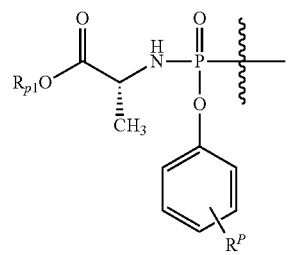

group;

Where $R_{p1}$ is an optionally substituted $C_1$-$C_{20}$ alkyl group; and $R^P$ is H, nitro, cyano, methoxy, or a $C_1$-$C_3$ alkyl group optionally substituted with from 1-3 halogen substituents.

14. A pharmaceutical composition comprising an effective amount of a compound according to claim 1, optionally in combination with a pharmaceutically acceptable carrier, additive or excipient.

15. The pharmaceutical composition according to claim 14 comprising an effective amount of an additional antiviral agent.

16. A composition according to claim 14 further in combination with at least one anticancer agent.

17. A method of reducing the likelihood of a viral infection caused by a viral agent selected from the group consisting of Hepatitis B virus (HBV), Hepatitis C virus (HCV), Herpes Simplex 1 (HSV-1), Herpes Simplex 2 (HSV-2), cytomegalovirus (CMV), Varicella Zoster virus (VZV) and Epstein Barr virus (EBV) in a patient at risk for a viral infection comprising administering to said patient an effective amount of a composition according to claim 14.

18. The compound
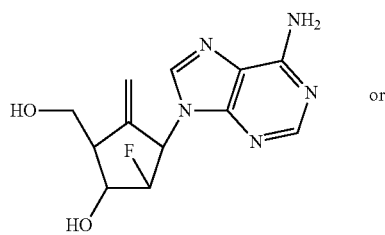 or
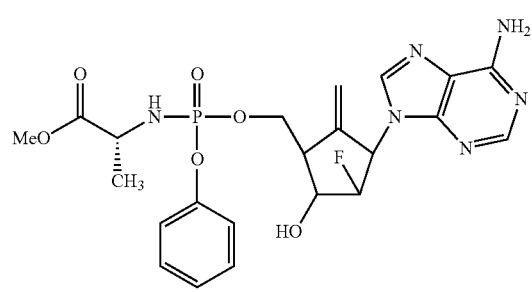
or a pharmaceutically acceptable salt thereof.
19. The compound according to claim 18 which is
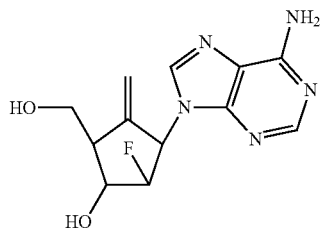
or a pharmaceutically acceptable salt thereof.
20. The compound according to claim 18 which is
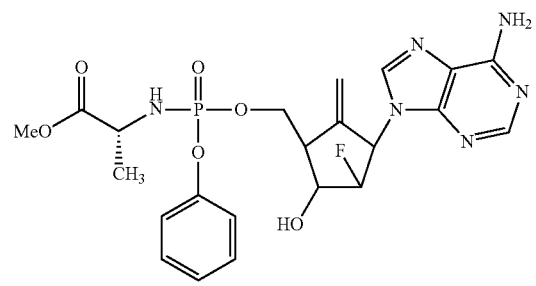
or a pharmaceutically acceptable salt thereof.
* * * * *